US010208049B2

(12) United States Patent
Palczewski et al.

(10) Patent No.: US 10,208,049 B2
(45) Date of Patent: *Feb. 19, 2019

(54) COMPOUNDS AND METHODS OF TREATING OCULAR DISORDERS

(71) Applicant: Case Western Reserve University, Cleveland, OH (US)

(72) Inventors: Krzysztof Palczewski, Cleveland, OH (US); Akiko Maeda, Cleveland, OH (US); Marcin Golczak, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/634,159

(22) Filed: Jun. 27, 2017

(65) Prior Publication Data

US 2018/0134714 A1 May 17, 2018

Related U.S. Application Data

(63) Continuation of application No. 14/272,131, filed on May 7, 2014, now abandoned, which is a continuation of application No. 13/492,193, filed on Jun. 8, 2012, now Pat. No. 8,722,669, which is a continuation-in-part of application No. PCT/US2010/059426, filed on Dec. 8, 2010.

(60) Provisional application No. 61/267,645, filed on Dec. 8, 2009.

(51) Int. Cl.
| | |
|---|---|
| *C07D 487/04* | (2006.01) |
| *A61K 31/4162* | (2006.01) |
| *A61K 31/4184* | (2006.01) |
| *A61K 31/428* | (2006.01) |
| *A61K 31/56* | (2006.01) |
| *C07C 211/01* | (2006.01) |
| *C07C 229/12* | (2006.01) |
| *C07C 229/60* | (2006.01) |
| *C07C 229/64* | (2006.01) |
| *C07C 237/48* | (2006.01) |
| *C07C 251/58* | (2006.01) |
| *C07C 317/36* | (2006.01) |
| *C07D 261/04* | (2006.01) |
| *A61K 9/00* | (2006.01) |

(52) U.S. Cl.
CPC ........ *C07D 487/04* (2013.01); *A61K 31/4162* (2013.01); *A61K 31/4184* (2013.01); *A61K 31/428* (2013.01); *A61K 31/56* (2013.01); *C07C 211/01* (2013.01); *C07C 229/12* (2013.01); *C07C 229/60* (2013.01); *C07C 229/64* (2013.01); *C07C 237/48* (2013.01); *C07C 251/58* (2013.01); *C07C 317/36* (2013.01); *C07D 261/04* (2013.01); *A61K 9/0048* (2013.01)

(58) Field of Classification Search
None
See application file for complete search history.

(56) References Cited

U.S. PATENT DOCUMENTS

| | | |
|---|---|---|
| 4,024,175 A | 5/1977 | Stazinger et al. |
| 4,085,225 A | 4/1978 | Welle et al. |
| 4,572,909 A | 2/1986 | Campbell et al. |
| 4,826,860 A | 5/1989 | Johnson et al. |
| 5,061,703 A | 10/1991 | Bormann et al. |
| 5,077,033 A | 12/1991 | Viegas et al. |
| 5,185,351 A | 2/1993 | Finkelstein et al. |
| 5,559,111 A | 9/1996 | Goschke et al. |
| 5,563,175 A | 10/1996 | Silverman et al. |
| 5,684,189 A | 11/1997 | Silverman et al. |
| 5,811,446 A | 9/1998 | Thomas |
| 6,001,876 A | 12/1999 | Singh |
| 6,197,819 B1 | 3/2001 | Silverman et al. |
| 6,310,040 B1 | 10/2001 | Bozyczko-Coyne et al. |
| 6,569,443 B1 | 5/2003 | Dawson et al. |
| 6,949,518 B1 | 9/2005 | Chu et al. |
| 7,108,982 B1 | 9/2006 | Hageman |
| 7,479,481 B2 | 1/2009 | Molina |
| 7,488,749 B2 | 2/2009 | Schraermeyer |
| 8,722,669 B2 | 5/2014 | Palczewski et al. |
| 2002/0143017 A1 | 10/2002 | Mylari |
| 2004/0254154 A1 | 12/2004 | Ashton |

(Continued)

FOREIGN PATENT DOCUMENTS

| | | |
|---|---|---|
| EP | 0797442 B1 | 5/2003 |
| EP | 1165058 B1 | 5/2005 |

(Continued)

OTHER PUBLICATIONS

Ettaiche et al., Riluzole Improves Functional Recovery after Ischemia in the Rat Retina. IOVS, Mar. 1999, vol. 40, No. 3, pp. 729-736.

(Continued)

*Primary Examiner* — Craig D Ricci
(74) *Attorney, Agent, or Firm* — Cooley LLP; Heidi A. Erlacher; Chen Chen

(57) ABSTRACT

A method of treating an ocular disorder in a subject associated with aberrant all-trans-retinal clearance in the retina, the method comprising administering to the subject a therapeutically effective amount of a primary amine compound of formula:

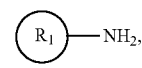

wherein $R_1$ is an aliphatic and/or aromatic compound.

20 Claims, 9 Drawing Sheets

(56) References Cited

U.S. PATENT DOCUMENTS

| | | |
|---|---|---|
| 2004/0259945 A1 | 12/2004 | Brewer et al. |
| 2005/0159410 A1 | 7/2005 | Zhang |
| 2005/0277698 A1 | 12/2005 | Hughes et al. |
| 2006/0110428 A1 | 5/2006 | deJuan et al. |
| 2006/0134226 A1 | 6/2006 | Leonard |
| 2006/0135460 A1 | 6/2006 | Widder et al. |
| 2006/0167088 A1 | 7/2006 | Widder et al. |
| 2006/0210604 A1 | 9/2006 | Dadey et al. |
| 2006/0233859 A1 | 10/2006 | Whitcup et al. |
| 2006/0252107 A1 | 11/2006 | Kubota et al. |
| 2006/0257486 A1 | 11/2006 | Owen et al. |
| 2006/0281821 A1 | 12/2006 | Palczewski et al. |
| 2007/0112017 A1 | 5/2007 | Barlow et al. |
| 2007/0135481 A1 | 6/2007 | Jordan et al. |
| 2007/0167527 A1 | 7/2007 | Burke et al. |
| 2007/0197491 A1 | 8/2007 | Robin et al. |
| 2007/0225217 A1 | 9/2007 | Chappell et al. |
| 2008/0176952 A1 | 7/2008 | Rando |
| 2008/0221208 A1 | 9/2008 | Palczewski et al. |
| 2008/0249042 A1 | 10/2008 | Moise et al. |
| 2008/0269324 A1 | 10/2008 | Rando |
| 2008/0274453 A1 | 11/2008 | Hageman |
| 2008/0300292 A1 | 12/2008 | Letts et al. |
| 2009/0053232 A1 | 2/2009 | Eroglu et al. |
| 2009/0098145 A1 | 4/2009 | Mata et al. |
| 2009/0099170 A1 | 4/2009 | Nunes et al. |
| 2010/0035986 A1 | 2/2010 | Maeda et al. |
| 2011/0288170 A1 | 11/2011 | Palczewski et al. |
| 2012/0041073 A1 | 2/2012 | Palczewski et al. |
| 2012/0295895 A1 | 11/2012 | Palczewski et al. |
| 2012/0322891 A1 | 12/2012 | Palczewski et al. |
| 2014/0357611 A1 | 12/2014 | Palczewski et al. |

FOREIGN PATENT DOCUMENTS

| | | |
|---|---|---|
| EP | 1930046 A1 | 6/2008 |
| JP | 2008-516961 A | 5/2008 |
| JP | 2009-501224 A | 1/2009 |
| WO | WO 2000/076958 A2 | 12/2000 |
| WO | WO 2001/006262 A1 | 1/2001 |
| WO | WO 2002/000209 A2 | 1/2002 |
| WO | WO 2002/043762 A2 | 6/2002 |
| WO | WO 2004/033444 A1 | 4/2004 |
| WO | WO 2004/054565 A1 | 7/2004 |
| WO | WO 2005/037262 A1 | 4/2005 |
| WO | WO 2005/056113 A1 | 6/2005 |
| WO | WO 2005/066147 A1 | 7/2005 |
| WO | WO 2005/067891 A1 | 7/2005 |
| WO | WO 2005/068460 A1 | 7/2005 |
| WO | WO 2005/075447 A1 | 8/2005 |
| WO | WO 2005/079781 A1 | 9/2005 |
| WO | WO 2006/007314 A1 | 1/2006 |
| WO | WO 2006/012521 A2 | 2/2006 |
| WO | WO 2006/014484 A2 | 2/2006 |
| WO | WO 2006/015075 A1 | 2/2006 |
| WO | WO 2006/015930 A1 | 2/2006 |
| WO | WO 2006/029411 A2 | 3/2006 |
| WO | WO 2006/039327 A2 | 4/2006 |
| WO | WO 2006/039558 A2 | 4/2006 |
| WO | WO 2006/044472 A1 | 4/2006 |
| WO | WO 2006/044617 A1 | 4/2006 |
| WO | WO 2006/055526 A2 | 5/2006 |
| WO | WO 2006/064281 A1 | 6/2006 |
| WO | WO 2006/074025 A1 | 7/2006 |
| WO | WO 2006/086744 A2 | 8/2006 |
| WO | WO 2006/091761 A1 | 8/2006 |
| WO | WO 2006/116591 A2 | 11/2006 |
| WO | WO 2007/008562 A2 | 1/2007 |
| WO | WO 2007/014323 A2 | 2/2007 |
| WO | WO 2007/019503 A2 | 2/2007 |
| WO | WO 2007/020103 A2 | 2/2007 |
| WO | WO 2007/128884 A1 | 11/2007 |
| WO | WO 2007/150046 A2 | 12/2007 |
| WO | WO 2008/036678 A2 | 3/2008 |
| WO | WO 2008/054639 A2 | 5/2008 |
| WO | WO 2008/095253 A1 | 8/2008 |
| WO | WO 2008/098027 A2 | 8/2008 |
| WO | WO 2008/104861 A1 | 9/2008 |
| WO | WO 2009/023411 A1 | 2/2009 |
| WO | WO 2009/023877 A2 | 2/2009 |
| WO | WO 2009/029762 A2 | 3/2009 |
| WO | WO 2009/051671 A1 | 4/2009 |
| WO | WO 2009/082039 A1 | 7/2009 |
| WO | WO 2009/111648 A1 | 9/2009 |
| WO | WO 2010/015029 A1 | 2/2010 |
| WO | WO 2010/080976 A1 | 7/2010 |
| WO | WO 2010/138671 A1 | 12/2010 |
| WO | WO 2011/107750 A2 | 9/2011 |
| WO | WO 2012/098281 A2 | 7/2012 |

OTHER PUBLICATIONS

Gahlot et al., Effect of Penicillamine on the sensori-neural deafness of retinitis pigmentosa. The Journal of Laryngology and Otology, Dec. 1977, 91(12): 1107-1111.

Golczak et al., An Acyl-covalent Enzyme Intermediate of lecithin:Retinol Acyltransferase. J. bio Chem, Jul. 12, 2010, 285: 29217-29222.

Kiser et al., Chemistry of the Retinoid (Visual) Cycle. Chem Rev. 2014; 114:194-232.

Kiser et al., Key enzymes of the retinoid (visual) cycle in vertebrate retina. Biochim Biophys Acta. Jan. 2012; 1821(1):137-51. doi: 10.1016/j.bbalip.2011.03.005. Epub Apr. 5, 2011.

Kiser et al., Membrane-Binding and Enzymatic Properties of RPE65. Prog. Retin Eye Res., Sep. 2010; 29(5): 428-442.

Maeda et al., Evaluation of Potential Therapies for a Mouse Model of Human Age-Related Macular Degeneration Caused by Delayed all-Trans-Retinol Clearance. Investigative Opthalmology & Visual Science, Oct. 2009, vol. 50, No. 10.

Maeda et al., Limited roles of Rdh8, Rdh12, and Abca4 in all-trans-retinal clearance in mouse retina. Invest Opthalmol V is Sci. Nov. 2009; 50(11):5435-43. doi: 10.1167/iovs.09-3944. Epub Jun. 24, 2009.

Maeda et al., Primary amines protect against retinal degeneration in mouse models of retinopathies. Nature Chemical Biology, vol. 8, Feb. 2012, pp. 170-178.

Maeda et al., Primary amines protect against retinal degeneration in mouse models of retinopathies. Nature Chemical Biology, vol. 8, Feb. 2012, pp. 170-178. Supplemental Information. 37 pages.

Maeda et al., Redundant and unique roles of retinol dehydrogenases in the mouse retina. Proc Natl Acad Sci USA. Dec. 4, 2007; 104(49):19565-70. Epub Nov. 28, 2007.

Maeda et al., Retinal photodamage mediated by all-trans-retinal. Photochem Photobiol. Nov.-Dec. 2012; 88(6):1309-19. doi: 10.1111/j.1751-1097.2012.01143.x Epub Apr. 24, 2012.

Maeda et al., Retinol dehydrogenases (RDH12) protects photoreceptors from light-induced degeneration in mice. J Biol Chem. Dec. 8, 2006; 281(49):27697-704. Epub Oct. 10, 2006.

Maeda et al., Retinopathy in Mice Induced by Disrupted All-trans-retinal Clearance. J. Biol. Chem. 2008, 283:26684-26693.

Maeda et al., Role of photoreceptor-specific retinol dehydrogenase in the retinoid cycle in vivo. J. Biol Chem. May 13, 2005; 280(19):18822-32. Epub Mar. 8, 2005.

Palcziewski et al., Retinoids for Treatment of Retinal Diseases. Trends Pharmacol Sci. Jun. 2010; 31(6): 284-295.

Parker et al., Retinol dehydrogenases (RDHs) in the visual cycle. Exp Eye res. Dec. 2010; 91(6):788-92. doi: 10.1016/j.exer.2010.08/013. Epub Aug. 27, 2010.

Rapp et al., The Effects of Local Anaesthetics on Retinal Function. Vision Res. Vole 22, pp. 1097-1103, 1982.

Seo et al., Dapsone Maculopathy. Korean I. Opthalmol, vol. 11(1): 70-73, 1997.

Sun et al., Novel RDH12 mutations associated with Leber congenital amaurosis and cone-rod dystrophy: biochemical and clinical evaluations. Vision Res. Jul. 2007; 47(15):2055-66. Epub May 21, 2007.

(56) References Cited

OTHER PUBLICATIONS

Tsybovsky et al., The ATP-Binding Cassette Transporter ABCA4: Structural and Functional Properties and Role in Retinol Disease. Adv Exp. Med Biol. 2010; 703: 105-125.
Weng et al., Insights into the function of Rim protein in photoreceptors and etiology of Stargardt's disease from the phenotype in aber knockout mice. Cell. Jul. 9, 1999; 98(1): 13-23.

Differential spectrum between unprotonated and protonated Schiff base.

Grading with OCT
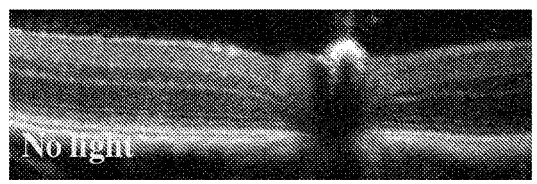
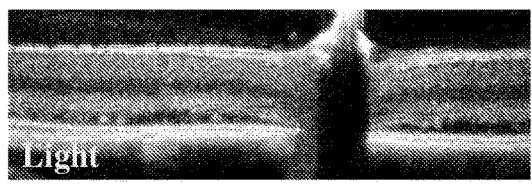
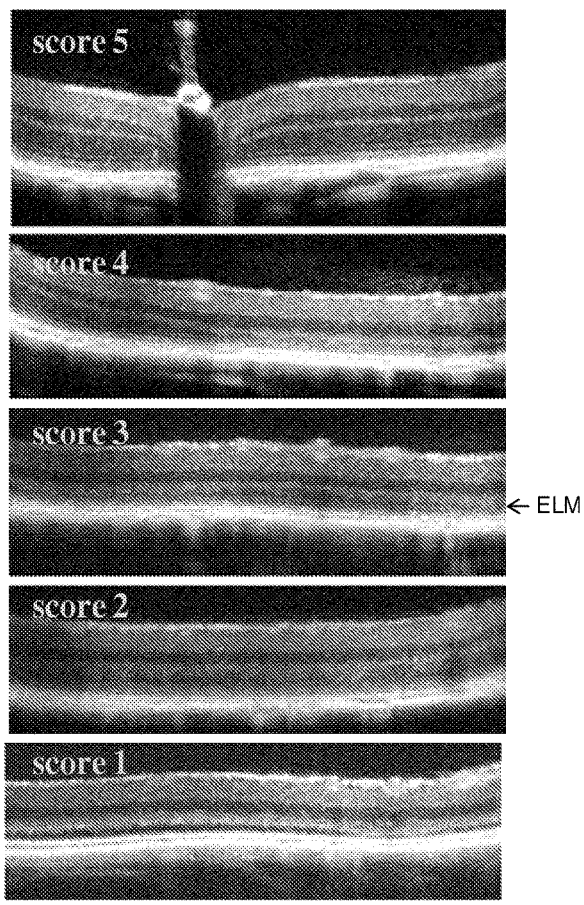
effective
5
↓
1
not effective
← ELM
Fig. 9

COMPOUNDS AND METHODS OF TREATING OCULAR DISORDERS

RELATED APPLICATIONS

This application is a continuation of U.S. application Ser. No. 14/272,131, filed on May 7, 2014, which is a continuation of and claims priority under 35 U.S.C. § 120 to U.S. application Ser. No. 13/492,193, filed Jun. 8, 2012, now U.S. Pat. No. 8,722,669, which is a Continuation-in-Part of PCT/US2010/059426, filed Dec. 8, 2010, which claims priority from U.S. Provisional Application No. 61/267,645, filed Dec. 8, 2009, the subject matter of which are incorporated herein by reference in their entirety.

GOVERNMENT FUNDING

This invention was made with government support under Grant No. EY09339 awarded by The National Institute of Health. The United States Government has certain rights in the invention.

TECHNICAL FIELD

This application relates to compounds and methods of treating ocular and/or retinal disorders that are associated with aberrant all-trans-retinal clearance in the retina, and more particularly to compounds and methods of treating retinal degeneration and/or retinal disorders using primary amine compounds.

BACKGROUND

The retinoid (visual) cycle is a complex enzymatic pathway essential for regeneration of the visual chromophore, 11-cis-retinal, a component of rhodopsin and cone opsins that undergoes activation by light in vertebrate eyes. Maintaining continuous vision and preserving the health of photoreceptors requires an adequate continuing supply of this aldehyde so vertebrates evolved the retinoid cycle to achieve this objective. The pathway operates in both photoreceptor cells and the retinal pigmented epithelium (RPE), converting all-trans-retinal back to 11-cisi-retinal by several chemical transformations. Whereas the classical vertebrate retinoid cycle contributes primarily to regeneration of rhodopsin in rod cells, RPE65-based chromophore production may also be important for cone function.

Inadequate availability and/or processing of vitamin A to the visual chromophore, 11-cis-retinal can adversely affect vertebrate rhodopsin regeneration and visual congenital or progressive blindness in humans. Inactivation of non-redundant enzymes of the retinoid cycle, e.g., either LRAT that esterifies all-trans-retinol or the retinoid isomerase called RPE65, produces Leber congenital amaurosis (LCA), a leading cause of inherited childhood blindness. LCA is an autosomal recessive, early onset severe retinal dystrophy that accounts for 5% of all inherited retinal dystrophies. Insufficient vitamin A in the diet also can lead to progressive deterioration of vision and ultimately blindness, a major problem in underdeveloped countries.

Whereas inadequate 11-cis-retinal production leads to congenital blindness in humans, accumulation of the photoisomerized chromophore all-trans-retinal also can be detrimental. Such is the case when this reactive aldehyde is not efficiently cleared from the internal membranes of retinal outer segment discs. Clearance of all-trans-retinal involves two steps: 1). Translocation of all-trans-retinal across the photoreceptor disc membranes by ATP-binding cassette transporter 4 (ABCA4), and 2). Reduction of all-trans-retinal to all-trans-retinol by retinol dehydrogenase 8 (RDH8), expressed in the outer segments of photoreceptors, and by RDH12 located in photoreceptor inner segments.

ABCA4, also known as ABCR or the rim protein, localizes to the rim of photoreceptor discs and transfers all-trans-retinal from the inside to the outside of disc membranes after it is released from visual pigments. Mutations in ABCA4 can cause Stargardt macular degeneration, cone-rod dystrophy, or recessive RP. Also, heterozygous mutations in ABCA4 increase the risk of developing age-related macular degeneration.

Di-retinoid-pyridinium-retinylethanolamine (A2E) and retinal dimer (RALdi) conjugates are the major fluorophores of lipofuscins produced from all-trans-retinal. Even in the presence of a functional transporter, both A2E and RALdi can accumulate as a consequence of aging together with light exposure and produce toxic effects on RPE cells. Patients affected by age-related macular degeneration, Stargardt disease with a disabled ABCA4 gene or other retinal diseases associated with lipofuscin accumulation develop retinal degeneration. ABCA4 mutations also are linked to a high risk of AMD.

SUMMARY

This application relates to compounds and methods of treating an ocular disorder in a subject associated with aberrant all-trans-retinal clearance in the retina. The ocular disorder can include, for example, retinal disorders, such as retinal degeneration, macular degeneration, including age-related macular degeneration, Stargardt disease, geographic atrophy, and retinitis pigmentosa. The method of treating the ocular disorder in a subject can include administering to the subject a therapeutically effective amount of a primary amine compound of formula:

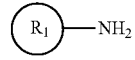

wherein $R_1$ is an aliphatic and/or aromatic compound. The primary amine compound upon administration to the subject forms a reversible Schiff-base with the all-trans-retinal without adversely affecting normal retinoid cycle performance. The primary amine compound when administered to a Rdh8$^{-/-}$Abca4$^{-/-}$ mouse increases the optical coherence tomography score of the mouse, which reflects severity in retinal morphology, to at least about 2.5 and increases 11-cis-retinal amount at least about 30% in comparison to untreated control animal. The primary amine compound is not a local anesthetic, which includes an aromatic amine that demonstrates sodium channel blockade when administered to the subject.

In an aspect of the application, the primary amine compound does not inhibit RPE65 enzymatic activity or any other proteins involved in retinoid metabolism in the eye of the subject. The primary amine compounds can reduce the formation of A2E and/or retinal dimer in the subject's retina and promote 11-cis-retinal production in the subject. The primary amine compound does not induce night blindness.

In another aspect of the application, the primary amine compound can have a molecular weight less than about 500 and be delivered to the subject by at least one of topical administration, systemic administration, intravitreal injection, and/or intraocular delivery. In one example, the primary amine can be provided in an ocular preparation for sustained delivery.

BRIEF DESCRIPTION OF THE DRAWINGS

FIG. 9 illustrates OCT images showing grading of retinas.

DETAILED DESCRIPTION

Figure 1:
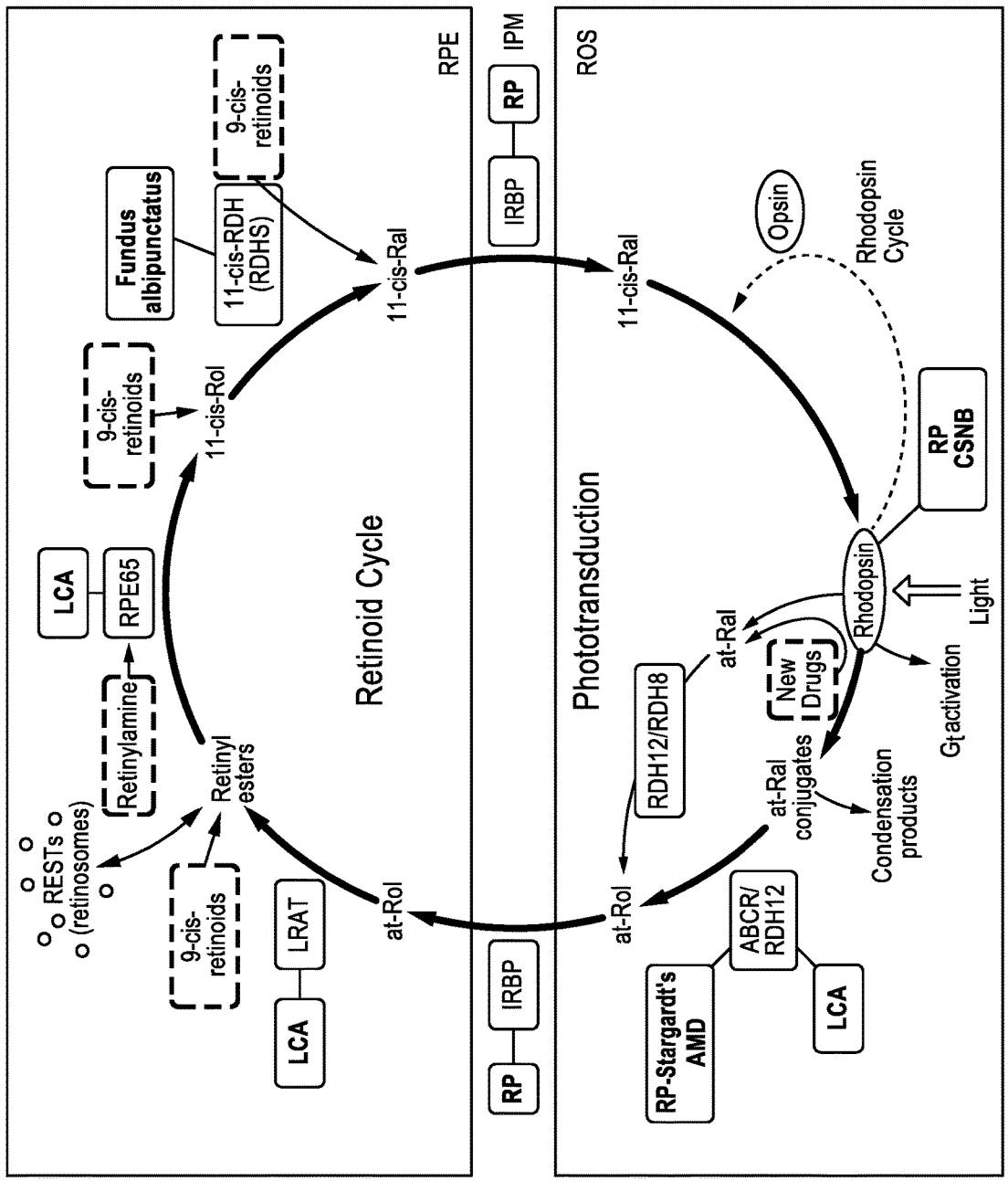
FIG. 1 is a schematic illustration of the visual cycle.

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

It will be noted that the structure of some of the compounds of the application include asymmetric (chiral) carbon atoms. It is to be understood accordingly that the isomers arising from such asymmetry are included within the scope of the invention, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" refers to compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

The term "chiral isomer" refers to a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n−1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric isomers" refer to the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Further, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative", refers to compounds that have a common core structure, and are substituted with various groups as described herein. For example, all of the compounds represented by formula I are primary amines and have formula I as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" refer to modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The term "treating" refers to inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" refers to stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term a "pharmaceutical composition" refers to a formulation containing the disclosed compounds in a form suitable for administration to a subject. The pharmaceutical composition can be in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, and the like. Dosage forms for the topical or transdermal administration of a compound of this invention include powders, sprays, ointments, pastes, creams, lotions, gels, solutions, patches and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" refers to a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" refers to compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" refers to pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated within the scope of the claims.

The phrase "pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of salts are found in Remington's Pharmaceutical Sciences, 18th ed. (Mack Publishing Company, 1990). For example, salts can include, but are not limited to, the hydrochloride and acetate salts of the aliphatic amine-containing, hydroxyl amine-containing, and imine-containing compounds of the present invention.

It should be understood that all references to pharmaceutically acceptable salts include solvent addition forms (solvates) or crystal forms (polymorphs) as defined herein, of the same salt.

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds of the present invention can be delivered in prodrug form. Thus, the present application is intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs the present invention are prepared by modifying functional groups present in the compound in such a way that the modifications are cleaved, either in routine manipulation or in vivo, to the parent compound. Prodrugs include compounds described herein wherein a hydroxy, amino, sulfhydryl, carboxy, or carbonyl group is bonded to any group that may be cleaved in vivo to form a free hydroxyl, free amino, free sulftydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of Formula I, and the like (e.g., Bundegaard, H. "Design of Prodrugs" p 1-92, Elesevier, New York-Oxford (1985)).

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, $2^{nd}$ ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

The term "amine protecting group" refers to a functional group that converts an amine, amide, or other nitrogen-containing moiety into a different chemical group that is substantially inert to the conditions of a particular chemical reaction. Amine protecting groups can be removed easily and selectively in good yield under conditions that do not affect other functional groups of the molecule. Examples of amine protecting groups include, but are not limited to, formyl, acetyl, benzyl, t-butyldimethylsilyl, t-butdyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Other amine protecting groups can be identified by those of skill in the art.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" refers to solvent addition forms that contain either stoichiometric or non stoichiometric amounts of solvent. Some compounds have a tendency to trap a fixed molar ratio of solvent molecules in the crystalline solid state, thus forming a solvate. If the solvent is water, the solvate formed is a hydrate; when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g. an enolate); 3. protonation at a different position of the anion; Acid: 1. protonation; 2. formation of a delocalized cation; 3. deprotonation at a different position adjacent to the cation.

The term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

A "patient," "subject," or "host" to be treated by the subject method may mean either a human or non-human animal, such as primates, mammals, and vertebrates.

The term "prophylactic or therapeutic" treatment refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" refer to molecules and other agents that are biologically, physiologically, or pharmacologically active substances that act locally or systemically in a patient or subject to treat a disease or condition, such as retinal degeneration or other forms of retinal disease whose etiology involves aberrant clearance of all trans-retinal. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" is an art-recognized term. In certain embodiments, the term refers to an amount of a therapeutic agent that, when incorporated into a polymer, produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" refer to the dose of a drug, which produces 50% of its maximum response or effect, or alternatively, the dose, which produces a pre-determined response in 50% of test subjects or preparations. The term "LD50" refers to the dose of a drug, which is lethal in 50% of test subjects. The term "therapeutic index" refers to the therapeutic index of a drug, defined as LD50/ED50.

The term "substituted," as used herein, means that any one or more hydrogens on the designated atom is replaced with a selection from the indicated group, provided that the designated atom's normal valency is not exceeded, and that the substitution results in a stable compound. When the substituent is keto (i.e., =O), then 2 hydrogens on the atom are replaced. Ring double bonds, as used herein, are double bonds that are formed between two adjacent ring atoms (e.g., C=C, C=N, or N=N).

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), the invention is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

As used herein, "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)).

As used herein, "alkenyl" is intended to include hydrocarbon chains of either straight or branched configuration having one or more carbon-carbon double bonds occurring at any stable point along the chain. For example, $C_{2-6}$ alkenyl is intended to include $C_2$, $C_3$, $C_4$, $C_5$, and $C_6$ alkenyl groups. Examples of alkenyl include, but are not limited to, ethenyl and propenyl.

As used herein, "alkynyl" is intended to include hydrocarbon chains of either straight or branched configuration having one or more carbon-carbon triple bonds occurring at any stable point along the chain. For example, $C_{2-6}$ alkynyl is intended to include $C_2$, $C_3$, $C_4$, $C_5$, and $C_6$ alkynyl groups. Examples of alkynyl include, but are not limited to, ethynyl and propynyl.

Furthermore, "alkyl", "alkenyl", and "alkynyl" are intended to include moieties which are diradicals, i.e., having two points of attachment. A nonlimiting example of such an alkyl moiety that is a diradical is —CH$_2$CH$_2$—, i.e., a $C_2$ alkyl group that is covalently bonded via each terminal carbon atom to the remainder of the molecule.

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and al kylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams such as azetidinones and pyrrolidinones, sultams, and sultones. Heterocyclic groups such as pyrrole and furan can have aromatic character. They include fused ring structures such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

As used herein, "halo" or "halogen" refers to fluoro, chloro, bromo, and iodo. "Counterion" is used to represent a small, negatively charged species such as fluoride, chloride, bromide, iodide, hydroxide, acetate, and sulfate.

"Stable compound" and "stable structure" are meant to indicate a compound that is sufficiently robust to survive isolation, and as appropriate, purification from a reaction mixture, and formulation into an efficacious therapeutic agent.

"Free compound" is used herein to describe a compound in the unbound state.

"Extinction coefficient" is a constant used in the Beer-Lambert Law which relates the concentration of the substance being measured (in moles) to the absorbance of the substance in solution (how well the substance in solution blocks light beamed through it from getting out on the other side). It is an indicator of how much light a compound absorbs at a particular wavelength.

In the specification, the singular forms also include the plural, unless the context clearly dictates otherwise. Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

"Small molecule" refers to a molecule, which has a molecular weight of less than about 2000 amu, or less than about 1000 amu, and even less than about 500 amu.

All percentages and ratios used herein, unless otherwise indicated, are by weight.

The term "retina" refers to a region of the central nervous system with approximately 150 million neurons. It is located at the back of the eye where it rests upon a specialized epithelial tissue called retinal pigment epithelium or RPE. The retina initiates the first stage of visual processing by transducing visual stimuli in specialized neurons called "photoreceptors". Their synaptic outputs are processed by elaborate neural networks in the retina and then transmitted to the brain. The retina has evolved two specialized classes of photoreceptors to operate under a wide range of light conditions. "Rod" photoreceptors transduce visual images under low light conditions and mediate achromatic vision. "Cone" photoreceptors transduce visual images in dim to bright light conditions and mediate both color vision and high acuity vision.

Every photoreceptor is compartmentalized into two regions called the "outer" and "inner" segment. The inner segment is the neuronal cell body containing the cell nucleus. The inner segment survives for a lifetime in the absence of retinal disease. The outer segment is the region where the light sensitive visual pigment molecules are concentrated in a dense array of stacked membrane structures. Part of the outer segment is routinely shed and regrown in a diurnal process called outer segment renewal. Shed outer segments are ingested and metabolized by RPE cells.

The term "macula" refers to the central region of the retina, which contains the fovea where visual images are processed by long slender cones in high spatial detail ("visual acuity"). "Macular degeneration" is a form of retinal neurodegeneration, which attacks the macula and destroys high acuity vision in the center of the visual field. AMD can be in a "dry form" characterized by residual lysosomal granules called lipofuscin in RPE cells, and by extracellular deposits called "drusen". Drusen contain cellular waste products excreted by RPE cells. "Lipofuscin" and drusen can be detected clinically by ophthalmologists and quantified using fluorescence techniques. They can be the first clinical signs of macular degeneration.

Lipfuscin contains aggregations of A2E. Lipofuscin accumulates in RPE cells and poisons them by multiple known mechanisms. As RPE cells become poisoned, their biochemical activities decline and photoreceptors begin to degenerate. Extracellular drusen may further compromise RPE cells by interfering with their supply of vascular nutrients. Drusen also trigger inflammatory processes, which leads to choroidal neovascular invasions of the macula in one patient in ten who progresses to wet form AMD. Both the dry form and wet form progress to blindness.

The term "ERG" is an acronym for electroretinogram, which is the measurement of the electric field potential emitted by retinal neurons during their response to an experimentally defined light stimulus. ERG is a non-invasive measurement, which can be performed on either living subjects (human or animal) or a hemisected eye in solution that has been removed surgically from a living animal.

The term "RAL" means retinaldehyde. "Free RAL" is defined as RAL that is not bound to a visual cycle protein. The terms "trans-RAL" and "all-trans-RAL" are used interchangeably and mean all-trans-retinaldehyde.

Figure 2:
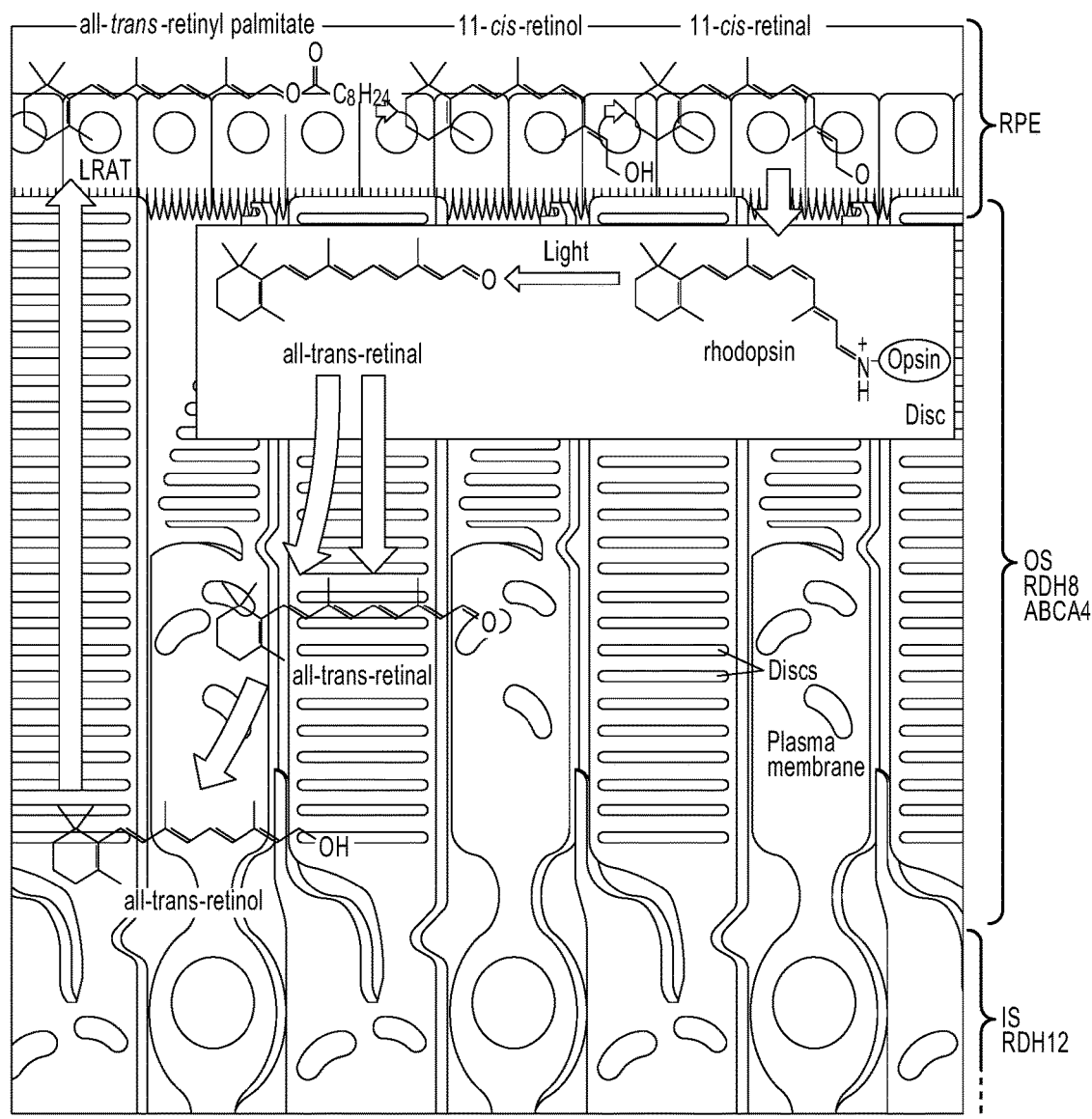
FIG. 2 is a schematic illustration of retinoid flow and all-trans-retinal clearance in the visual cycle.

An embodiment of the application relates to compounds and methods of treating an ocular disorder in a subject associated with aberrant all-trans-retinal clearance in the retina. The ocular disorder can include, for example, retinal disorders, such as macular degeneration, including age-related macular degeneration, geographic atrophy (GA), Stargardt disease, and retinitis pigmentosa. FIGS. 1 and 2 show the retinoid flow in the visual cycle including condensation of all-trans-RAL, and all-trans-RAL clearance. After 11-cis-retinal binds to opsin from rhodopsin, the resulting visual chromophore 11-cis-retinylidene is photoisomerized to all-trans-retinylidene, the precursor or all-trans-RAL that is later released. Most of the all-trans-RAL dissociates from opsin into the cytoplasm before it is reduced to all-trans-retinol by RDHs including RDH8. The fraction of all-trans-RAL that dissociates into disc lumens is transported by ABCA4 before is it is reduced. Thus, condensation products can be generated both within the disc lumens and the cytoplasm before it is reduced.

It was found that all-trans-RAL that has escaped sequestering by opsins in photoreceptor outer segments of the retina is toxic to retina cells and that aberrant all-trans-RAL clearance from the inner disc membrane to the outer disc membrane can cause retinal degeneration. The mechanism of all-trans-RAL toxicity can include plasma membrane permeability and mitochondrial poisoning that leads to caspase activation and mitochondrial associated cell death.

In accordance with an embodiment of the application, compounds used to treat an ocular disorder associated with aberrant all-trans-RAL clearance can include primary amines (i.e., primary amine compounds) that form reversible Schiff-bases with free all-trans-RAL, which has escaped sequestering in photoreceptor outer segments of the retina without adversely affecting normal retinoid cycle. Formation of a reversible Schiff base between RAL and the primary amine compounds described herein can control or modulate all-trans-RAL levels in the retina and prevent retina degeneration. The stability of the Schiff-bases formed between the primary amine compounds and the free RAL under physiologic conditions of the retina can be used to determine the efficacy of these compounds in treating the ocular disorder. The stability of the Schiff-bases formed from the primary amine compounds should be such that the level of free RAL in the retina is reduced to a level that is effective to mitigate retinal degeneration but not impair the normal retinoid cycle.

In an embodiment of the application, the primary amine compounds that can form stable Schiff-bases with all-trans-RAL under physiological conditions of the retina and that can inhibit retinal degeneration upon administration to a subject can be selected using an in vitro assay that measures the ability of a primary amine compound to form a Schiff base with retinal under physiological condition of the retina and in vivo assays that measure, respectively, 11-cis-retinal formation and the optical coherence tomography score of retinas of Rdh8$^{-/-}$Abca4$^{-/-}$ mice. Primary amine compounds that form a Schiff-base with all-trans-RAL or its metabolite under physiologic conditions of the retina and that when administered to a Rdh8$^{-/-}$Abca4$^{-/-}$ mouse increase the optical coherence tomography score of the mouse to at least about 2.5 and increase 11-cis-retinal amount at least about 30% in comparison to untreated control animal are effective in treating retinal degeneration in a subject associated with aberrant all-trans-RAL clearance. Primary amines compounds that do not form a form a Schiff-base with all-trans-RAL or its metabolite under physiologic conditions of the retina or which when administered to a Rdh8$^{-/-}$ Abca4$^{-/-}$ mouse do not increase the optical coherence tomography score of the mouse to at least about 2.5 and increase 11-cis-retinal amount at least about 30% in comparison to untreated control animal, were found to be ineffective in treating retinal degeneration in a subject associated with aberrant all-trans-RAL clearance. Additionally, therapeutic efficacy of the primary amine compounds of the application can be determined using an in vitro assay that measures the ability of a primary amine compound to improve viability of RPE cells treated with retinal.

In some embodiments, the primary amine compound can include the structural formula (I):

(I)

wherein $R_1$ is an aliphatic and/or aromatic compound.

Primary amine compounds having formula I that are used to treat retinal degeneration in accordance with an embodiment of the application can upon administration to the subject form a reversible Schiff-base with the all-trans-RAL without adversely affecting normal retinoid cycle performance and when administered to a Rdh8$^{-/-}$Abca4$^{-/-}$ mouse increase the optical coherence tomography score of the mouse to at least about 2.5 and increase 11-cis-retinal amount at least about 30% in comparison to untreated control animal. Primary amine compounds in accordance with the application, however, do not include and are not a local anesthetic, which includes an aromatic amine that demonstrates sodium channel blockade when administered to the subject.

Advantageously, the primary amine compounds in accordance with the application do not inhibit RPE65 enzymatic activity or any other proteins involved in retinoid metabolism in the eye of the subject. The primary amine compounds can reduce the formation of A2E and/or retinal dimer in the subject's retina, promote 11-cis-retinal production in the subject, and does not cause night blindness.

In some embodiments, primary compounds having formula I that upon administration to a subject form a reversible Schiff-base with the all-trans-RAL without adversely affecting normal retinoid cycle performance and that when administered to a Rdh8$^{-/-}$ Abca4$^{-/-}$ mouse increase the optical coherence tomography score of the mouse to at least about 2.5 and increase 11-cis-retinal amount at least about 30% in comparison to untreated control animal can be selected using the methods described in the Examples from known primary amine compounds.

In an embodiment of the application, the primary amine compounds can include known primary amine compounds having the following structural formulas:

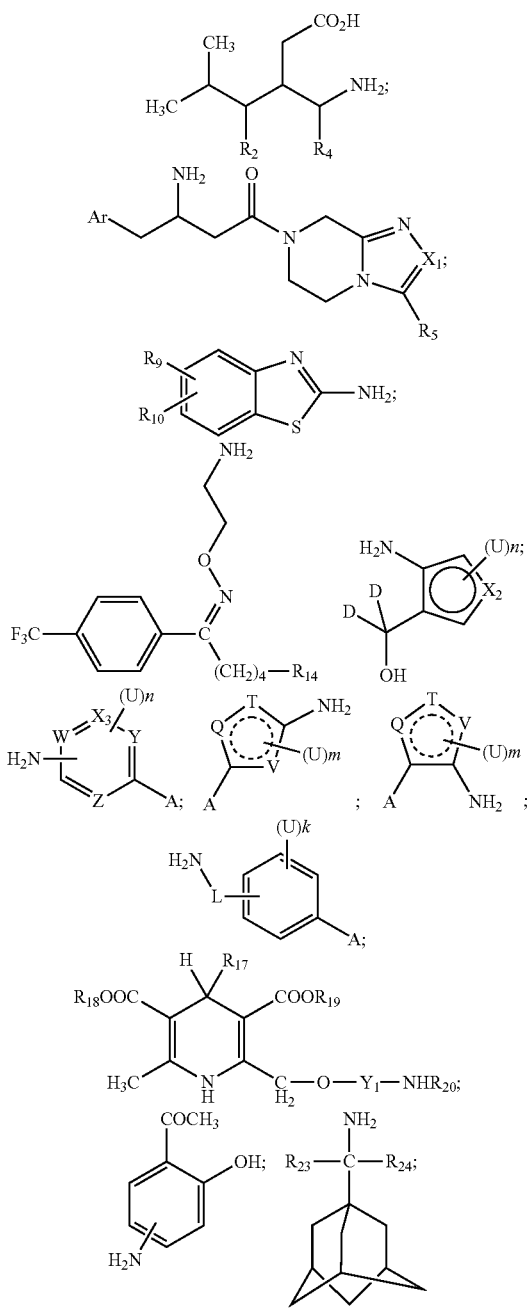

wherein $R_2$ is hydrogen or ($C_1$-$C_6$) straight chain or branched unsubstituted or substituted alkyl;

$R_3$ is straight or branched unsubstituted or substituted alkyl of from 1 to 8 carbon atoms, straight or branched alkenyl of from 2 to 8 carbon atoms, cycloalkyl of from 3 to 7 carbon atoms, alkoxy of from 1 to 6 carbon atoms, -alkylcycloalkyl, -alkylalkoxy, -alkyl, OH, -alkylphenyl, -alkylphenoxy, -phenyl or substituted phenyl;

$R_4$ is hydrogen or ($C_1$-$C_6$) straight chain or branched unsubstituted or substituted alkyl, or carboxyl;

Ar is phenyl which is unsubstituted or substituted with 1-5 of $R_7$, wherein $R_7$ is independently selected from the group consisting of:
(1) halogen,
(2) $C_{1-6}$ alkyl, which is linear or branched and is unsubstituted or substituted with 1-5 halogens,
(3) $OC_{1-6}$ alkyl, which is linear or branched and is unsubstituted or substituted with 1-5 halogens, and
(4) CN;

$X_1$ is selected from the group consisting of:
(1) N, and
(2) $CR_6$;

$R_5$ and $R_6$ are independently selected from the group consisting of:
(1) hydrogen,
(2) CN,
(3) $C_{1-10}$ alkyl, which is linear or branched and which is unsubstituted or substituted with 1-5 halogens or phenyl, which is unsubstituted or substituted with 1-5 substituents independently selected from halogen, CN, OH, $R_8$, $OR_8$, $NHSO_2$ $R_8$, $SO_2$ $R_8$, $CO_2$ H, and $CO_2$ $C_{1-6}$ alkyl, wherein the $CO_2$ $C_{1-6}$ alkyl is linear or branched,
(4) phenyl which is unsubstituted or substituted with 1-5 substituents independently selected from halogen, CN, OH, $R_8$, $OR_8$, $NHSO_2$ $R_8$, $SO_2$ $R_8$, $CO_2$ H, and $CO_2$ $C_{1-6}$ alkyl, wherein the $CO_2$ $C_{1-6}$ alkyl is linear or branched, and
(5) a 5- or 6-membered heterocycle which may be saturated or unsaturated comprising 1-4 heteroatoms independently selected from N, S and O, the heterocycle being unsubstituted or substituted with 1-3 substituents independently selected from oxo, OH, halogen, $C_{1-6}$ alkyl, and $OC_{1-6}$ alkyl, wherein the $C_{1-6}$ alkyl and $OC_{1-6}$ alkyl are linear or branched and optionally substituted with 1-5 halogens;

$R_8$ is $C_{1-6}$ alkyl, which is linear or branched and which is unsubstituted or substituted with 1-5 groups independently selected from halogen, $CO_2$ H, and $CO_2$ $C_{1-6}$ alkyl, wherein the $CO_2$ $C_{1-6}$ alkyl is linear or branched;

$R_9$ and $R_{10}$ may be the same or different and are hydrogen, straight or branched alkyl of from one to six carbon atoms, lower alkylaryl, lower alkenyl, phenyl, $CF_3$, hydroxy, lower alkoxy, lower alkylthio, lower alkylsulphonyl, $CF_3$ O, at the six position halogen, nitro, carboxy, lower alkoxycarbonyl, $NR_{11}R_{12}CO$, $NR_{11}R_{12}$, $R_{11}CONR_{12}$, CN, $NR_{11}R_{12}SO_2$, wherein $R_{11}$ and $R_{12}$ may be the same or different and are hydrogen, lower alkyl, or aryl; $R_9$ and $R_{10}$ may together form a carbocyclic or methylenedioxy ring;

$R_{14}$ is cyano, cyanomethyl, methoxymethyl, or ethoxymethyl;

$X_2$ is O, N(H), or S, het is a 5 or 6-membered heterocycle, n is 0, 1, 2, or 3, and each D is an unbranched lower alkyl group;

U is a substituent selected from halogen atom; cyano; lower alkyl wherein one or more hydrogen atoms on the lower alkyl group are optionally substituted by groups selected from a halogen atom, hydroxyl, carbamoyl, amino, aryl, and a monocyclic or bicyclic heterocyclic group containing one or more hetero-atoms selected from nitrogen, oxygen, and sulfur atoms; lower alkylthio wherein one or more hydrogen atoms on the alkyl group are optionally substituted by groups selected from a halogen atom, hydroxyl, carbamoyl, amino, and aryl; lower alkylsulfonyl wherein one or more hydrogen atoms on the alkyl group are optionally substituted by groups selected from a halogen atom, hydroxyl, carbamoyl, amino, and aryl; hydroxyl; lower alkoxy; formyl; lower alkylcarbonyl; arylcarbonyl; carboxyl; lower alkoxycarbonyl; carbamoyl; N-lower alkylcarbamoyl; N,N-di-lower alkylaminocarbonyl; amino; N-lower alkylamino; N,N-di-lower alkylamino; formylamino; lower alkylcarbonylamino; aminosulfonylamino; (N-lower alkylamino)sulfonylamino; (N,N-di-lower alkylamino)sulfonylamino; aryl, optionally substituted by groups selected from a halogen atom, hydroxyl, carbamoyl, aryl and amino; and a monocyclic or bicyclic heterocyclic group containing one or more hetero-atoms selected from nitrogen, oxygen, and sulfur atoms;

Q, T, and V are each, independently, N, S, O CU or CH;

W, X, Y, and Z are each, independently, N, S, O CU or CH, such that at least one of W, X, Y, and Z is N;

A is

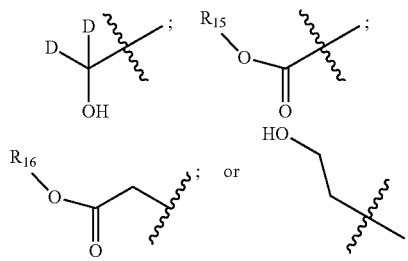

D is unbranched lower alkyl;

$R_{15}$ and $R_{16}$ are each independently substituted or unsubstituted $C_1$, $C_2$, $C_3$, $C_4$, $C_5$, $C_6$, $C_7$, or $C_8$, straight chain alkyl, or substituted or unsubstituted $C_3$, $C_4$, $C_5$, $C_6$, $C_7$, or $C_8$, branched chain alkyl;

L is a single bond or $CH_2$;

m is 0, 1, or 2;

n is 0, 1, 2, 3, or 4;

$Y_1$ is —$(CH_2)_2$—, —$(CH_2)_3$—, —$CH_2$ $CH(CH_3)$— or —$CH_2$ $C(CH_3)_2$—;

$R_{17}$ is aryl or heteroaryl;

$R_{18}$ and $R_{19}$ are each independently $C_1$-$C_4$ alkyl or 2-methoxyethyl;

$R_{20}$ is hydrogen, $C_1$-$C_4$ alkyl, 2-($C_1$-$C_4$ alkoxy)ethyl, cyclopropylmethyl, benzyl, or —$(CH_2)_{m1}COR_{21}$ where m1 is 1, 2 or 3 and $R^{21}$ is hydroxy, $C_1$-$C_4$ alkoxy or —$NR_{22}$ where $R_{22}$ hydrogen or $C_1$-$C_4$ alkyl;

$R_{23}$ and $R_{24}$ can be the same or different and are hydrogen, methyl, or ethyl as well as pharmaceutically acceptable salts thereof.

In other embodiments, the primary amine compound can be selected from the group consisting of:

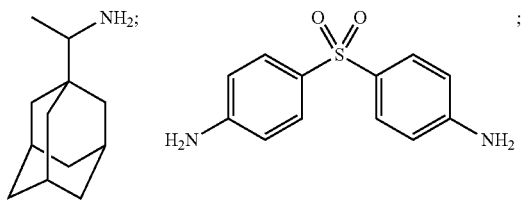

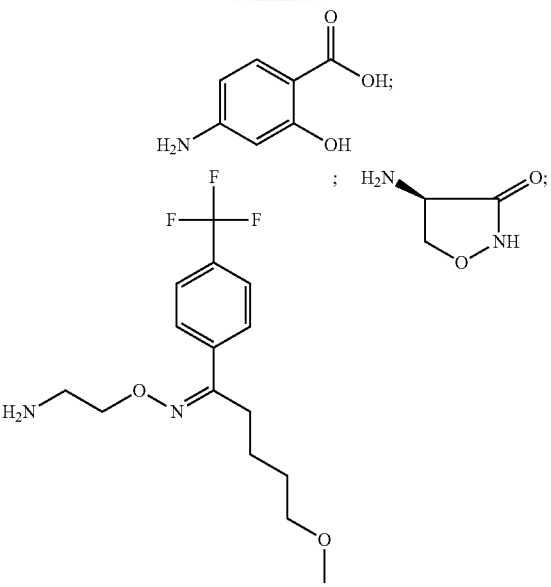

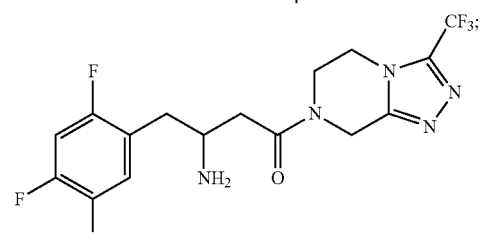

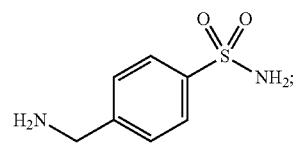

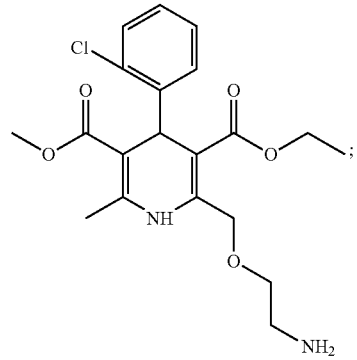

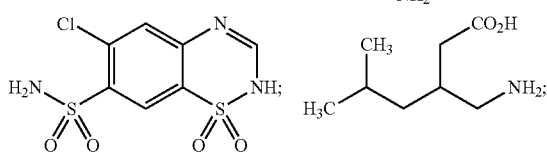

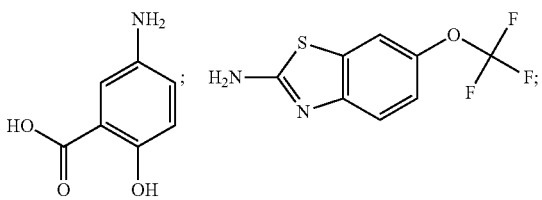 [SMILES: Nc1ccc(O)c(C(=O)O)c1 ; Nc1nc2ccc(OC(F)(F)F)cc2s1]

and pharmaceutically acceptable salts thereof.

In a still further embodiment, the primary amine compound can be selected from the group consisting of:

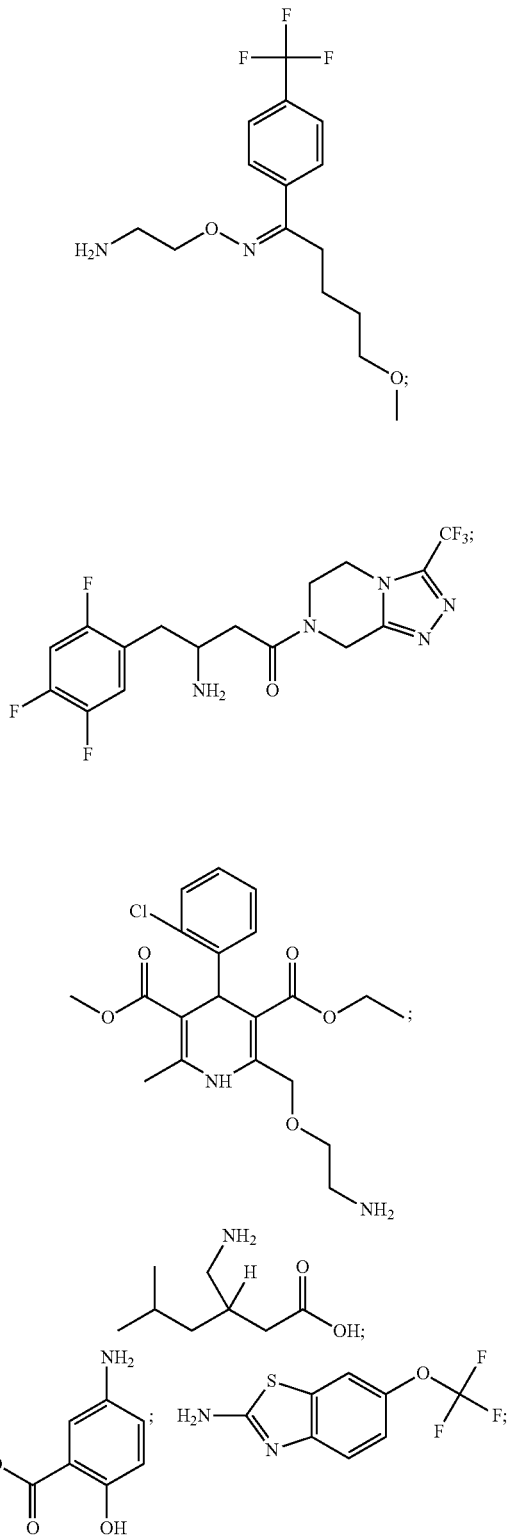

and pharmaceutically acceptable salts thereof.

In another embodiment, the primary compound can have the following structural formula:

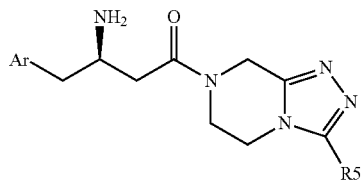

wherein Ar is phenyl which is unsubstituted or substituted with 1-5 substitutents which are independently selected from the group consisting of: (1) fluoro, (2) bromo, and (3) $CF_3$, $R_5$ is selected from the group consisting of: (1) hydrogen, and (2) $C_{1-6}$ alkyl, which is linear or branched and which is unsubstituted or substituted with phenyl or 1-5 fluoro.

In yet another embodiment, it is more preferred that Ar is selected from the group consisting of: (1) phenyl, (2) 2-fluorophenyl, (3) 3,4-difluorophenyl, (4) 2,5-difluorophenyl, (5) 2,4,5-trifluorophenyl, (6) 2-fluoro-4-(triflouromethyl)phenyl, and (7) 4-bromo-2,5-difluorophenyl and R5 is selected from the group consisting of: (1) hydrogen, (2) methyl, (3) ethyl, (4) $CF_3$, (5) $CH_2CF_3$, (5) $CF_2CF_3$ (6) phenyl, and (7) benzyl.

In another embodiment, the primary amine compound can be a monobasic dihydrogenphosphate salt of 4-oxo-4-[3-(trifluoromethyl)-5,6-dihydro[1,2,4]triazolo[4,3-a]pyrazin-7(8H)-yl]-1-(2,4,5-trifluorophenyl) butan-2-amine of the following structural formula:

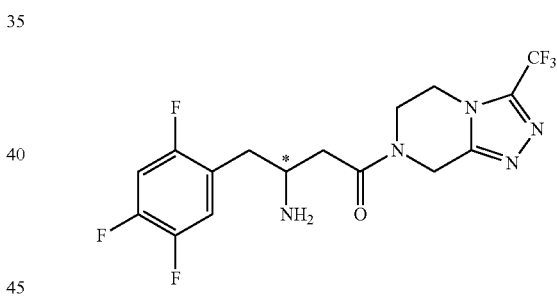

or a crystalline hydrate thereof. The crystalline hydrate can be a crystalline monohydrate of the dihydrogenphosphate salt.

The dihydrogenphosphate salt shown above has a center of asymmetry at the stereogenic carbon atom indicated with an * and can thus occur as a racemate, racemic mixture, and single enantiomers, with all isomeric forms being included in the present invention. The separate enantiomers, substantially free of the other, are included within the scope of the invention, as well as mixtures of the two enantiomers. Monobasic dihydrogenphosphate salt of 4-oxo-4-[3-(trifluoromethyl)-5,6-dihydro[1,2,4]triazolo[4,3-a]pyrazin-7(8H)-yl]-1-(2,4,5-trifluorophenyl) butan-2-amine.

In a further embodiment, the primary amine compound can be a dihydrogenphosphate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl) butan-2-amine of the following structural formula:

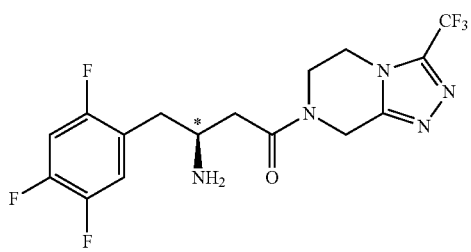

or a crystalline hydrate thereof.

In yet another embodiment, the primary amine compound can be a dihydrogenphosphate salt of (2S)-4-oxo-4-[3-(trifluoromethyl)-5,6-dihydro[1,2,4]triazolo[4,3-a]pyrazi-n-7 (8H)-yl]-1-(2,4,5-trifluorophenyl) butan-2-amine of the following structural formula:

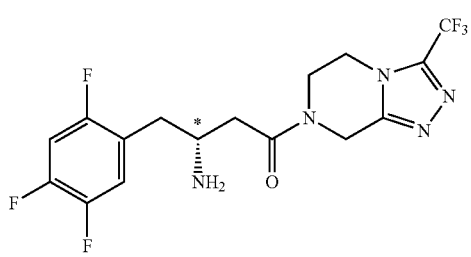 [SMILES: NC(CC(=O)N1CCn2c(nnc2C(F)(F)F)C1)Cc1cc(F)c(F)cc1F]

or a crystalline hydrate thereof.

In some embodiments, the primary amine compound is a compound having the following structural formula:

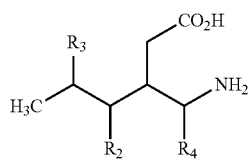

wherein $R_2$ is hydrogen or ($C_1$-$C_6$) straight chain or branched unsubstituted or substituted alkyl;

$R_3$ is straight or branched unsubstituted or substituted alkyl of from 1 to 8 carbon atoms, straight or branched alkenyl of from 2 to 8 carbon atoms, cycloalkyl of from 3 to 7 carbon atoms, alkoxy of from 1 to 6 carbon atoms, -alkylcycloalkyl, -alkylalkoxy, -alkyl, OH, -alkylphenyl, -alkylphenoxy, -phenyl or substituted phenyl;

$R_4$ is hydrogen or ($C_1$-$C_6$) straight chain or branched unsubstituted or substituted alkyl, or carboxyl;

as well as pharmaceutically acceptable salts thereof.

In other embodiments, the primary amine compound is a compound having the following structural formula:

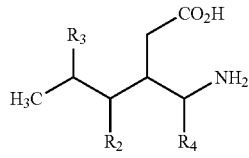

wherein $R_2$ is hydrogen, straight or branched alkyl of from 1 to 6 carbon atoms or phenyl;

$R_3$ is straight or branched alkyl of from 1 to 8 carbon atoms, straight or branched alkenyl of from 2 to 8 carbon atoms, cycloalkyl of from 3 to 7 carbon atoms, alkoxy of from 1 to 6 carbon atoms, -alkylcycloalkyl, -alkylalkoxy, -alkyl OH-alkylphenyl, -alkylphenoxy, -phenyl or substituted phenyl; and $R_4$ is hydrogen, and $R_2$ is straight or branched alkyl of from 1 to 6 carbon atoms or phenyl when $R_3$ is methyl, or a pharmaceutically acceptable salt thereof.

In other embodiments, the primary amine compound can have the following structural formula:

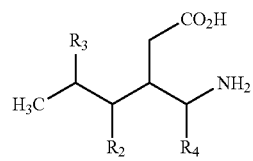

wherein $R_2$ is methyl, $R_3$ is an alkyl, and $R_4$ is a hydrogen, or a pharmaceutically acceptable salt thereof;

Specific examples of compounds of above noted formulas are selected from: 3-Aminomethyl-5-methylhexanoic acid; 3-Aminomethyl-5-methylheptanoic acid; 3-Aminomethyl-5-methyl-octanoic acid; 3-Aminomethyl-5-methyl-nonanoic acid; 3-Aminomethyl-5-methyl-decanoic acid; 3-Aminomethyl-5-methyl-undecanoic acid; 3-Aminomethyl-5-methyl-dodecanoic acid; 3-Aminomethyl-5-methyl-tridecanoic acid; 3-Aminomethyl-5-cyclopropyl-hexanoic acid; 3-Aminomethyl-5-cyclobutyl-hexanoic acid; 3-Aminomethyl-5-cyclopentyl-hexanoic acid; 3-Aminomethyl-5-cyclohexyl-hexanoic acid; 3-Aminomethyl-5-trifluoromethyl-hexanoic acid; 3-Aminomethyl-5-phenyl-hexanoic acid; 3-Aminomethyl-5-(2-chlorophenyl)-hexanoic acid; 3-Aminomethyl-5-(3-chlorophenyl)-hexanoic acid; 3-Aminomethyl-5-(4-chlorophenyl)-hexanoic acid; 3-Aminomethyl-5-(2-methoxyphenyl)-hexanoic acid; 3-Aminomethyl-5-(3-methoxyphenyl)-hexanoic acid; 3-Aminomethyl-5-(4-methoxyphenyl)-hexanoic acid; 3-Aminomethyl-5-(phenylmethyl)-hexanoic acid; (S)-3-(Aminomethyl)-5-methylhexanoic acid; (R)-3-(Aminomethyl)-5-methylhexanoic acid; (3R,4S)-3-Aminomethyl-4,5-dimethyl-hexanoic acid; 3-Aminomethyl-4,5-dimethyl-hexanoic acid; (3R,4S)-3-Aminomethyl-4,5-dimethyl-hexanoic acid MP; (3S,4S)-3-Aminomethyl-4,5-dimethyl-hexanoic acid; (3R,4R)-3-Aminomethyl-4,5-dimethyl-hexanoic acid MP; 3-Aminomethyl-4-isopropyl-hexanoic acid; 3-Aminomethyl-4-isopropyl-heptanoic acid; 3-Aminomethyl-4-isopropyl-octanoic acid; 3-Aminomethyl-4-isopropyl-nonanoic acid; 3-Aminomethyl-4-isopropyl-decanoic acid; 3-Aminomethyl-4-phenyl-5-methyl-hexanoic acid; (3S,5S)-3-Aminomethyl-5-methoxy-hexanoic acid; (3S,5S)-3-Aminomethyl-5-ethoxy-hexanoic acid; (3S,5S)-3-Aminomethyl-5-propoxy-hexanoic acid; (3S,5S)-3-Aminomethyl-5-isopropoxy-hexanoic acid; (3S,5S)-3-Aminomethyl-5-tert-butoxy-hexanoic acid; (3S,5S)-3-Aminomethyl-5-fluoromethoxy-hexanoic acid; (3S,5S)-3-Aminomethyl-5-(2-fluoro-ethoxy)-hexanoic acid; (3S,5S)-3-Aminomethyl-5-(3,3,3-trifluoro-propoxy)-hexanoic acid; (3S,5S)-3-Aminomethyl-5-phenoxy-hexanoic acid; (3S,5S)-3-Aminomethyl-5-(4-chloro-phenoxy)-hexanoic acid; (3S,5S)-3-Aminomethyl-5-(3-chloro-phenoxy)-hexanoic acid; (3S,5S)-3-Aminomethyl-5-(2-chloro-phenoxy)-hexanoic acid; (3S,5S)-3-Aminomethyl-5-(4-fluoro-phenoxy)-hexanoic acid; (3S,5S)-3-Aminomethyl-5-(3-fluoro-phenoxy)-hexanoic acid; (3S,5S)-3-Aminomethyl-5-(2-fluoro-phenoxy)-hexanoic acid; (3S,5S)-3-Aminomethyl-5-(4-methoxy-phenoxy)-hexanoic acid; (3S,5S)-3-Aminomethyl-5-(3-methoxy-phenoxy)-hexanoic acid; (3S,5S)-3-Aminomethyl-5-(2-methoxy-phenoxy)-hexanoic acid; (3S,5S)-3-Aminomethyl-5-(4-nitro-phenoxy)-hexanoic acid; (3S,5S)-3-Aminomethyl-5-(3-nitro-phenoxy)-hexanoic acid; (3S,5S)-3-Aminomethyl-5-(2-nitro-phenoxy)-hexanoic acid; (3S,5S)-3-Aminomethyl-6-hydroxy-5-methyl-hexanoic acid; (3S,5S)-3-Aminomethyl-6-methoxy-5-methyl-hexanoic acid; (3S,5S)-3-Aminomethyl-6-ethoxy-5-methyl-hexanoic acid; (3S,5S)-3-Aminomethyl-5-methyl-6-propoxy-hexanoic acid; (3S,5S)-3-Aminomethyl-6-isopropoxy-5-methyl-hexanoic acid; (3S,5S)-3-Aminomethyl-6-tert-butoxy-5-methyl-hexanoic acid; (3S,5S)-3-Aminomethyl-6-fluoromethoxy-5-methyl-hexanoic acid; (3S,5S)-3-Aminomethyl-6-(2-fluoro-ethoxy)-5-methyl-hexanoic acid; (3S,5S)-3-Aminomethyl-5-methyl-6-(3,3,3-trifluoro-propoxy)-hexanoic acid; (3S,5S)-3-Aminomethyl-5-methyl-6-phenoxy-hexanoic acid; (3S,5S)-3-Aminomethyl-6-(4-chloro-phenoxy)-5-methyl-hexanoic acid; (3S,5S)-3-Aminomethyl-6-(3-chloro-phenoxy)-5-methyl-hexanoic acid; (3S,5S)-3-Aminomethyl-6-(2-chloro-phenoxy)-5-methyl-hexanoic acid; (3S,5S)-3-Aminomethyl-6-(4-fluoro-phenoxy)-5-methyl-hexanoic acid; (3S,5S)-3-Aminomethyl-6-(3-fluoro-phenoxy)-5-methyl-hexanoic acid; (3S,5S)-3-Aminomethyl-6-(2-fluoro-phenoxy)-5-methyl-hexanoic acid; (3S,5S)-3-Aminomethyl-6-(4-methoxy-phenoxy)-5-methyl-hexanoic acid; (3S,5S)-3-Aminomethyl-6-(3-methoxy-phenoxy)-5-methyl-hexanoic acid; (3S,5S)-3-Aminomethyl-6-(2-methoxy-phenoxy)-5-methyl-hexanoic acid; (3S,5S)-3-Aminomethyl-5-methyl 6-(4-trifluoromethyl-phenoxy)-hexanoic acid; (3S,5S)-3-Aminomethyl-5-methyl 6-(3-trifluoromethyl-phenoxy)-hexanoic acid; (3S,5S)-3-Aminomethyl-5-methyl 6-(2-trifluoromethyl-phenoxy)-hexanoic acid; (3S,5S)-3-Aminomethyl-5-methyl 6-(4-nitro-phenoxy)-hexanoic acid; (3S,5S)-3-Aminomethyl-5-methyl 6-(3-nitro-phenoxy)-hexanoic acid; (3S,5S)-3-Aminomethyl-5-methyl 6-(2-nitro-phenoxy)-hexanoic acid; (3S,5S)-3-Aminomethyl-6-benzyloxy-5-methyl-hexanoic acid; (3S,5S)-3-Aminomethyl-7-hydroxy-5-methyl-heptanoic acid; (3S,5S)-3-Aminomethyl-7-methoxy-5-methyl-heptanoic acid; (3S,5S)-3-Aminomethyl-7-ethoxy-5-methyl-heptanoic acid; (3S,5S)-3-Aminomethyl-5-methyl-7-propoxy-heptanoic acid; (3S,5S)-3-Aminomethyl-7-isopropoxy-5-methyl-heptanoic acid; (3S,5S)-3-Aminomethyl-7-tert-butoxy-5-methyl-heptanoic acid; (3S,5S)-3-Aminomethyl-7-fluoromethoxy-5-methyl-heptanoic acid; (3S,5S)-3-Aminomethyl-7-(2-fluoro-ethoxy)-5-methyl-heptanoic acid; (3S,5S)-3-Aminomethyl-5-methyl-7-(3,3,3-trifluoro-propoxy)-heptanoi-c acid; (3S,5S)-3-Aminomethyl-7-benzyloxy-5-methyl-heptanoic acid; (3S,5S)-3-Aminomethyl-5-methyl-7-phenoxy-heptanoic acid; (3S,5S)-3-Aminomethyl-7-(4-chloro-phenoxy)-5-methyl-heptanoic acid; (3S,5S)-3-Aminomethyl-7-(3-chloro-phenoxy)-5-methyl-heptanoic acid; (3S,5S)-3-Aminomethyl-7-(2-chloro-phenoxy)-5-methyl-heptanoic acid; (3S,5S)-3-Aminomethyl-7-(4-fluoro-phenoxy)-5-methyl-heptanoic acid; (3S,5S)-3-Aminomethyl-7-(3-fluoro-phenoxy)-5-methyl-heptanoic acid; (3S,5S)-3-Aminomethyl-7-(2-fluoro-phenoxy)-5-methyl-heptanoic acid; (3S,5S)-3-Aminomethyl-7-(4-methoxy-phenoxy)-5-methyl-heptanoic acid; (3S,5S)-3-Aminomethyl-7-(3-methoxy-phenoxy)-5-methyl-heptanoic acid; (3S,5S)-3-Aminomethyl-7-(2-methoxy-phenoxy)-5-methyl-heptanoic acid; (3S,5S)-3-Aminomethyl-5-methyl-7-(4-trifluoromethyl-phenoxy)-heptan-oic acid; (3S,5S)-3-Aminomethyl-5-methyl-7-(3-trifluoromethyl-phenoxy)-heptan-oic acid; (3S,5S)-3-Aminomethyl-5-methyl-7-(2-trifluoromethyl-phenoxy)-heptan-oic acid; (3S,5S)-3-Aminomethyl-5-methyl-7-(4-nitro-phenoxy)-heptanoic acid; (3S,5S)-3-Aminomethyl-5-methyl-7-(3-nitro-phenoxy)-heptanoic acid; (3S,5S)-3-Aminomethyl-5-methyl-7-(2-nitro-phenoxy)-heptanoic acid; (3S,5S)-3-Aminomethyl-5-methyl-6-phenyl-hexanoic acid; (3S,5S)-3-Aminomethyl-6-(4-chloro-phenyl)-5-methyl-hexanoic acid; (3S,5S)-3-Aminomethyl-6-(3-chloro-phenyl)-5-methyl-hexanoic acid; (3S,5S)-3-Aminomethyl-6-(2-chloro-phenyl)-5-methyl-hexanoic acid; (3S,5S)-3-Aminomethyl-6-(4-methoxy-phenyl)-5-methyl-hexanoic acid; (3S,5S)-3-Aminomethyl-6-(3-methoxy-phenyl)-5-methyl-hexanoic acid; (3S,5S)-3-Aminomethyl-6-(2-methoxy-phenyl)-5-methyl-hexanoic acid; (3S,5S)-3-Aminomethyl-6-(4-fluoro-phenyl)-5-methyl-hexanoic acid; (3S,5S)-3-Aminomethyl-6-(3-fluoro-phenyl)-5-methyl-hexanoic acid; (3S,5S)-3-Aminomethyl-6-(2-fluoro-phenyl)-5-methyl-hexanoic acid; (3S,5R)-3-Aminomethyl-5-methyl-7-phenyl-heptanoic acid; (3S,5R)-3-Aminomethyl-7-(4-chloro-phenyl)-5-methyl-heptanoic acid; (3S,5R)-3-Aminomethyl-7-(3-chloro-phenyl)-5-methyl-heptanoic acid; (3S,5R)-3-Aminomethyl-7-(2-chloro-phenyl)-5-methyl-heptanoic acid; (3S,5R)-3-Aminomethyl-7-(4-methoxy-phenyl)-5-methyl-heptanoic acid; (3S,5R)-3-Aminomethyl-7-(3-methoxy-phenyl)-5-methyl-heptanoic acid; (3S,5R)-3-Aminomethyl-7-(2-methoxy-phenyl)-5-methyl-heptanoic acid; (3S,5R)-3-Aminomethyl-7-(4-fluoro-phenyl)-5-methyl-heptanoic acid; (3S,5R)-3-Aminomethyl-7-(3-fluoro-phenyl)-5-methyl-heptanoic acid; (3S,5R)-3-Aminomethyl-7-(2-fluoro-phenyl)-5-methyl-heptanoic acid; (3S,5R)-3-Aminomethyl-5-methyl-oct-7-enoic acid; (3S,5R)-3-Aminomethyl-5-methyl-non-8-enoic acid; (E)-(3S,5S)-3-Aminomethyl-5-methyl-oct-6-enoic acid; (Z)-(3S,5S)-3-Aminomethyl-5-methyl-oct-6-enoic acid; (Z)-(3S,5S)-3-Aminomethyl-5-methyl-non-6-enoic acid; (E)-(3S,5S)-3-Aminomethyl-5-methyl-non-6-enoic acid; (E)-(3S,5R)-3-Aminomethyl-5-methyl-non-7-enoic acid; (Z)-(3S,5R)-3-Aminomethyl-5-methyl-non-7-enoic acid; (Z)-(3S,5R)-3-Aminomethyl-5-methyl-dec-7-enoic acid; (E)-(3S,5R)-3-Aminomethyl-5-methyl-undec-7-enoic acid; (3S,5S)-3-Aminomethyl-5,6,6-trimethyl-heptanoic acid; (3S,5S)-3-Aminomethyl-5,6-dimethyl-heptanoic acid; (3S,5S)-3-Aminomethyl-5-cyclopropyl-hexanoic acid; (3S,5S)-3-Aminomethyl-5-cyclobutyl-hexanoic acid; (3S,5S)-3-Aminomethyl-5-cyclopentyl-hexanoic acid; (3S,5S)-3-Aminomethyl-5-cyclohexyl-hexanoic acid; (3S,5R)-3-Aminomethyl-5-methyl-heptanoic acid; (3S,5R)-3-Aminomethyl-5-methyl-octanoic acid; (3S,5R)-3-Aminomethyl-5-methyl-nonanoic acid; (3S,5R)-3-Aminomethyl-5-methyl-decanoic acid; (3S,5R)-3-Aminomethyl-5-methyl-undecanoic acid; (3S,5R)-3-Aminomethyl-5-methyl-dodecanoic acid; (3S,5R)-3-Aminomethyl-5,9-dimethyl-decanoic acid; (3S,5R)-3-Aminomethyl-5,7-dimethyl-octanoic acid; (3S,5R)-3-Aminomethyl-5,8-dimethyl-nonanoic acid; (3S,5R)-3-Aminomethyl-6-cyclopropyl-5-methyl-hexanoic acid; (3S,5R)-3-Aminomethyl-6-cyclobutyl-5-methyl-hexanoic acid; (3S,5R)-3-Aminomethyl-6-cyclopentyl-5-methyl-hexanoic acid; (3S,5R)-3-Aminomethyl-6-cyclohexyl-5-methyl-hexanoic acid; (3S,5R)-3-Aminomethyl-7-cyclopropyl-5-methyl-heptanoic acid; (3S,5R)-3-Aminomethyl-7-cyclobutyl-5-methyl-heptanoic acid; (3S,5R)-3-Aminomethyl-7-cyclopentyl-5-methyl-heptanoic acid; (3S,5R)-3-Aminomethyl-7-cyclohexyl-5-methyl-heptanoic acid; (3S,5R)-3-Aminomethyl-8-cyclopropyl-5-methyl-octanoic acid; (3S,5R)-3-Aminomethyl-8-cyclobutyl-5-methyl-octanoic acid; (3S,5R)-3-Aminomethyl-8-cyclopentyl-5-methyl-octanoic acid; (3S,5R)-3-Aminomethyl-8-cyclohexyl-5-methyl-octanoic acid; (3S,5S)-3-Aminomethyl-6-fluoro-5-methyl-hexanoic acid; (3S,5S)-3-Aminomethyl-7-fluoro-5-methyl-heptanoic acid; (3S,5R)-3-Aminomethyl-8-fluoro-5-methyl-octanoic acid; (3S,5R)-3-Aminomethyl-9-fluoro-5-methyl-nonanoic acid; (3S,5S)-3-Aminomethyl-7,7,7-trifluoro-5-methyl-heptanoic acid; (3S,5R)-3-Aminomethyl-8,8,8-trifluoro-5-methyl-octanoic acid; (3S,5R)-3-Aminomethyl-5-methyl-8-phenyl-octanoic acid; (3S,5S)-3-Aminomethyl-5-methyl-6-phenyl-hexanoic acid; (3S,5R)-3-Aminomethyl-5-methyl-7-phenyl-heptanoic acid; and pharmaceutically acceptable salts thereof. Methods of synthesizing the above noted compounds are described in PCT Patent Application No. WO 00/76958, which is incorporated herein by reference in its entirety.

In other embodiments, the primary amine compound can comprise at least one of (S)-3-(Aminomethyl)-5-methyl-hexanoic acid or (R)-3-(Aminomethyl)-5-methylhexanoic acid. In still other embodiments, the primary amine compound can include a mixture of (S)-3-(Aminomethyl)-5-methylhexanoic acid and (R)-3-(Aminomethyl)-5-methyl-hexanoic acid. For example, the primary amine compound can comprise a racemic mixture of (S)-3-(Aminomethyl)-5-methylhexanoic acid and (R)-3-(Aminomethyl)-5-methyl-hexanoic acid. In other examples, the primary amine compound can comprise a mixture of: less than about 50% by weight (S)-3-(Aminomethyl)-5-methylhexanoic acid and greater than about 50% by weight (R)-3-(Aminomethyl)-5-methylhexanoic acid, less than about 25% by weight (S)-3-(Aminomethyl)-5-methylhexanoic acid and greater than about 75% by weight (R)-3-(Aminomethyl)-5-methyl-hexanoic acid, less than about 10% by weight (S)-(Aminomethyl)-5-methylhexanoic acid and greater than about 90% by weight (R)-3-(Aminomethyl)-5-methylhexanoic acid, less than about 1% by weight (S)-3-(Aminomethyl)-5-methylhexanoic acid and greater than about 99% by weight (R)-3-(Aminomethyl)-5-methylhexanoic acid, greater than about 50% by weight (S)-3-(Aminomethyl)-5-methylhexanoic acid and less than about 50% by weight (R)-3-(Aminomethyl)-5-methylhexanoic acid, greater than about 75% by weight (S)-3-(Aminomethyl)-5-methyl-hexanoic acid and less than about 25% by weight (R)-3-(Aminomethyl)-5-methylhexanoic acid, greater than about 90% by weight (S)-3-(Aminomethyl)-5-methylhexanoic acid and less than about 10% by weight (R)-3-(Aminomethyl)-5-methylhexanoic acid, or greater than about 99% by weight (S)-3-(Aminomethyl)-5-methylhexanoic acid and less than about 1% by weight (R)-3-(Aminomethyl)-5-methylhexanoic acid.

In a still further embodiment, the primary amine compound can consist essentially of or consist of (S)-3-(Aminomethyl)-5-methylhexanoic acid. In yet another embodiment, the primary amine compound can consist essentially of or consist of (R)-3-(Aminomethyl)-5-methylhexanoic acid.

In some embodiments, the primary amine compound is a compound having the following structural formula:

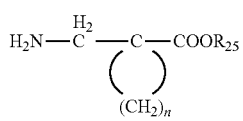

wherein $R_{25}$ is hydrogen or a lower alkyl, such as a $(C_1-C_6)$ straight chain or branched unsubstituted or substituted alkyl, n is 4, 5, or 6 and pharmaceutically acceptable salts thereof. Compounds having the above noted structural formula and methods of forming such compounds are described in U.S. Pat. No. 4,024,175, which is incorporated by reference in its entirety.

In some embodiments, the primary amine compound is a compound having the following structural formula:

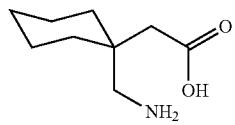

as well as pharmaceutically acceptable salts thereof. A primary compound having this structural formula is also referred to as gabapentin and is sold under the trade name Neurontin.

In another embodiment, the primary amine compound can have the following structural formula:

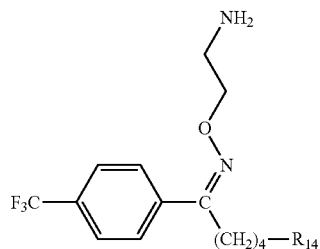

wherein $R_{14}$ is a methoxymethyl or ethoxymethyl groups. Methods of synthesizing the above noted compounds are described in U.S. Pat. No. 4,085,225, which is herein incorporated by reference in its entirety.

In a further embodiment, the primary amine compound can have the following structural formula:

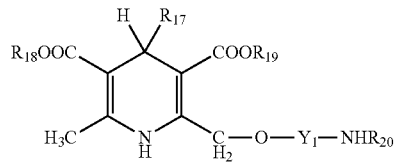

wherein $R_{17}$ is 2-chlorophenyl, 2-fluorophenyl, 2-methoxyphenyl, 3-chlorophenyl, 2-chloro-3-hydroxyphenyl, 2-chloro-6-fluorophenyl, unsubstituted phenyl or 2,3-dichlorophenyl; $R_{18}$ is preferably $CH_3$; $R_{19}$ is $C_2H_5$; $R_{20}$ is H or $CH_3$; and $Y_1$ is $(CH_2)_2$ or $CH_2CH(CH_3)$. Methods of synthesizing the above noted compounds are described in U.S. Pat. No. 4,572,909, which is herein incorporated by reference in its entirety.

In a further embodiment, the primary amine compound can have the following structural formula:

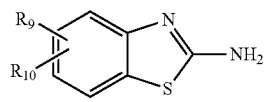

wherein $R_9$ and $R_{10}$ are hydrogen, straight or branched alkyl of from one to six carbon atoms, lower alkylaryl, alkenyl, phenyl, $CF_3$, lower alkoxy, lower alkylthio, lower alkylsulphonyl, $CF_3$ O at the six position, halogen, nitro, $NR_{11}R_{12}$, $R_{11}CONR_{11}$, or CN.

Examples of compounds having the above noted structure are: 2-aminobenzothiazole, 2-amino-6-methylbenzothiazole, 2-amino-4-methylbenzothiazole, 2-amino-6-trifluoromethylbenzothiazole, 2-amino-4-trifluoromethylbenzothiazole, 2-amino-5-trifluoromethylbenzothiazole, 2-amino-6-trifluoromethoxybenzothiazole, 2-amino-6-ethoxybenzothiazole, 2-amino-6-nitrobenzothiazole, 2-amino-4-methoxybenzothiazole, 2-amino-5-methoxybenzothiazole, 2-amino-4,6-dimethylbenzothiazole, 2-amino-6-bromobenzothiazole, 2-amino-6-chlorobenzothiazole, 2-amino-4-chlorobenzothiazole, 2-amino-6-fluoromethylbenzothiazole, 2-amino-naptho[1,2-d]thiazole, 2-ethylaminobenzothiazole, 2-[[2-(1-methyl-2-pyrrolidinyl)ethyl]amino]-benzothiazole, 2-amino-6-methylsulphonylbenzothiazole, 2-amino-4,6-difluorobenzothiazole, 2-amino-6-methylthiobenzothiazole, 2-benzylaminobenzothiazole, and pharmaceutically acceptable salts thereof. Methods of synthesizing the above noted compounds are described in U.S. Pat. No. 4,826,860, which is herein incorporated by reference in its entirety.

In some embodiments, the primary amine compound can be selected using an in vitro assay that measures the ability of the primary amine compound to improve viability of RPE cells treated with retinal. By way of example, primary amine compounds administered to RPE cells treated with retinal that improved the viability of the RPE cells at least 15% compared to untreated cells are selected from the group consisting of:

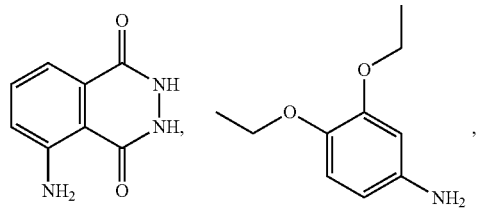

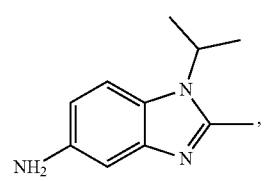

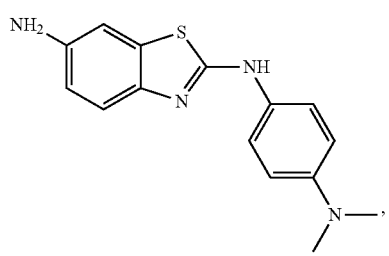

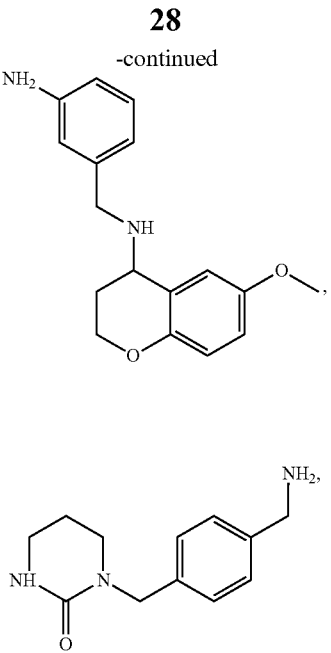

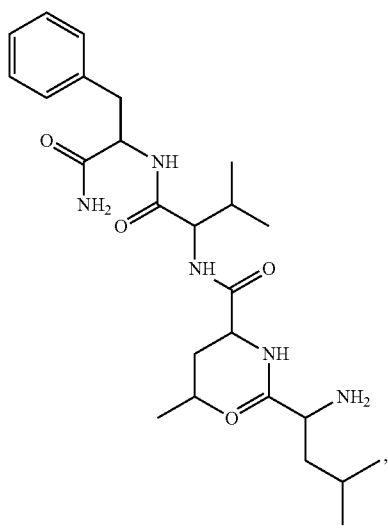

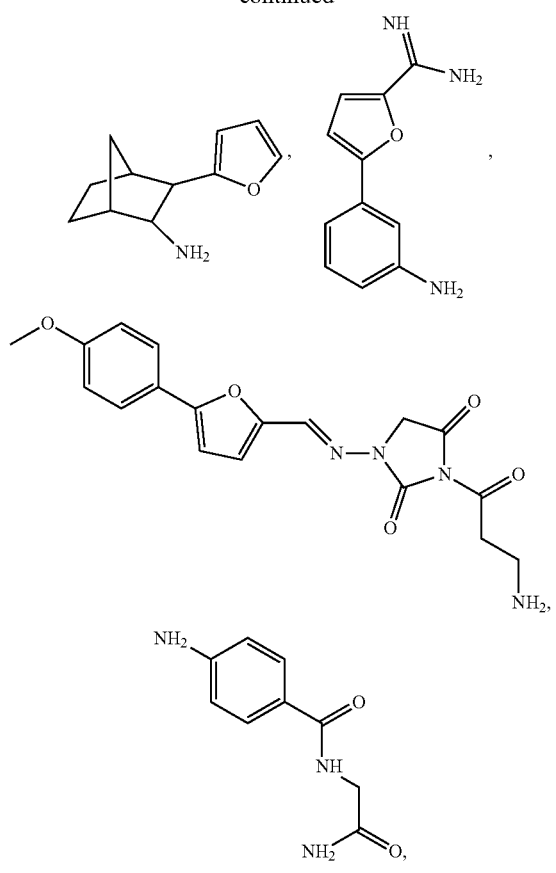
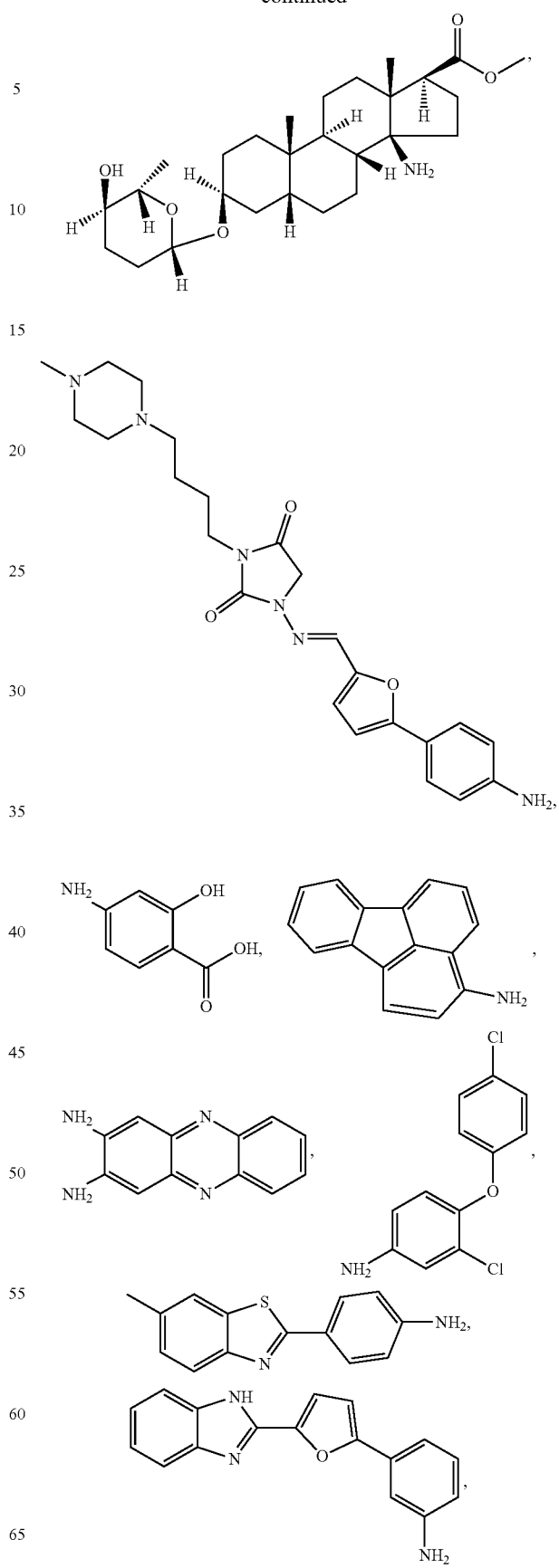

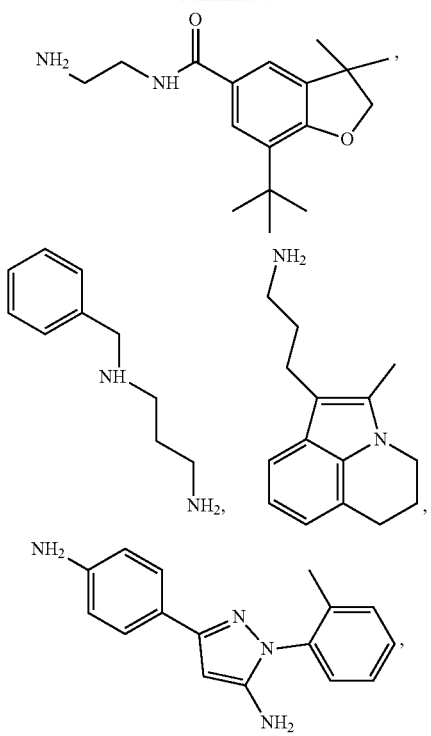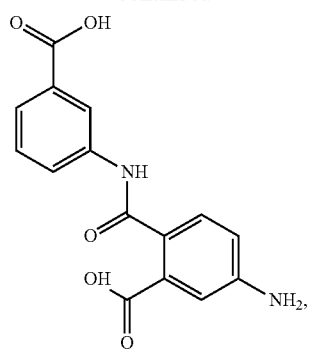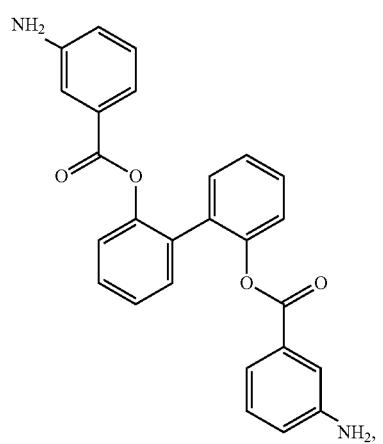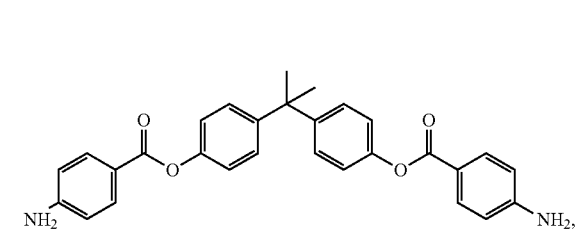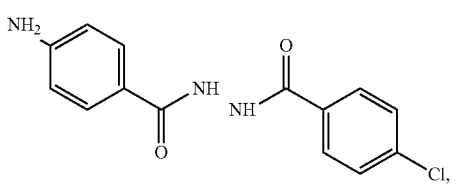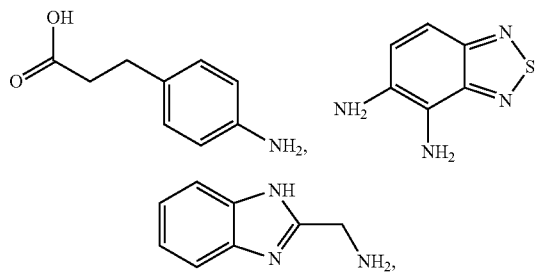

33
-continued
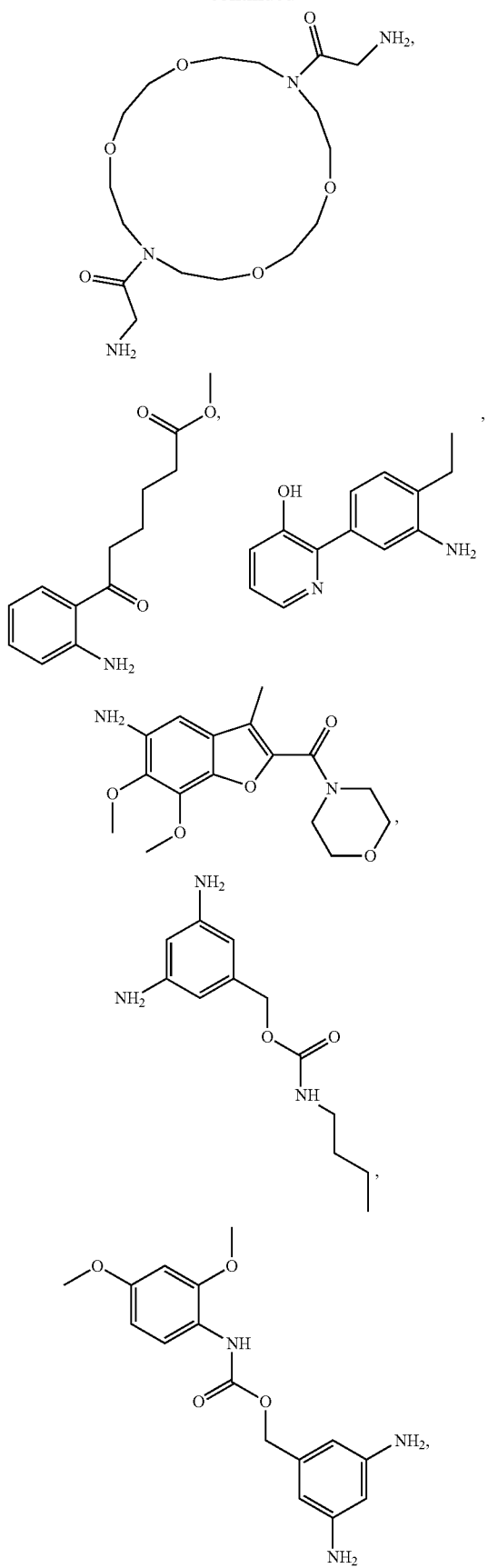 [SMILES: NCC(=O)N1CCOCCOCCN(C(=O)CN)CCOCCOCC1 ; COC(=O)CCCCC(=O)c1ccccc1N ; CCc1ccc(-c2ncccc2O)cc1N ; COc1c(N)cc2c(C)c(C(=O)N3CCOCC3)oc2c1OC ; CCCCNC(=O)OCc1cc(N)cc(N)c1 ; COc1ccc(NC(=O)OCc2cc(N)cc(N)c2)c(OC)c1]
34
-continued
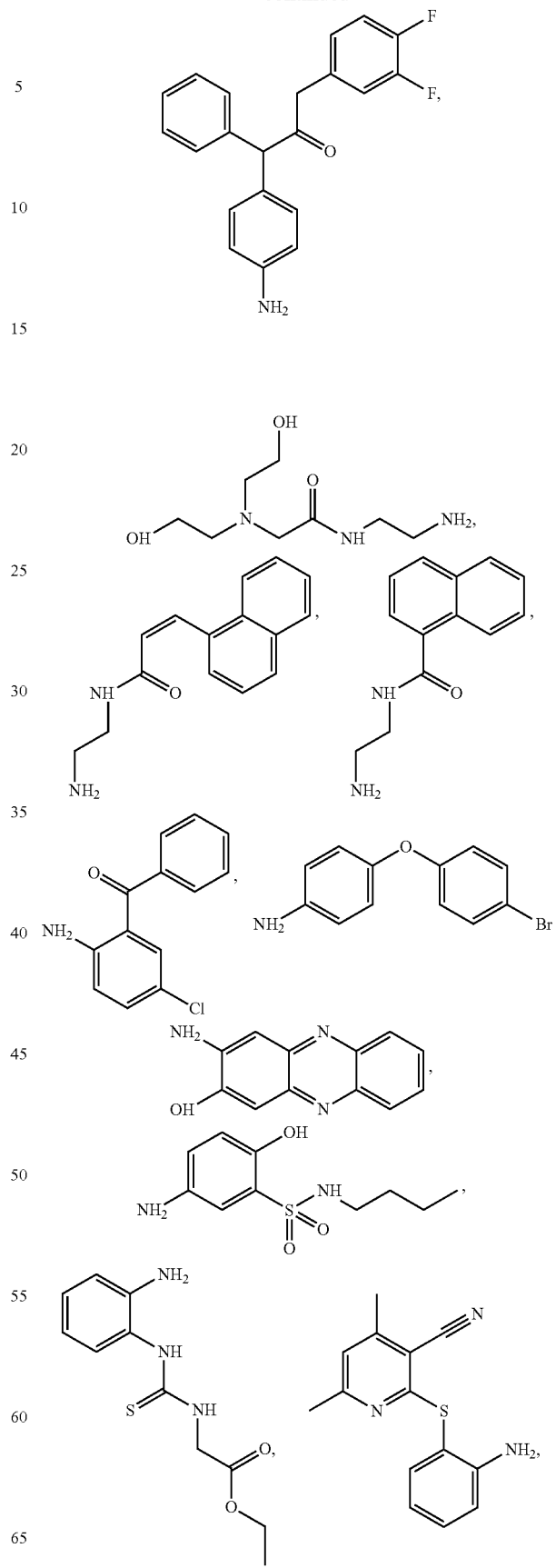

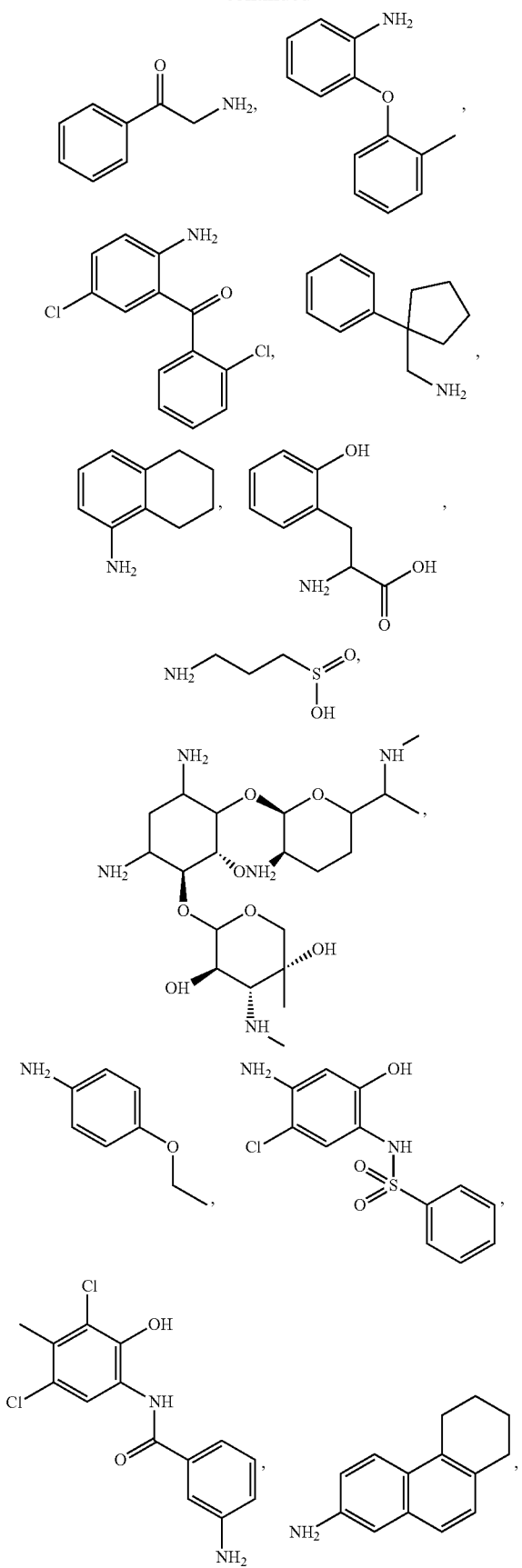
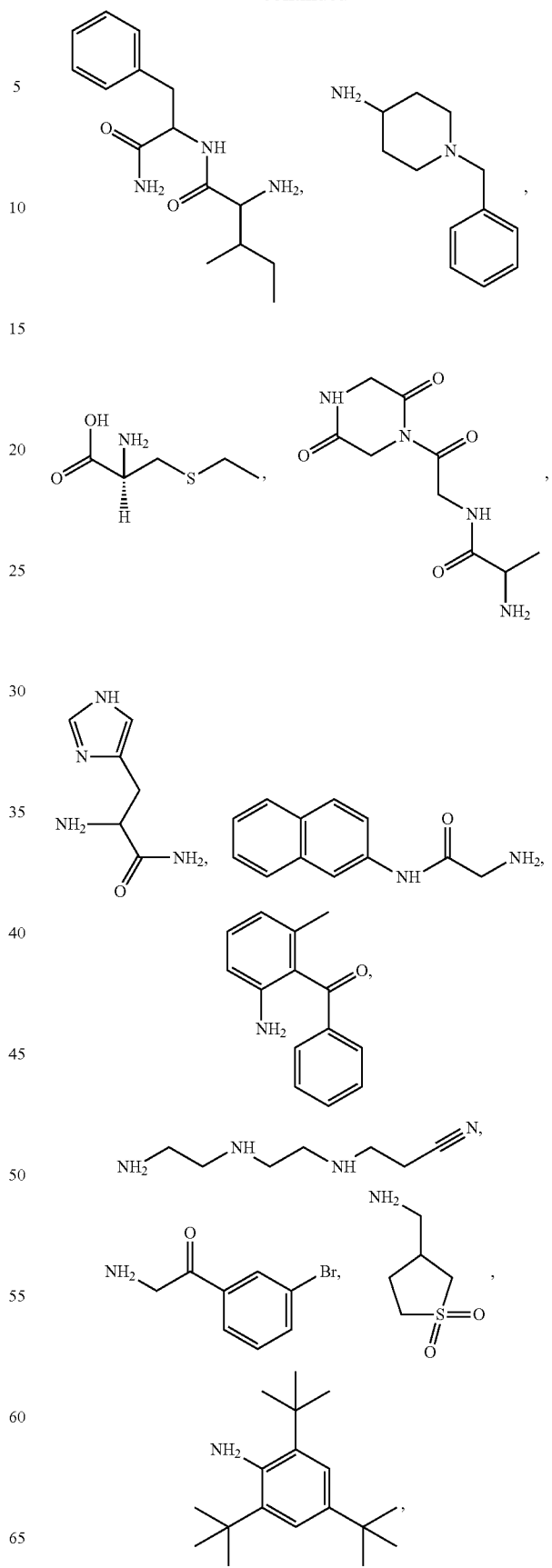

37
-continued
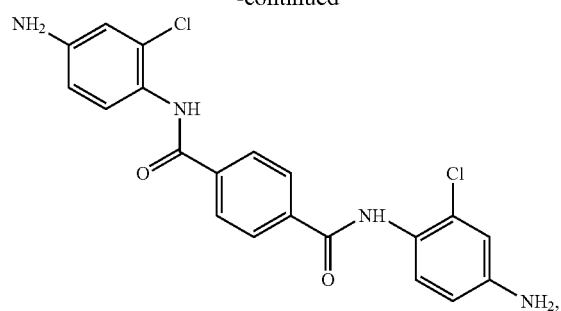
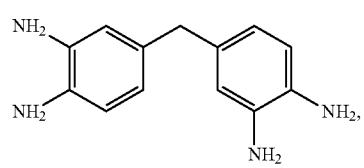
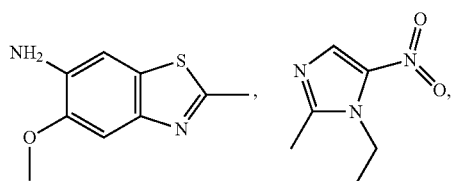
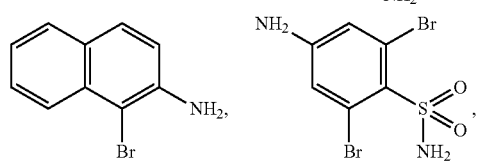
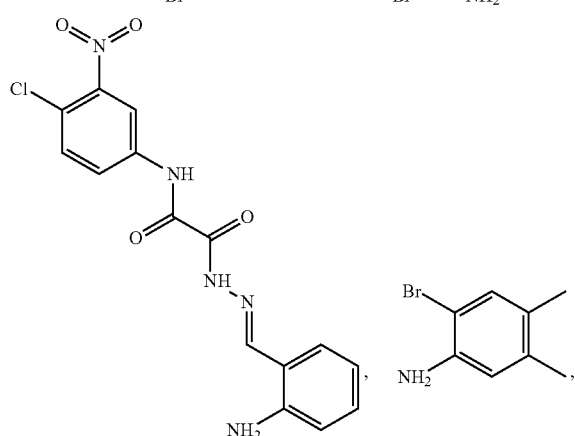
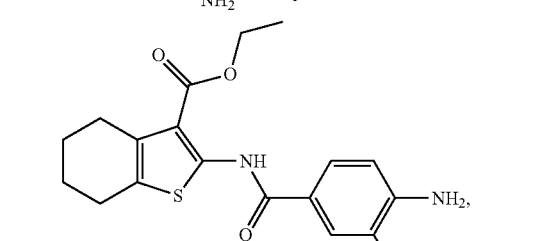
38
-continued
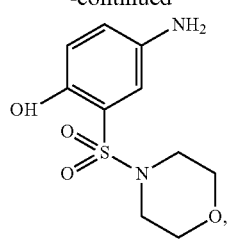
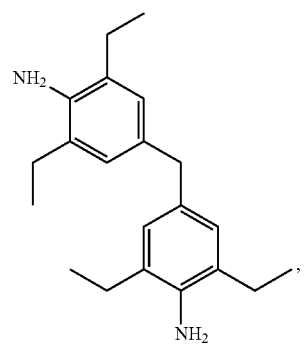
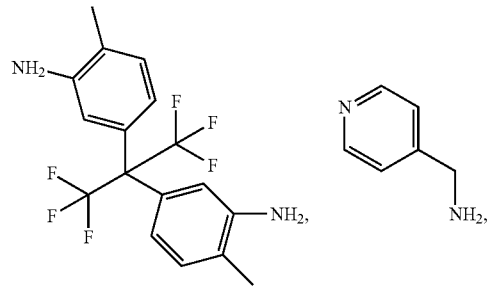
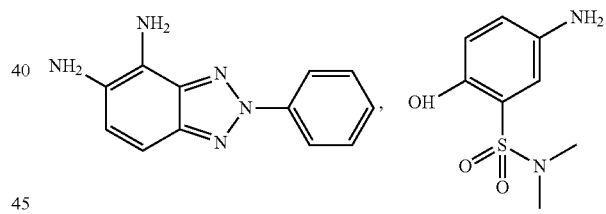
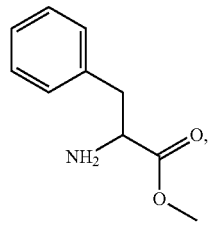
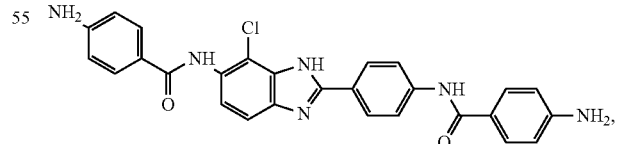
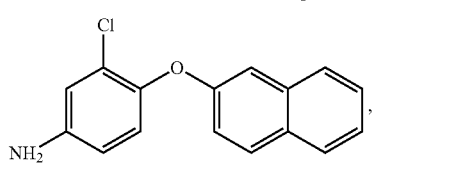

-continued
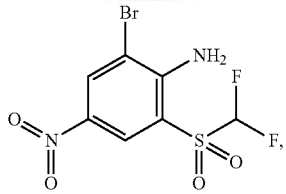
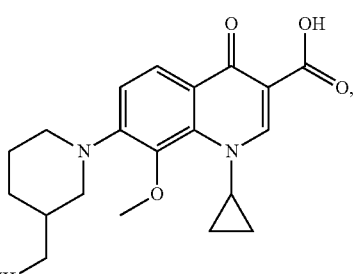
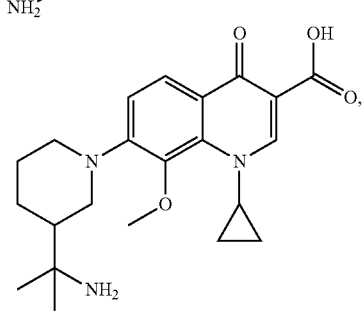
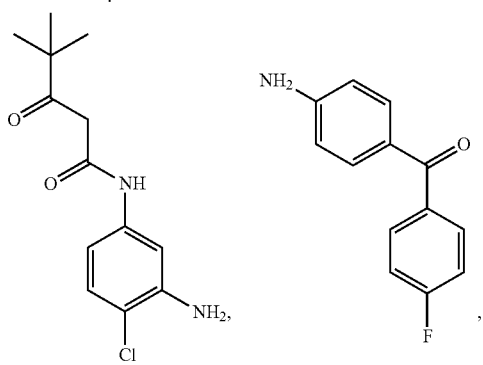
-continued
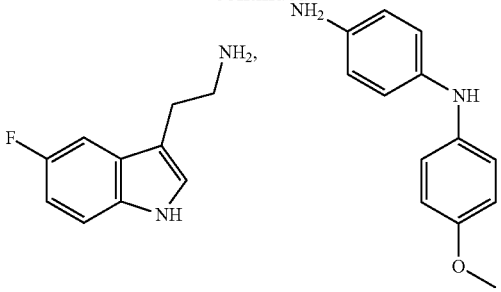
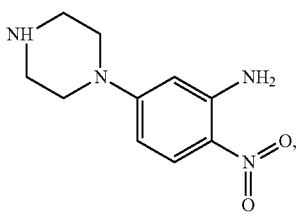
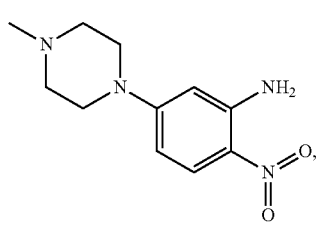
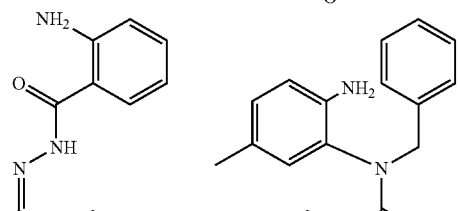
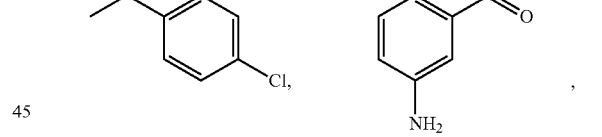
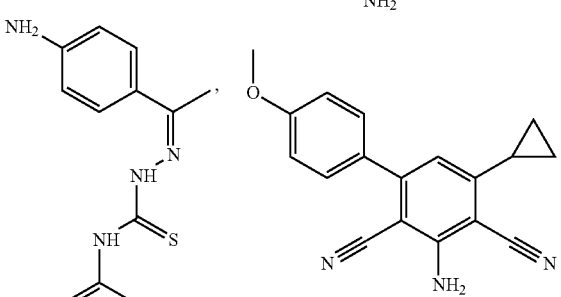
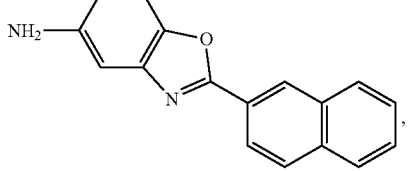

-continued
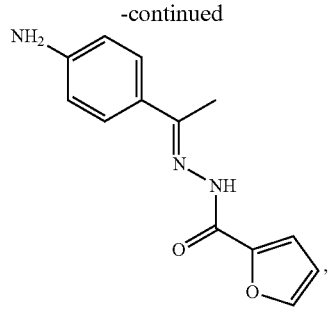
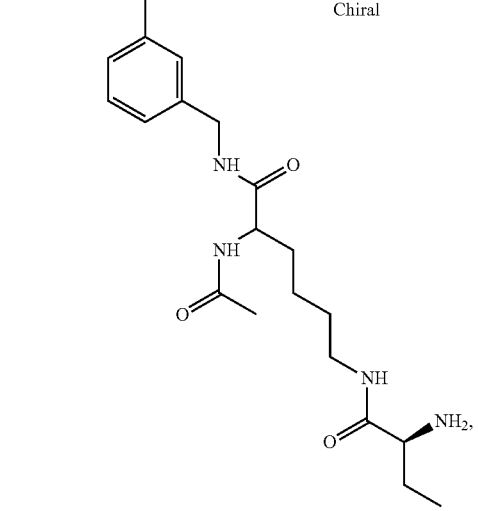
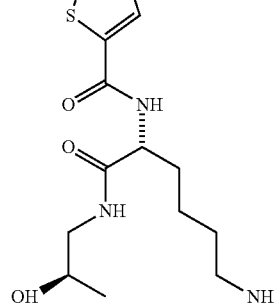
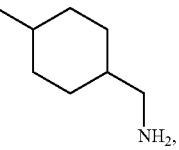
-continued
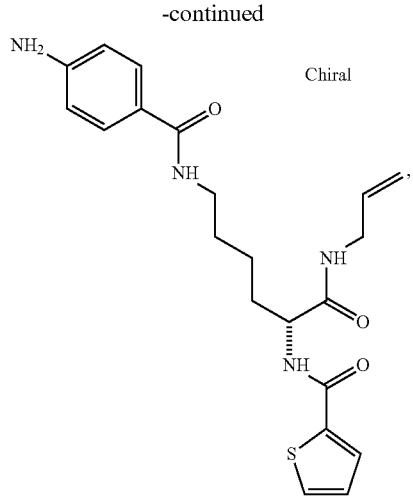
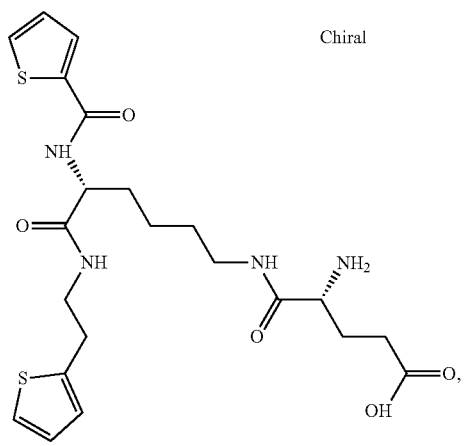
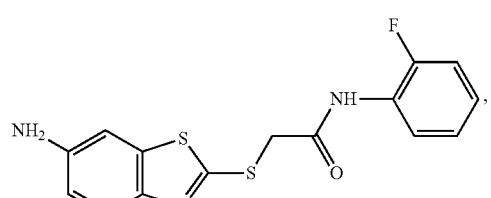
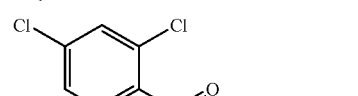
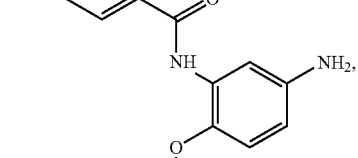
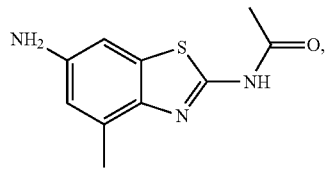

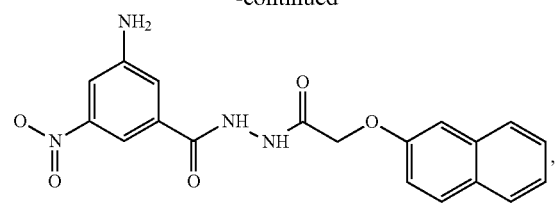
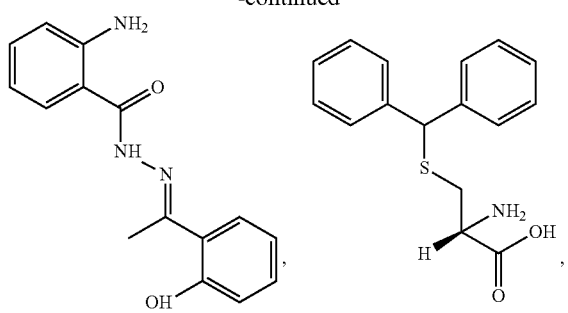
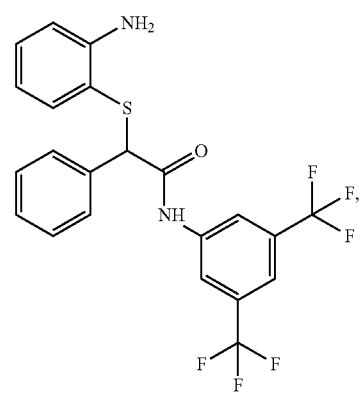
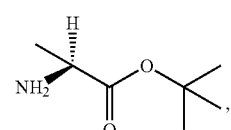
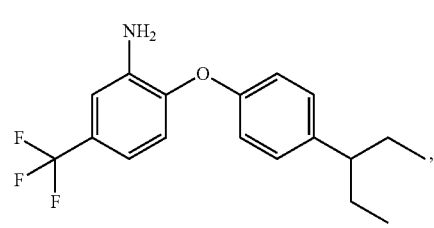
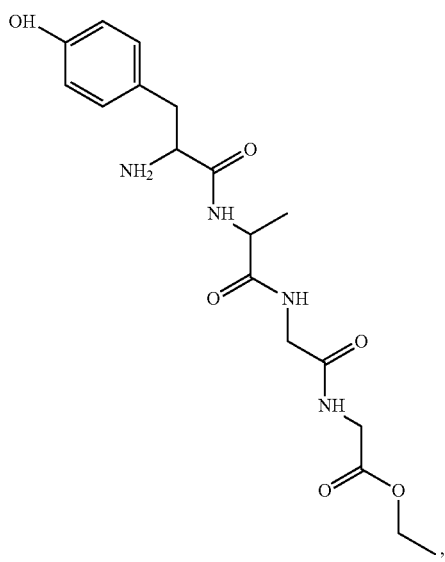
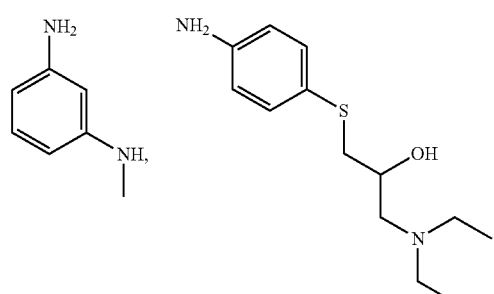
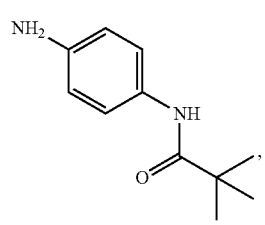
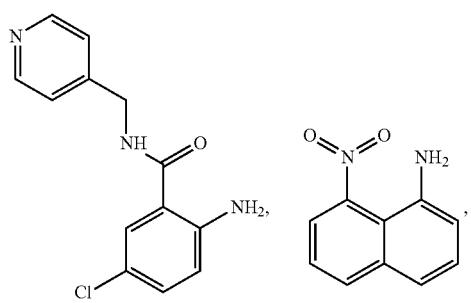
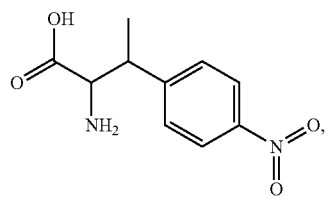
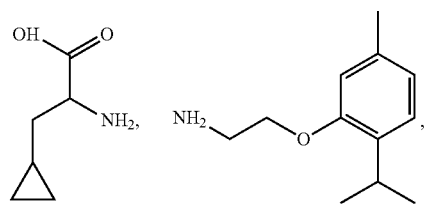
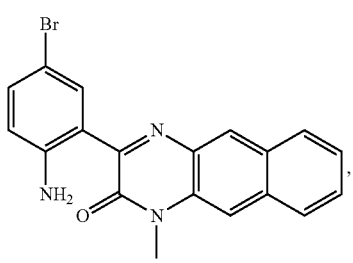

45
-continued
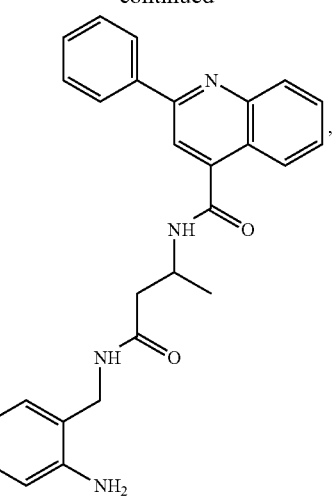
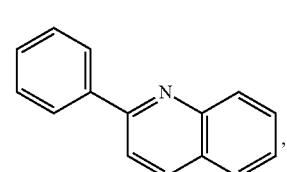
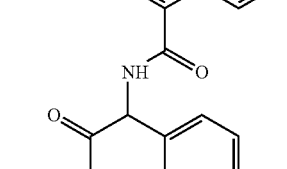
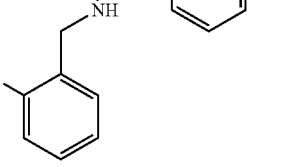
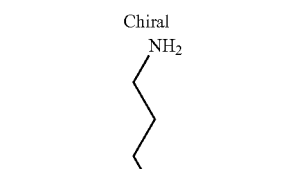
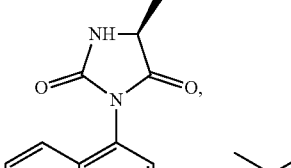
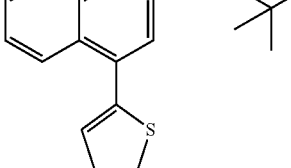
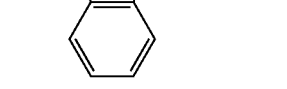
46
-continued
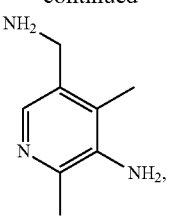
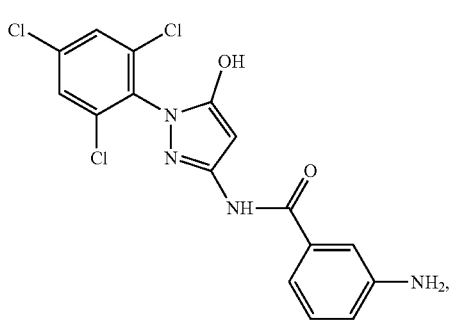
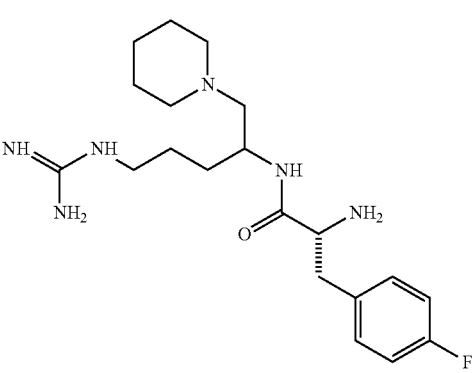
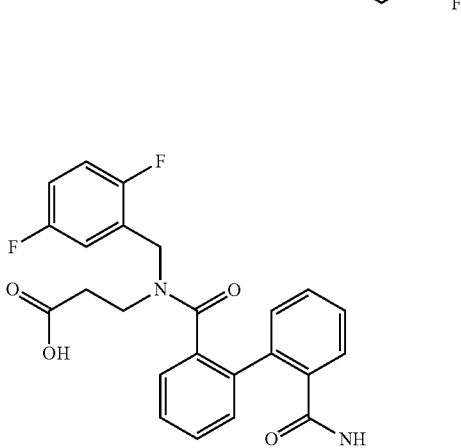
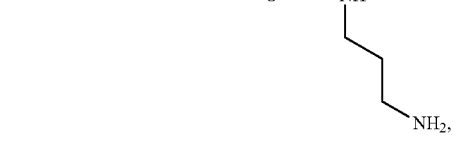

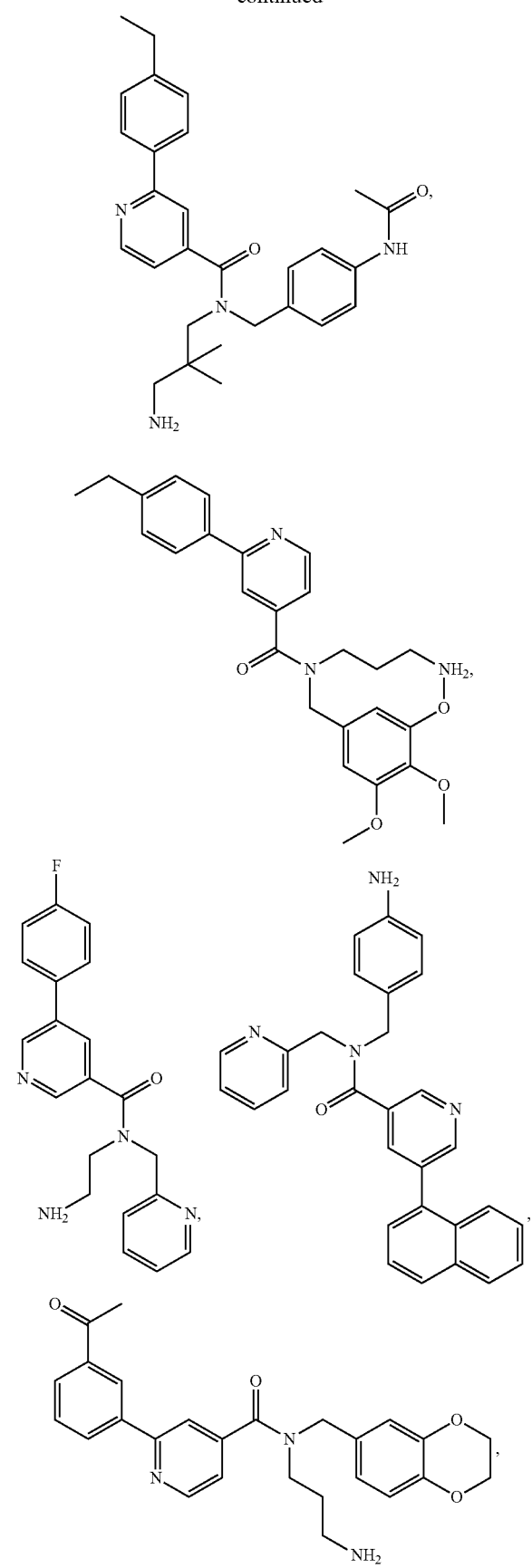
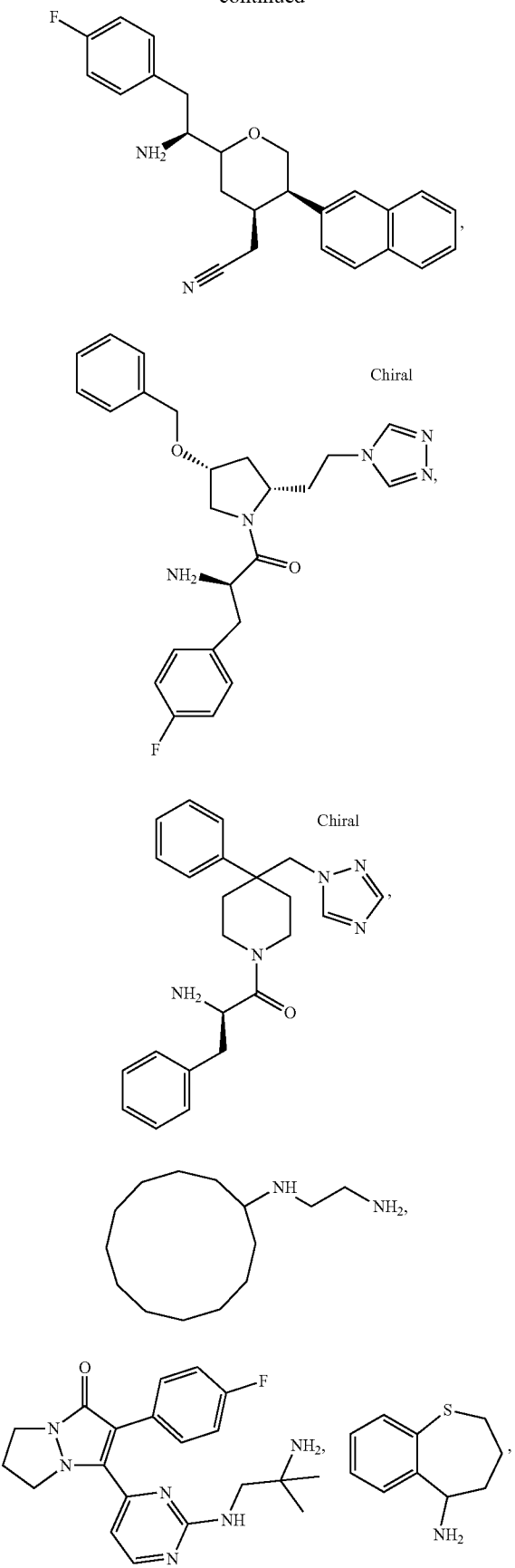

-continued

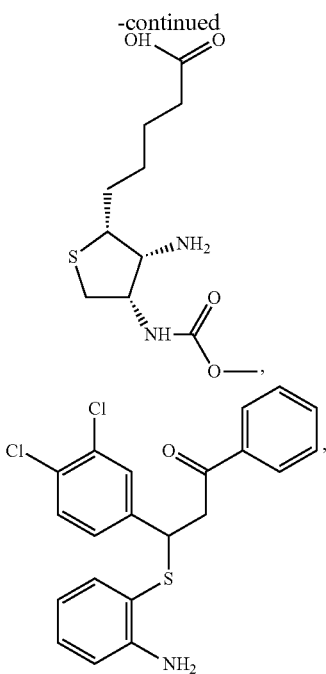

and pharmaceutically acceptable salts thereof.

In another example, primary amine compounds administered to RPE cells treated with retinal that improved the viability of the RPE cells at least 15% compared to untreated cells are selected from the group consisting of: 5-amino-2,3-dihydrophthalazine-1,4-dione, 3,4-diethoxyaniline, 1-isopropyl-2-methyl-benzimidazol-5-amine, N2-(4-dimethylaminophenyl)-1,3-benzothiazole-2,6-diamine, N-[(3-aminophenyl)methyl]-6-methoxy-chroman-4-amine, 1-[[4-(aminomethyl)phenyl]methyl]hexahydropyrimidin-2-one, 1-(2,4-diphenylpyrimidin-5-yl)ethanamine, 3-(5-aminopentyl)-1-[(E)-(5-nitro-2-furyl)methyleneamino]imidazolidine-2,4-dione, 2-amino-N-[1-[[1-[(2-amino-1-benzyl-2-oxo-ethyl)carbamoyl]-2-methyl-propyl]carbamoyl]-3-methyl-butyl]-4-methyl-pentanamide, 2-(2-furyl)bicyclo[2.2.1]hept-5-en-3-amine, 5-(3-aminophenyl)furan-2-carboxamidine, 3-(3-aminopropanoyl)-1-[(E)-[5-(4-methoxyphenyl)-2-furyl]methyleneamino]imidazolidine-2,4-dione, 4-amino-N-(2-amino-2-oxo-ethyl)benzamide, 4-amino-N-[2-oxo-2-[(2-oxooxazolidin-3-yl)amino]ethyl]benzamide, (1S,2S,4R)-2-amino-4-isopropenyl-1-methyl-cyclohexanol, 2-amino-4-benzyl-phenol, (3S,5R,8R,9S,10S,13R,14S)-14-amino-3-hydroxy-10,13-dimethyl-1,2,3,4,5,6,7,8,9,11,12,15,16,17-tetradecahydrocyclopenta[a]phenanthrene-17-carboxylic acid, methyl (3S,5R,8R,9S,10S,13R,14S)-14-amino-3-[(2S,5R)-5-hydroxy-6-methyl-tetrahydropyran-2-yl]oxy-10,13-dimethyl-1,2,3,4,5,6,7,8,9,11,12,15,16,17-tetradecahydrocyclopenta[a]phenanthrene-17-carboxylate, 1-[(E)-[5-(4-aminophenyl)-2-furyl]methyleneamino]-3-[4-(4-methylpiperazin-1-yl)butyl]imidazolidine-2,4-dione, 4-amino-2-hydroxy-benzoic acid, fluoranthen-3-amine, phenazine-2,3-diamine, 3-chloro-4-(4-chlorophenoxy)aniline, 4-(6-methyl-1,3-benzothiazol-2-yl)aniline, 3-[5-(1H-benzimidazol-2-yl)-2-furyl]aniline, N-(2-aminoethyl)-7-tert-butyl-3,3-dimethyl-2H-benzofuran-5-carboxamide, N'-benzylpropane-1,3-diamine, 5,6-dihydro-2-methyl-4H-pyrrolo[3,2,1-ij]quinoline-1-propanamine, 5-(4-aminophenyl)-2-(o-tolyl)pyrazol-3-amine, (2,3-dimethyl-1H-indol-5-yl)methanamine, 2,4-dimethyl-6-nitro-aniline, methyl 2-amino-4,5-dimethoxy-benzoate, 2-(5-propyl-1H-indol-3-yl)ethanamine, 2-(7-methoxy-5-nitro-1H-indol-3-yl)ethanamine, 5-amino-2-[(4-carboxyphenyl)carbamoyl]benzoic acid, 5-amino-2-[(3-carboxyphenyl)carbamoyl]benzoic acid, [2-[2-(3-aminobenzoyl)oxyphenyl]phenyl] 3-aminobenzoate, [4-[1-[4-(4-aminobenzoyl)oxyphenyl]-1-methyl-ethyl]phenyl] 4-aminobenzoate, 4-amino-N'-(4-chlorobenzoyl)benzohydrazide, 3-(4-aminophenyl)propanoic acid, 2,1,3-benzothiadiazole-4,5-diamine, 1H-benzimidazol-2-ylmethanamine, 2-amino-1-[16-(2-aminoacetyl)-1,4,10,13-tetraoxa-7,16-diazacyclooctadec-7-yl]ethanone, methyl 6-(2-aminophenyl)-6-oxo-hexanoate, 2-(3-amino-4-ethyl-phenyl)pyridin-3-ol, (5-amino-6,7-dimethoxy-3-methyl-benzofuran-2-yl)-morpholino-methanone, (3,5-diaminophenyl)methyl N-butyl-carbamate, (3,5-diaminophenyl)methyl N-(2,4-dimethoxyphenyl)carbamate, 1-(4-aminophenyl)-3-(3,4-difluorophenyl)-1-phenyl-propan-2-one, N-(2-aminoethyl)-2-[bis(2-hydroxyethyl)amino]acetamide, (Z)—N-(2-aminoethyl)-3-(1-naphthyl)prop-2-enamide, N-(2-aminoethyl)naphthalene-1-carboxamide, (2-amino-5-chloro-phenyl)-phenyl-methanone, 4-(4-bromophenoxy)aniline, 3-aminophenazin-2-ol, 5-amino-N-butyl-2-hydroxy-benzenesulfonamide, ethyl 2-[(2-aminophenyl)carbamothioylamino]acetate, 2-(2-aminophenyl) sulfanyl-4,6-dimethyl-pyridine-3-carbonitrile, 2-amino-1-phenyl-ethanone, 2-(2-methylphenoxy)aniline, (2-amino-5-chloro-phenyl)-(2-chlorophenyl)methanone, (1-phenylcyclopentyl)methanamine, tetralin-5-amine, 2-amino-3-(2-hydroxyphenyl)propanoic acid, 3-aminopropane-1-sulfinic acid, (3R,4R,5R)-2-[(1S,2S)-4,6-diamino-3-[(2R,3R)-3-amino-6-[1-(methylamino)ethyl]tetrahydropyran-2-yl]oxy-2-hydroxy-cyclohexoxy]-5-methyl-4-(methylamino)tetrahydropyran-3,5-diol, 4-ethoxyaniline, N-(4-amino-5-chloro-2-hydroxy-phenyl)benzenesulfonamide, 3-amino-N-(3,5-dichloro-2-hydroxy-4-methyl-phenyl)benzamide, 5,6,7,8-tetrahydrophenanthren-2-amine, 2-amino-N-(2-amino-1-benzyl-2-oxo-ethyl)-3-methyl-pentanamide, 1-benzylpiperidin-4-amine, (2R)-2-amino-3-ethylsulfanylpropanoic acid, 2-amino-N-[2-(2,5-dioxopiperazin-1-yl)-2-oxo-ethyl]propanamide, 2-amino-3-(1H-imidazol-4-yl)propanamide, 2-amino-N-(2-naphthyl)acetamide, (2-amino-6-methyl-phenyl)-phenyl-methanone, 3-[2-(2-aminoethylamino)ethylamino]propanenitrile, 2-amino-1-(3-bromophenyl)ethanone, (1,1-dioxothiolan-3-yl)methanamine, 2,4,6-tritert-butylaniline, N1,N4-bis(4-amino-2-chloro-phenyl)terephthalamide, 4-[(3,4-diaminophenyl)methyl]benzene-1,2-diamine, 5-methoxy-2-methyl-1,3-benzothiazol-6-amine, 2-(2-methyl-5-nitro-imidazol-1-yl)ethanamine, 1-bromonaphthalen-2-amine, 4-amino-2,6-dibromo-benzenesulfonamide, N'-[(E)-(2-aminophenyl)methyleneamino]-N-(4-chloro-3-nitro-phenyl)oxamide, 2-bromo-4,5-dimethyl-aniline, ethyl 2-[(4-amino-3-nitro-benzoyl)amino]-4,5,6,7-tetrahydrobenzothiophene-3-carboxylate, 4-amino-2-morpholinosulfonyl-phenol, 4-[(4-amino-3,5-diethyl-phenyl)methyl]-2,6-diethyl-aniline, 5-[1-(3-amino-4-methyl-phenyl)-2,2,2-trifluoro-1-(trifluoromethyl)ethyl]-2-methyl-aniline, 4-pyridylmethanamine, 2-phenylbenzotriazole-4,5-diamine, 5-amino-2-hydroxy-N,N-dimethyl-benzenesulfonamide, methyl 2-amino-3-phenyl-propanoate, 4-amino-N-[4-[6-[(4-aminobenzoyl)amino]-7-chloro-1H-benzimidazol-2-yl]phenyl]benzamide, 3-chloro-4-(2-naphthyloxy)aniline, 2-bromo-6-(difluoromethylsulfonyl)-4-nitro-aniline, 5-(4-aminophenoxy)-2-(1-naphthyl)isoindoline-1,3-dione, 5-(3-aminophenoxy)-2-(1-naphthyl)isoindoline-1,3-dione, 7-[3-(aminomethyl)-1-piperidyl]-1-cyclopropyl-8-methoxy-4-oxo-quinoline-3- carboxylic acid, 7-[3-(1-amino-1-methyl-ethyl)-1-piperidyl]-1-cyclopropyl-8-methoxy-4-oxo-quinoline-3-carboxylic acid, N-(3-amino-4-chloro-phenyl)-4,4-dimethyl-3-oxo-pentanamide, (4-aminophenyl)-(4-fluorophenyl)methanone, 2-(5-fluoro-1H-indol-3-yl) ethanamine, N1-(4-methoxyphenyl)benzene-1,4-diamine, 2-nitro-5-piperazin-1-yl-aniline, 5-(4-methylpiperazin-1-yl)-2-nitro-aniline, 2-amino-N—[(Z)-1-(4-chlorophenyl) ethylideneamino]benzamide, 3-amino-N-(2-amino-5-methyl-phenyl)-N-benzyl-benzamide, 1-[(Z)-1-(4-aminophenyl)ethylideneamino]-3-(m-tolyl)thiourea, 2-amino-4-cyclopropyl-6-(4-methoxyphenyl)benzene-1,3-dicarbonitrile, 2-(2-naphthyl)-1,3-benzoxazol-5-amine, N-[(E)-1-(4-aminophenyl)ethylideneamino]furan-2-carboxamide, 4-(4-aminophenyl)thiazol-2-amine, (2R)-2-acetamido-6-[[(2R)-2-aminobutanoyl]amino]-N-[[3-(trifluoromethyl)phenyl]methyl]hexanamide, (4S)-5-[[(5R)-5-acetamido-6-oxo-6-(propylamino)hexyl]amino]-4-amino-5-oxo-pentanoic acid, N-[(1R)-5-[[4-(aminomethyl)cyclohexanecarbonyl]amino]-1-[[(2R)-2-hydroxypropyl]carbamoyl]pentyl]thiophene-2-carboxamide, N-[(1R)-1-(allylcarbamoyl)-5-[(4-aminobenzoyl)amino]pentyl] thiophene-2-carboxamide, (4S)-4-amino-5-oxo-5-[[(5R)-6-oxo-6-[2-(2-thienyl)ethylamino]-5-(thiophene-2-carbonylamino)hexyl]amino]pentanoic acid, 2-[(6-amino-1,3-benzothiazol-2-yl)sulfanyl]-N-(2-fluorophenyl) acetamide, N-(5-amino-2-methoxy-phenyl)-2,4-dichlorobenzamide, N-(6-amino-4-methyl-1,3-benzothiazol-2-yl) acetamide, 3-amino-N'-[2-(2-naphthyloxy)acetyl]-5-nitro-benzohydrazide, 2-(2-aminophenyl)sulfanyl-N-[3,5-bis(trifluoromethyl)phenyl]-2-phenyl-acetamide, ethyl 2-[[2-[2-[[2-amino-3-(4-hydroxyphenyl)propanoyl]amino] propanoylamino]acetyl]amino]acetate, 2-amino-5-chloro-N-(4-pyridylmethyl)benzamide, 8-nitronaphthalen-1-amine, 2-amino-3-cyclopropyl-propanoic acid, 2-(2-isopropyl-5-methyl-phenoxy)ethanamine, 2-amino-N-[(E)-1-(2-hydroxyphenyl)ethylideneamino]benzamide, (2R)-2-amino-3-benzhydrylsulfanyl-propanoic acid, tert-butyl 2-aminopropanoate, 2-[4-(1-ethylpropyl)phenoxy]-5-(trifluoromethyl)aniline, N1-methylbenzene-1,3-diamine, 1-(4-aminophenyl)sulfanyl-3-(diethylamino)propan-2-ol, N-(4-aminophenyl)-2,2-dimethyl-propanamide, 2-amino-3-(4-nitrophenyl)butanoic acid, 2-(2-amino-5-bromo-phenyl)-4-methyl-benzo[g]quinoxalin-3-one, N-[3-[(2-aminophenyl) methylamino]-1-methyl-3-oxo-propyl]-2-phenyl-quinoline-4-carboxamide, N-[2-[(2-aminophenyl)methylamino]-2-oxo-1-phenyl-ethyl]-2-phenyl-quinoline-4-carboxamide, (5S)-5-(4-aminobutyl)-3-[4-(o-tolyl)phenyl]imidazolidine-2,4-dione, (5S)-5-(4-aminobutyl)-3-[4-(benzothiophen-2-yl)-1-naphthyl]-2-thioxo-imidazolidin-4-one, 2-amino-4,6-ditert-butyl-phenol, 5-(aminomethyl)-2,4-dimethyl-pyridin-3-amine, 3-amino-N-[5-hydroxy-1-(2,4,6-trichlorophenyl) pyrazol-3-yl]benzamide, (2R)-2-amino-3-(4-fluorophenyl)-N-[4-guanidino-1-(1-piperidylmethyl)butyl]propanamide, 3-[[2-[2-(3-aminopropylcarbamoyl)phenyl]benzoyl]-[(2,5-difluorophenyl)methyl]amino]propanoic acid, N-[(4-acetamidophenyl)methyl]-N-(3-amino-2,2-dimethyl-propyl)-2-(4-ethylphenyl)pyridine-4-carboxamide, N-(3-aminopropyl)-2-(4-ethylphenyl)-N-[(3,4,5-trimethoxyphenyl)methyl]pyridine-4-carboxamide, N-(2-aminoethyl)-5-(4-fluorophenyl)-N-(2-pyridylmethyl) pyridine-3-carboxamide, N-[[4-(aminomethyl)phenyl] methyl]-5-(1-naphthyl)-N-(2-pyridylmethyl)pyridine-3-carboxamide, 2-(3-acetylphenyl)-N-(3-aminopropyl)-N-(2,3-dihydro-1,4-benzodioxin-6-ylmethyl)pyridine-4-carboxamide, 2-[(4S,5R)-2-[(1R)-1-amino-2-(4-fluorophenyl)ethyl]-5-(2-naphthyl)tetrahydropyran-4-yl] acetonitrile, (2R)-2-amino-1-[(2S,4R)-4-benzyloxy-2-[2-(1,2,4-triazol-4-yl)ethyl]pyrrolidin-1-yl]-3-(4-fluorophenyl) propan-1-one, (2R)-2-amino-3-phenyl-1-[4-phenyl-4-(1,2,4-triazol-1-ylmethyl)-1-piperidyl]propan-1-one, N'-cyclododecylethane-1,2-diamine, 7-[2-[(2-amino-2-methyl-propyl)amino]pyrimidin-4-yl]-6-(4-fluorophenyl)-2,3-dihydro-1H-pyrazolo[1,2-a]pyrazol-5-one, 2,3,4,5-tetrahydro-1-benzothiepin-5-amine, 5-[(R2R,3R,4S)-3-amino-4-(methoxycarbonylamino)tetrahydrothiophen-2-yl] pentanoic acid, 3-(2-aminophenyl)sulfanyl-3-(3,4-dichlorophenyl)-1-phenyl-propan-1-one, and pharmaceutically acceptable salts thereof.

The primary amine compounds used in methods described herein can be administered to the subject to treat the ocular disorder (e.g., macular degeneration or Stargardt disease, geographic atrophy) using standard delivery methods including, for example, ophthalmic, topical, parenteral, subcutaneous, intravenous, intraarticular, intrathecal, intramuscular, intraperitoneal, intradermal injections, or by transdermal, buccal, oromucosal, oral routes or via inhalation. The particular approach and dosage used for a particular subject depends on several factors including, for example, the general health, weight, and age of the subject. Based on factors such as these, a medical practitioner can select an appropriate approach to treatment.

Treatment according to the method described herein can be altered, stopped, or re-initiated in a subject depending on the status of ocular disorder. Treatment can be carried out as intervals determined to be appropriate by those skilled in the art. For example, the administration can be carried out 1, 2, 3, or 4 times a day. In another embodiment, the primary amine compound can be administered after induction of macular degeneration has occurred.

The treatment methods can include administering to the subject a therapeutically effective amount of the primary amine compound. Determination of a therapeutically effective amount is within the capability of those skilled in the art. The exact formulation, route of administration, and dosage can be chosen by the individual physician in view of the subject's condition.

Formulation of pharmaceutical compounds for use in the modes of administration noted above (and others) are described, for example, in Remington's Pharmaceutical Sciences (18th edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y. U.S.A., 1999.

In one example, the primary amine compound can be provided in an ophthalmic preparation that can be administered to the subject's eye. The ophthalmic preparation can contain the primary amine compound in a pharmaceutically acceptable solution, suspension or ointment. Some variations in concentration will necessarily occur, depending on the particular primary amine compound employed, the condition of the subject to be treated and the like, and the person responsible for treatment will determine the most suitable concentration for the individual subject. The ophthalmic preparation can be in the form of a sterile aqueous solution containing, if desired, additional ingredients, for example, preservatives, buffers, tonicity agents, antioxidants, stabilizers, nonionic wetting or clarifying agents, and viscosity increasing agents.

Examples of preservatives for use in such a solution include benzalkonium chloride, benzethonium chloride, chlorobutanol, thimerosal and the like. Examples of buffers include boric acid, sodium and potassium bicarbonate, sodium and potassium borates, sodium and potassium carbonate, sodium acetate, and sodium biphosphate, in amounts sufficient to maintain the pH at between about pH 6 and about pH 8, and for example, between about pH 7 and about pH 7.5. Examples of tonicity agents are dextran 40, dextran 70, dextrose, glycerin, potassium chloride, propylene glycol, and sodium chloride.

Examples of antioxidants and stabilizers include sodium bisulfite, sodium metabisulfite, sodium thiosulfite, and thiourea. Examples of wetting and clarifying agents include polysorbate 80, polysorbate 20, poloxamer 282 and tyloxapol. Examples of viscosity-increasing agents include gelatin, glycerin, hydroxyethylcellulose, hydroxmethylpropylcellulose, lanolin, methylcellulose, petrolatum, polyethylene glycol, polyvinyl alcohol, polyvinylpyrrolidone, and carboxymethylcellulose. The ophthalmic preparation will be administered topically to the eye of the subject in need of treatment by conventional methods, for example, in the form of drops or by bathing the eye in the ophthalmic solution.

The primary amine compound can also be formulated for topical administration through the skin. "Topical delivery systems" also include transdermal patches containing the ingredient to be administered. Delivery through the skin can further be achieved by iontophoresis or electrotransport, if desired.

Formulations for topical administration to the skin can include, for example, ointments, creams, gels and pastes comprising the primary amine compound in a pharmaceutical acceptable carrier. The formulation of the primary amine compound for topical use includes the preparation of oleaginous or water-soluble ointment bases, as is well known to those in the art. For example, these formulations may include vegetable oils, animal fats, and, for example, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

Subjects affected with or at risk of macular degeneration, which are not readily accessible or suitable for ophthalmic (e.g. eye-drops) and/or topical administration, can be treated by a systemic approach, such as intravenous infusion. For example, the primary amine compound can be administered at a low dosage by continuous intravenous infusion. In another example, in which a patient requires longer-term care, the primary amine compound can be administered intermittently (e.g., every 12-24 hours). In a variation of this approach, the initial or loading dose can be followed by maintenance doses that are less than, (e.g., half) the loading dose or by continuous infusion. The duration of such treatment can be determined by those having skill in the art, based on factors, for example, the severity of the condition and the observation of improvements.

When administering the primary amine compound to the subject by intravenous infusion, devices and equipment (e.g., catheters, such as central or peripheral venous catheters, tubing, drip chambers, flashback bulbs, injection Y sites, stopcocks, and infusion bags) can be used that are compatible with the primary amine compound.

As discussed above, the primary amine compounds may be administered to a subject in order to treat or prevent macular degeneration and other forms of retinal disease whose etiology involves aberrant all-trans-RAL clearance. Other diseases, disorders, or conditions characterized by aberrant all-trans-RAL may be similarly treated.

In one embodiment, a subject is diagnosed as having symptoms of macular degeneration, and then a disclosed compound is administered. In another embodiment, a subject may be identified as being at risk for developing macular degeneration (risk factors include a history of smoking, age, female gender, and family history), and then a disclosed compound is administered. In another embodiment, a subject may have dry AMD in both eye, and then a disclosed compound is administered. In another embodiment, a subject may have wet AMD in one eye but dry AMD in the other eye, and then a disclosed compound is administered. In yet another embodiment, a subject may be diagnosed as having Stargardt disease and then a disclosed compound is administered. In another embodiment, a subject is diagnosed as having symptoms of other forms of retinal disease whose etiology involves aberrant all-trans-RAL clearance, such as geographic atrophy (GA), and then the compound is administered. In another embodiment, a subject may be identified as being at risk for developing other forms of retinal disease whose etiology involves all-trans-RAL clearance, and then the disclosed compound is administered. In some embodiments, a compound is administered prophylactically. In some embodiments, a subject has been diagnosed as having the disease before retinal damage is apparent. In some embodiments, a human subject may know that he or she is in need of the macular generation treatment or prevention.

In some embodiments, a subject may be monitored for the extent of macular degeneration. A subject may be monitored in a variety of ways, such as by eye examination, dilated eye examination, fundoscopic examination, visual acuity test, and/or biopsy. Monitoring can be performed at a variety of times. For example, a subject may be monitored after a compound is administered. The monitoring can occur, for example, one day, one week, two weeks, one month, two months, six months, one year, two years, five years, or any other time period after the first administration of a compound. A subject can be repeatedly monitored. In some embodiments, the dose of a compound may be altered in response to monitoring.

In some embodiments, the disclosed methods may be combined with other methods for treating or preventing macular degeneration or other forms of retinal disease whose etiology involves aberrant all-trans-RAL clearance, such as photodynamic therapy. For example, a patient may be treated with more than one therapy for one or more diseases or disorders. For example, a patient may have one eye afflicted with dry form AMD, which is treated with a compound of the invention, and the other eye afflicted with wet form AMD, which is treated with, e.g., photodynamic therapy.

In yet another embodiment, the primary amine compound described herein can be administered as part of a combinatorial therapy with additional therapeutic agents. The phrase "combinatorial therapy" or "combination therapy" embraces the administration of a primary amine compound, and one or more therapeutic agents as part of a specific treatment regimen intended to provide beneficial effect from the co-action of these therapeutic agents. Administration of these therapeutic agents in combination typically is carried out over a defined period (usually minutes, hours, days or weeks depending upon the combination selected). "Combinatorial therapy" or "combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example by administering to the subject an individual dose having a fixed ratio of each therapeutic agent or in multiple, individual doses for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissue. The therapeutic agents can be administered by the same route or by different routes. The sequence in which the therapeutic agents are administered is not narrowly critical.

The invention is further illustrated by the following example, which is not intended to limit the scope of the claims.

Example 1

Formation of Schiff Base Between Retinal and Selected Amines

We tested 5 FDA approved drugs containing primary amino groups to determine if they react with the aldehyde group of all-trans-RAL to form conjugates (Schiff-base) under the physiological conditions of the eye. The five FDA approved drugs included Potaba, Paser, Seromycin, Cuprimine, and Lyrica.

Formation of conjugates (Schiff-base) between retinal and primary amine compounds containing amino group (putative drugs) is the key mechanism to control all-trans-RAL levels in the retina and prevent retina degeneration. Stability of these conjugates is an important factor that can determine biological activity of the drugs. To standardize conditions of Schiff-base formation all reactions were performed in 90% ethanol in water buffered with 0.1 M phosphate buffer, pH 7.0. Stock solution of retinal was made up freshly in ethanol. Its final concentration was determined spectrophotometrically at 380 nm ($\varepsilon$=42,880). All procedures were carried out in the dark. Schiff base formation was initiated by addition of retinal stock solution to a 2 molar excess of tested amine dissolved in the reaction buffer. The reaction mixture was incubated for 1 h in room temperature.

Steady-state rate of Schiff-base formation was obtained from absorbance changes at 380 and 440 nm (510 nm for aromatic amines) corresponding to free retinal and protonated Schiff base, respectively. To investigate stability of the given retinal conjugates a mixture of HPLC purified Schiff base of selected compound and phosphatidylocholine was dried down in SpeedVac. Then, Schiff-base and lipids were overlaid with 0.1 M phosphate buffer and sonicated immediately to form liposomes. The samples were extracted with hexane following 30 min incubated in room temperature. The breakdown of Schiff-base was monitored by HPLC detection of free retinal extracted from the reaction mixture.

Figure 3:
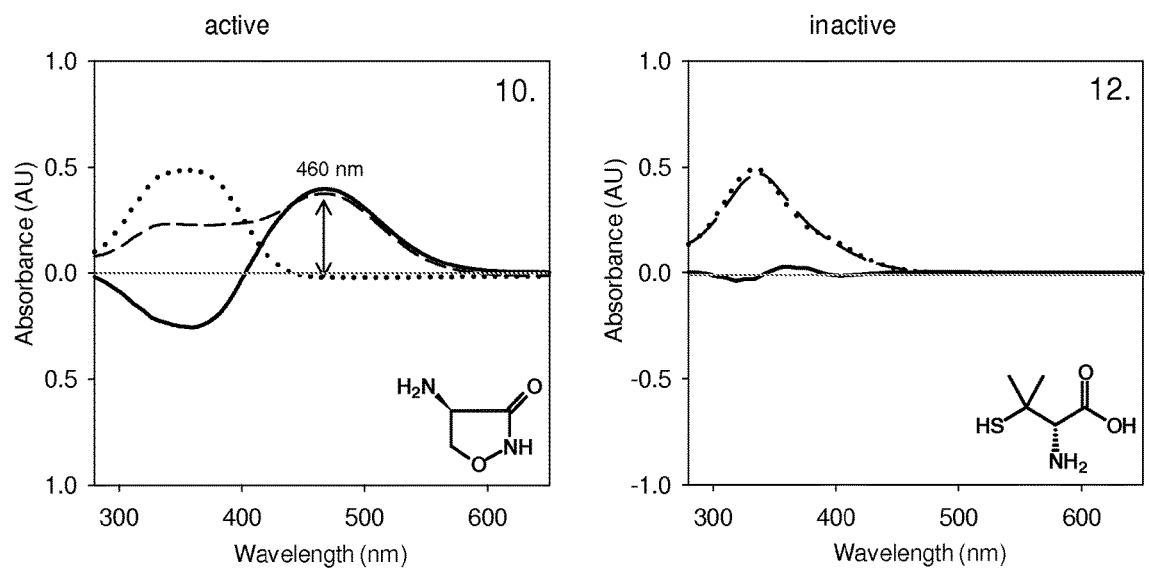
FIGS. 3A-B illustrate UV/Vis spectra for active and inactive primary amine compounds in accordance with an aspect of the application.
Figure 4:
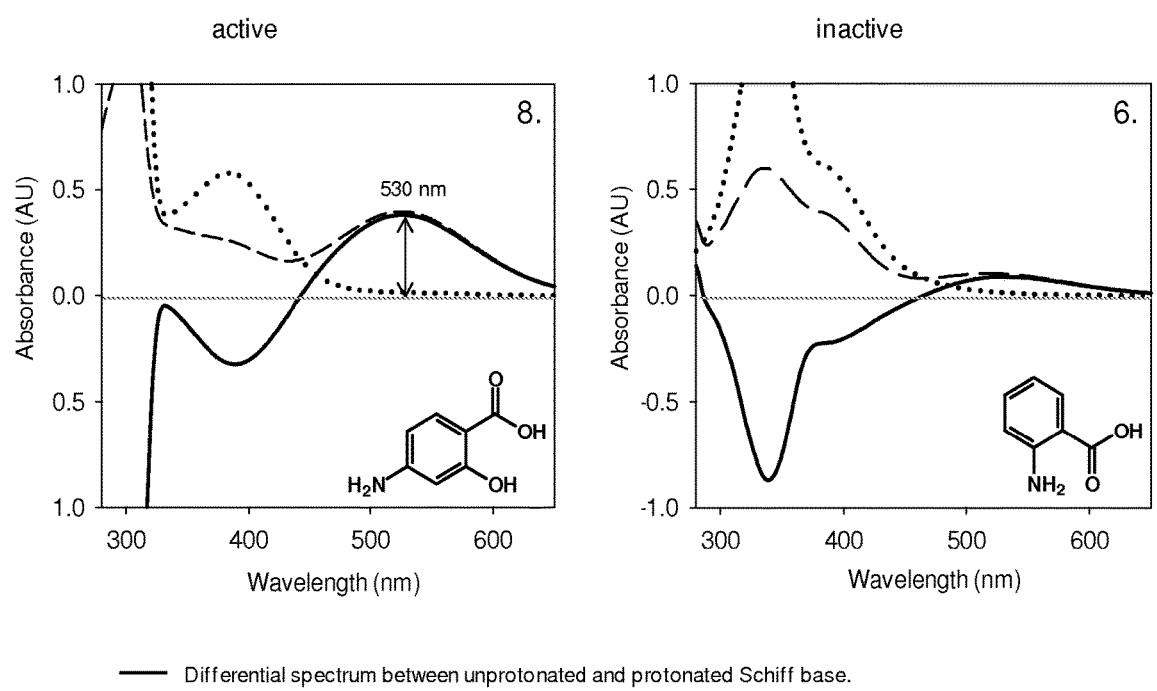
FIGS. 4A-B illustrate UV/Vis spectra for active and inactive primary amine compounds in accordance with an aspect of the application.
Figure 5:
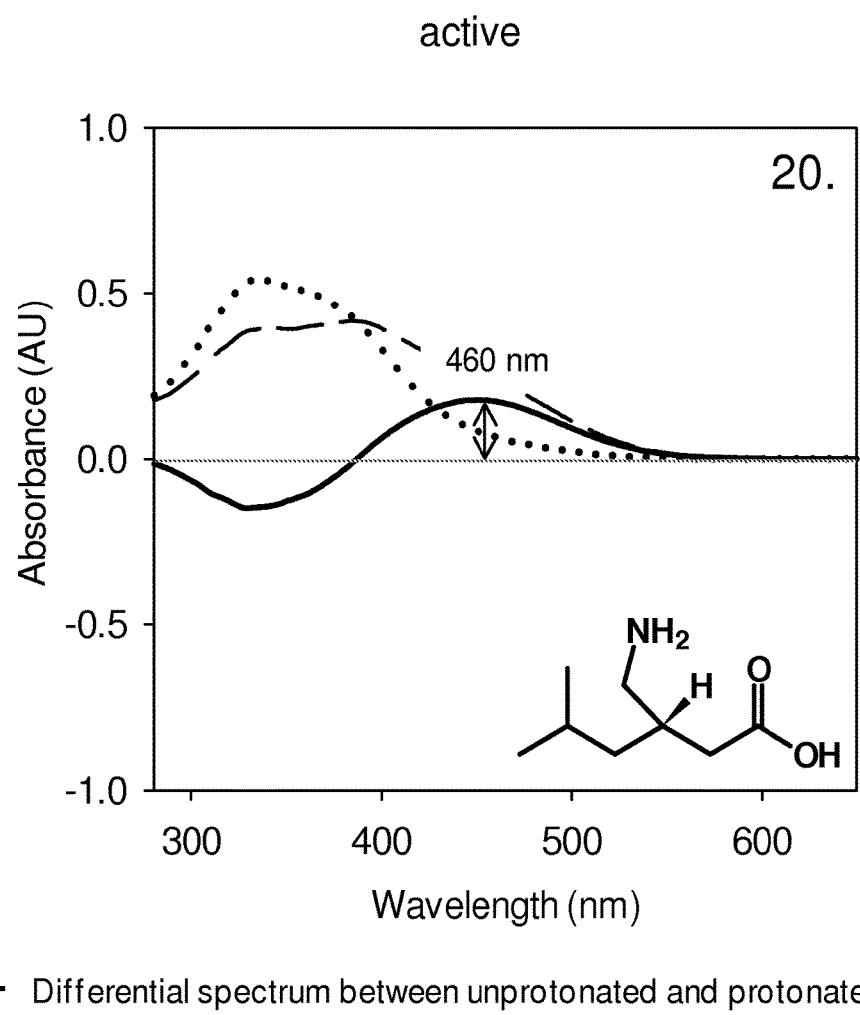
FIG. 5 illustrates UV/Vis spectra for an active primary amine compound in accordance with an aspect of the invention.

FIGS. 3-5 illustrate UV/Vis spectra for the FDA approved drugs. FDA approved drugs that were active readily formed a Schiff base with all-trans-RAL as evidenced by a substantial differential between spectra of unprotonated and protonated Schiff base. Whereas, compounds that were inactive did not readily form a Schiff Base with all-trans-RAL and showed little differential in the spectra. Of the FDA approved drugs tested, Paser, Seromycin, and Lyrica readily formed stable Schiff-bases with all-trans-RAL. In contrast, Potaba and Cuprimine did not readily form stable Schiff-bases with all-trans-RAL.

Example 2

We tested 21 drugs containing primary amino groups to determine if they react with the aldehyde group of all-trans-RAL to reduce its toxic levels in the eye after exposure to light and prevent its condensation into toxic conjugates. The drugs included Flumadine, Nameda, Potaba, Dapsone, Paser, Luvox, Seromycin, Aminohippurate Sodium, Cuprimine, Januvia, Primaxin I.M., Prinivil, Sulfamylon, Exforge, Stalevo, Sodium Diuril, Lyrica ((S)-3-(aminomethyl)-5-methylhexanoic acid), (R)-3-(aminomethyl)-5-methylhexanoic acid), Asacol, Tamiflu, and Rilutek. For these experiments, we used ABCA4$^{-/-}$/RDH8$^{-/-}$ mice as models for Stargardt's disease and AMD. We employed analytical methods for determining the pharmacodynamics and pharmacokinetics of candidate drugs including: HPLC/MS/MS for analysis of retinoids and histological sections and OCT for assessment of retinal pathology. The relative amount of retinoids and their composition strongly correlates with the health status of the retina. FDA approved drugs were determined effective in treating retinal degeneration if upon administration to ABCA4$^{-/-}$/RDH8$^{-/-}$ mice, the mice showed optical coherence tomography score of at least about 2.5 and the drug increased 11-cis-retinal amount at least about 30% in comparison to untreated control animal. Methodologies for performing the analysis on ABCA4$^{-/-}$/RDH8$^{-/-}$ mice is described below.

Animals

Rdh8$^{-/-}$ mice were generated and genotyped as previously described in J. Biol. Chem. 280, 188-18832 (2005). Abca4$^{-/-}$ mice also were generated by standard procedures (Ingenious Targeting, Inc., Stony Brook, N.Y.). The targeting vector was constructed by replacing exon 1 with the neo cassette as described by Cell, 98 13-23 (1999). No Immunoreactivity against ABCA4 was detected in eye extracts from these mice by Immunocytochemistry or Immunoblotting. Abca4$^{-/-}$ mice were maintained with either pigmented 129Sv/Ev or C57BL/6 mixed backgrounds, and their siblings were used for most experiments. Rdh8$^{-/-}$Abca4$^{-/-}$ mice were established by crossbreeding Abca4$^{-/-}$ mice with Rdh8$^{-/-}$ mice. Genotyping or mice was carried out by PCR with primers ABCR1 (5'-gcccagtggtcgatctgtctagc-3')(SEQ ID NO: 1) d ABCR2 (5'-cacaaaggccgctaggaccacg-3') (SEQ ID NO: 2) for wild type (WT) (619 bp) and AO (5'-ccacagcacacatcagcatttctcc-3') (SEQ ID NO: 3) and N1 (5'-tgcgaggccagaggccacttgtgtagc-3') (SEQ ID NO: 4) for targeted deletion (455 bp). PCR products were cloned and sequenced to verify their identities. Rdh8$^{-/-}$Abca4$^{-/-}$ mice were fertile and showed no obvious developmental abnormalities.

Extraction and Hplc Analysis of Non-Polar Retinoids

Figure 6:
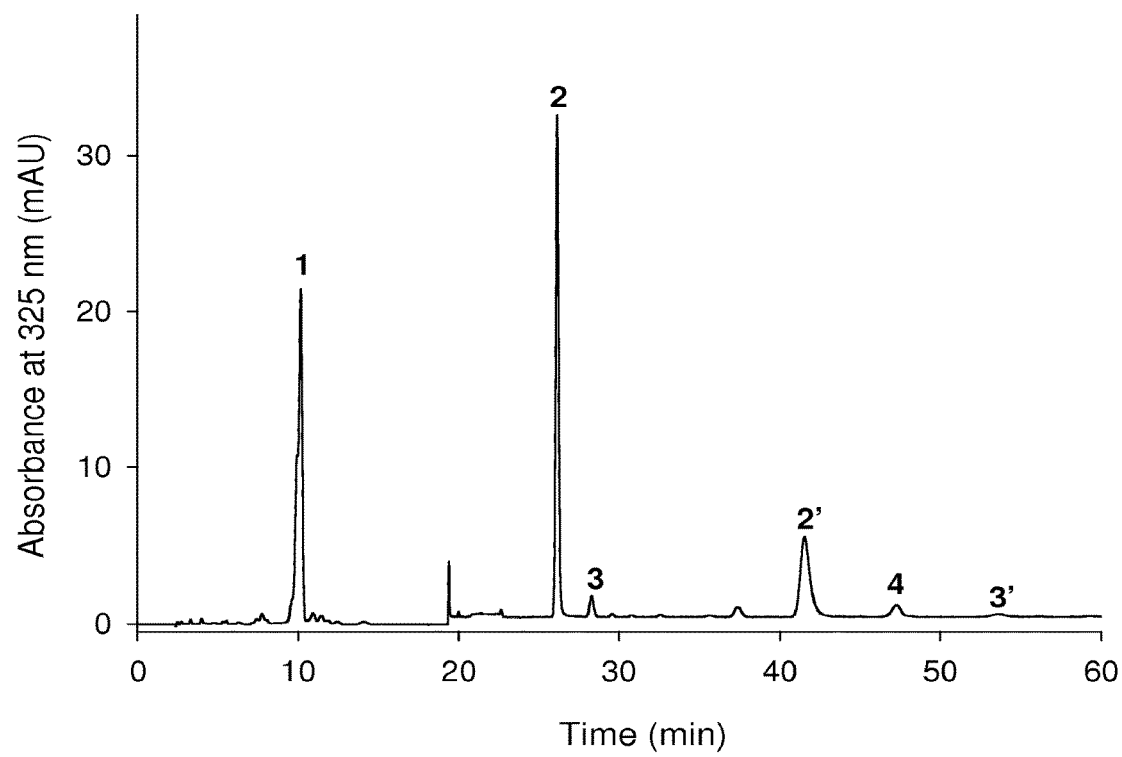
FIG. 6 illustrates a chromatogram of HPLC separation of retinoids.

All experimental procedures related to extraction, derivatization, and separation of retinoids from dissected mouse eyes were carried out under dim red light. Two whole mouse eyes were homogenized in 1 ml of 50 mM phosphate buffer, pH 7.0, containing 50% ethanol and 10 mM NH$_2$OH. Ice-cold methanol (1 ml) was added to the homogenates 20 min after incubation at room temperature (RT), non-polar retinoids were extracted twice with 4 ml of hexane. The organic phase was collected, dried down in a SpeedVac and re-solubilized in 0.3 ml of hexane. Three main classes of retinoids (retinyl esters, retinal oximes, and retinols) as well as their geometrical isomers was separated in single run by normal phase HPLC by using an Agilent Si, 5 μm, 4.5×250 mm column and a stepwise gradient of ethylacetate in hexane (0.5% for 15 min, and 6% for up to 60 min) at a flow rate of 1.4 ml/min (FIG. 6). Retinoids were detected at 325 nm (retinyl esters and retinols) and 350 nm (retinyl oximes) with a diode array detector. Those of interest were quantified based on the areas under their peaks calculated with the help of HP Chemstation A.03.03 software and compared with areas calculated based on known amounts of synthetic standards plotted as a standard curve.

Mass Spectrometry of Retinoids

A complementary technique, mass spectrometry, was used to detect, identify, and quantify retinoids and their derivatives in eye tissue. The conjugated polyene chain of retinoids contributes to relatively strong light absorption at UV and visible wavelengths. Thus, absorbance spectra provided information about the number of conjugated double bonds. Moreover, slight differences in wavelengths of maximum absorbance and shapes of the spectra permitted precise identification of retinoid isomers. However, a limitation of this method is the low selectivity of its UV-Vis absorbance, which mandates carefully designed chromatographic conditions and precise identification of the compounds being analyzed. This analysis can become especially challenging when multiple geometric isomers of retinoids at low abundance (less than 3 pmols/eye) or unidentified compounds are present. Thus, we used an alternative technique, mass spectrometry combined with high performance liquid chromatography (LC-MS) to address this issue. Mass spectra of retinoids was acquired by using a LXQ high throughput linear ion trap mass spectrometer (Thermo Scientific, Waltham, Mass.) connected with an Agilent 1100 HPLC system and interfaced with an atmospheric pressure chemical ionization (APCI) source. The APCI source in a positive ionization mode is chosen for LC-MS methodology because of its wide dynamic range and capacity to operate at the high flow rates required for HPLC retinoid separation. The greatest advantage of LC-MS is its sensitivity that reaches the limits of retinoid detection and quantification in the 10 to 50 fmol and 20 to 200 fmol ranges, respectively. Moreover, this LXQ instrument has capability to perform MSn analyses that provide definitive structural identification.

Figure 7:
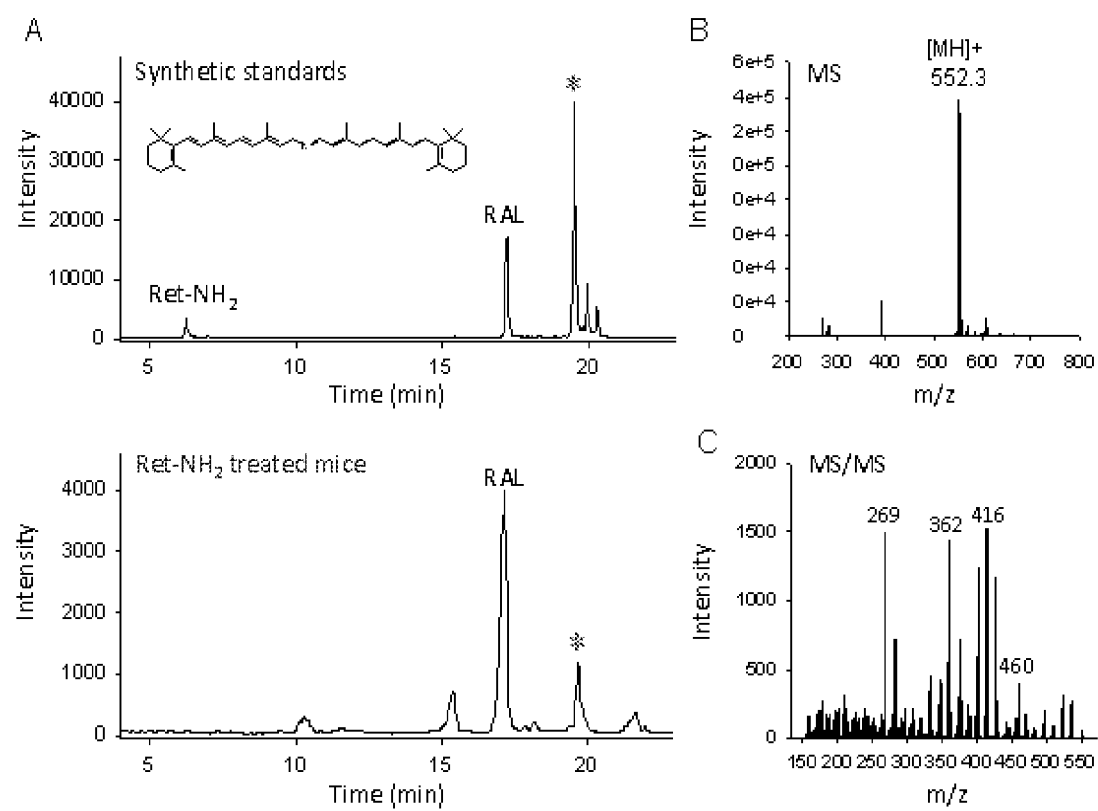
FIG. 7 illustrates a MS/MS spectrum of ritinyl imine fragments in eyes of mice.

Detection and Quantification of Retinal Amine Condensation Products in Mouse Eye Eyes of mice treated with compounds containing primary amines were homogenized in Tris/HCl buffer, pH 9.0, in 50% methanol and extracted with hexane or ethyl acetate depending of the polarity, dried down and resuspended in acetonitrile. After centrifugation, extracted compounds in the supernatant were separated by reverse phase HPLC chromatography (Agilent Zorbax Eclipse XBD C18, 5 μm, 4.6×150 mm column) with a linear gradient of water in acetonitrile (50-100%) for 20 min at a fixed flow rate of 1.5 ml/min. Retinal conjugates were detected and identified with a LXQ mass spectrometer equipped with an APCI source. MS scans were recorded in a SIM mode for each individual compound (FIG. 7 M3). The identity of detected adducts will be confirmed based on their $MS^2$ spectra. Amounts of retinal-amine conjugates will be quantified with the aid of isotopically labeled synthetic standards added prior to extraction.

Figure 8:
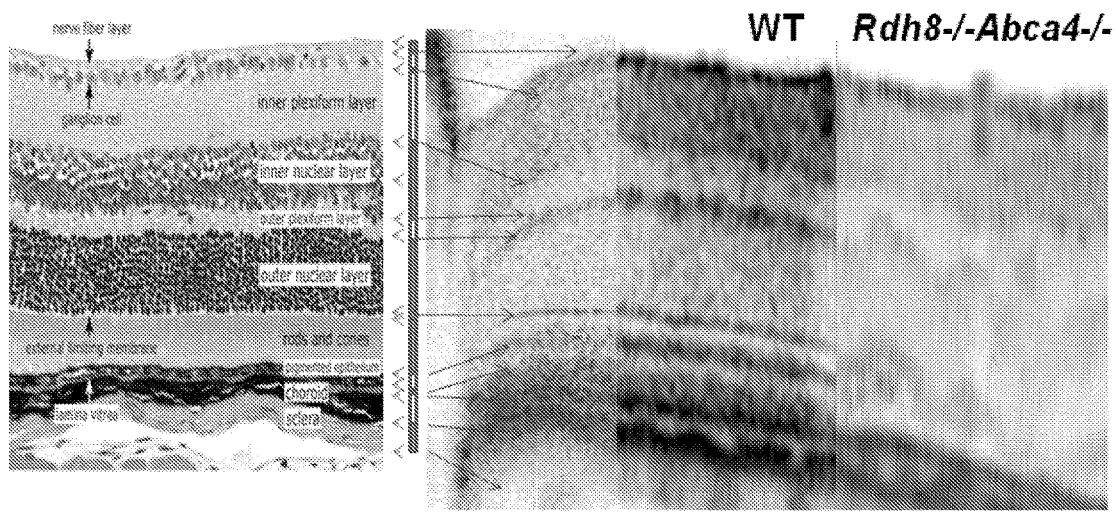
FIG. 8 illustrates SD-OCT images of retinas from WT and Rdh8$^{-/-}$Abca4$^{-/-}$ mice.

Ultra-High Resolution Spectral-Domain Optical Coherence Tomography (SD-OCT) Imaging Although analytical and histological methods provide exhaustive characterization of retina, they cannot be performed in vivo. To reduce the number of sacrificed animals and time required for analysis, SD-OCT from Bioptigen (Research Triangle Park, N.C.) was employed for in vivo imaging of mouse retinas. Bioptigen OCT systems utilize a narrow single-mode beam from a wide bandwidth light source to probe the structure of retina at a higher resolution (2.0 μm) than normal OCT systems. Mice were anesthetized by intraperitoneal (IP) injection of 20 μl/g bw of 6 mg/ml ketamine and 0.44 mg/ml xylazine diluted with 10 mM sodium phosphate, pH 7.2, containing 100 mM NaCl. Pupils were dilated with 1% tropicamide. In vivo SD-OCT images were obtained from both eyes. Four pictures acquired in a B-scan mode were used to construct the final averaged images (FIG. 8). SD-OCT imaging enabled us to identify early pathological changes in the retina and monitor progression or amelioration/prevention of pathological lesions quantitatively under various therapeutic regimens in the same live animal at a resolution comparable to that obtained by current histopathological methods that employ cross sections of the retina.

Grading with OCT

In vivo retinal structures of $Rdh8^{-/-}Abca4^{-/-}$ mice are imaged by SD-OCT 7 days after 10,000 lux illumination for 30 min at 4 weeks of age. FIG. 9 illustrates $Rdh8^{-/-}Abca4^{-/-}$ mouse without light shows healthy retina, whereas light with 10,000 lux for 30 min cause severe retinal degeneration (left panel). Preventive effects of compounds in retinal morphology are indicated as OCT score (right panel).

Score 5: no retinal degeneration
Score 4: regional retinal degeneration (less than 1000 μm width)
Score 3: widely observed retinal degeneration (more than 1000 μm width) with reflection of ELM
Score 2: widely observed retinal degeneration (more than 1000 μm width) without reflection of ELM
Score 1: severe retinal degeneration without reflection from photoreceptors as well as light exposed $Rdh8^{-/-}Abca4^{-/-}$ mice (see left panel)

Results

The following Table lists the OCT score and 11 cis-retinal area of $ABCA4^{-/-}/RDH8^{-/-}$ treated with Flumadine, Nameda, Potaba, Dapsone, Paser, Luvox, Seromycin, Aminohippurate Sodium, Cuprimine, Januvia, Primaxin I.M., Prinivil, Sulfamylon, Exforge, Stalevo, Sodium Diuril, Lyrica, (R)-3-(aminomethyl)-5-methylhexanoic acid, Asacol, Tamiflu, and Rilutek. As noted in the Table, $ABCA4^{-/-}/RDH8^{-/-}$ mice treated with either Flumadine, Dapsone, Paser, Luvox, Seromycin, Januvia, Sulfamylon, Exforge, Sodium Diuril, Lyrica, (R)-3-(aminomethyl)-5-methylhexanoic acid, Asacol, or Rilutek had a optical coherence tomography score of at least about 2.5 and the drug increased 11-cis-retinal amount at least about 30% in comparison to untreated control animal and were effective in treating retinal degeneration in the mice. It is noted that the three FDA approved drugs that readily formed Schiff bases in Example 1 with all-trans-RAL under simulated physiological conditions had a optical coherence tomography score of at least about 2.5, increased 11-cis-retinal amount at least about 30% in comparison to untreated control animal, and were effective in treating retinal degeneration in the mice. In contrast, the two FDA approved drugs that did not readily formed Schiff bases in Example 1 with all-trans-RAL under simulated physiological conditions had an optical coherence tomography score below 2.5, did not increase 11-cis-retinal amount at least about 30% in comparison to untreated control animal, and were ineffective in treating retinal degeneration in the mice.

TABLE

|   | | Score OCT | 11cRAL (area) |
|---|---|---|---|
| 1 | Flumadine | ≥2.5 | 135.3 |
| 2 | Nameda | 1.7 | 97.6 |
| 3 | Potaba | 2.3 | 90.6 |
| 4 | Dapsone | ≥2.5 | 156.5 |
| 5 | Paser | ≥2.5 | 151.9 |
| 6 | Luvox | ≥2.5 | 175.5 |
| 7 | Seromycin | ≥2.5 | 159.9 |
| 8 | Aminohippurate Sodium | 1 | 109.4 |
| 9 | Cuprimine | 1.7 | 118.5 |
| 10 | Januvia | ≥2.5 | 126.8 |
| 11 | Primaxin I.M. | 1.7 | 108.1 |
| 12 | Prinivil | 2.0 | 132.7 |
| 13 | Sulfamylon | ≥2.5 | 166.1 |
| 14 | Exforge | ≥2.5 | 173.8 |
| 15 | Stalevo | 1.3 | 86.7 |
| 16 | Sodium Diuril | ≥2.5 | 139.7 |
| 17 | Lyrica (S)-3-(aminomethyl)-5-methylhexanoic acid | ≥2.5 | 166.5 |
| 18 | (R)-3-(aminomethyl)-5-methylhexanoic acid | ≥2.5 | 164.8 |
| 19 | Asacol | ≥2.5 | 140.2 |
| 20 | Tamiflu | 1.3 | 87.3 |
| 21 | Rilutek | ≥2.5 | 158.2 |
| 22 | No Treatment | 1 | 88.2 |

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

The invention claimed is:

1. A method of treating a retinal pathology associated with aberrant all-trans-retinal clearance in the retina outer segment of a subject in need thereof, comprising administering to a subject in need thereof a therapeutically effective amount of a primary amine compound of formula:

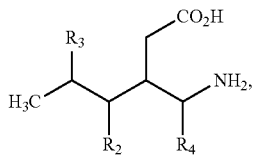

or a pharmaceutically acceptable salt thereof, wherein:
$R_2$ is hydrogen or $(C_1-C_6)$ straight or branched unsubstituted or substituted alkyl;
$R_3$ is $(C_1-C_8)$ straight or branched unsubstituted or substituted alkyl, $(C_2-C_8)$ straight or branched alkenyl, $(C_3-C_7)$ cycloalkyl, $(C_1-C_6)$ alkoxy, alkylcycloalkyl, alkylalkoxy, alkyl OH, alkylphenyl, alkylphenoxy, phenyl, or substituted phenyl; and
$R_4$ is hydrogen or $(C_1-C_6)$ straight or branched unsubstituted or substituted alkyl or carboxyl, wherein the retinal pathology is macular degeneration, Stargardt's disease, geographic atrophy, Leber's congenital amaurosis, or retinitis pigmentosa.

2. The method of claim 1, wherein the primary amine compound is selected from the group consisting of:

3-Aminomethyl-5-methylhexanoic acid; 3-Aminomethyl-5-methylheptanoic acid; 3-Aminomethyl-5-methyl-octanoic acid; 3-Aminomethyl-5-methyl-nonanoic acid; 3-Aminomethyl-5-methyl-decanoic acid; 3-Aminomethyl-5-methyl-undecanoic acid; 3-Aminomethyl-5-methyl-dodecanoic acid; 3-Aminomethyl-5-methyl-tridecanoic acid; 3-Aminomethyl-5-cyclopropyl-hexanoic acid; 3-Aminomethyl-5-cyclobutyl-hexanoic acid; 3-Aminomethyl-5-cyclopentyl-hexanoic acid; 3-Aminomethyl-5-cyclohexyl-hexanoic acid; 3-Aminomethyl-5-trifluoromethyl-hexanoic acid; 3-Aminomethyl-5-phenyl-hexanoic acid; 3-Aminomethyl-5-(2-chlorophenyl)-hexanoic acid; 3-Aminomethyl-5-(3-chlorophenyl)-hexanoic acid; 3-Aminomethyl-5-(4-chlorophenyl)-hexanoic acid; 3-Aminomethyl-5-(2-methoxyphenyl)-hexanoic acid; 3-Aminomethyl-5-(3-methoxyphenyl)-hexanoic acid; 3-Aminomethyl-5-(4-methoxyphenyl)-hexanoic acid; 3-Aminomethyl-5-(phenylmethyl)-hexanoic acid; (S)-3-(Aminomethyl)-5-methylhexanoic acid; (R)-3-(Aminomethyl)-5-methylhexanoic acid; (3R,4S)-3-Aminomethyl-4,5-dimethyl-hexanoic acid; 3-Aminomethyl-4,5-dimethyl-hexanoic acid; (3R,4S)-3-Aminomethyl-4,5-dimethyl-hexanoic acid MP; (3S,4S)-3-Aminomethyl-4,5-dimethyl-hexanoic acid; (3R,4R)-3-Aminomethyl-4,5-dimethyl-hexanoic acid MP; 3-Aminomethyl-4-isopropyl-hexanoic acid; 3-Aminomethyl-4-isopropyl-heptanoic acid; 3-Aminomethyl-4-isopropyl-octanoic acid; 3-Aminomethyl-4-isopropyl-nonanoic acid; 3-Aminomethyl-4-isopropyl-decanoic acid; 3-Aminomethyl-4-phenyl-5-methyl-hexanoic acid; (3S,5S)-3-Aminomethyl-5-methoxy-hexanoic acid; (3S,5S)-3-Aminomethyl-5-ethoxy-hexanoic acid; (3S,5S)-3-Aminomethyl-5-propoxy-hexanoic acid; (3S,5S)-3-Aminomethyl-5-isopropoxy-hexanoic acid; (3S,5S)-3-Aminomethyl-5-tert-butoxy-hexanoic acid; (3S,5S)-3-Aminomethyl-5-fluoromethoxy-hexanoic acid; (3S,5S)-3-Aminomethyl-5-(2-fluoro-ethoxy)-hexanoic acid; (3S,5S)-3-Aminomethyl-5-(3,3,3-trifluoro-propoxy)-hexanoic acid; (3S,5S)-3-Aminomethyl-5-phenoxy-hexanoic acid; (3S,5S)-3-Aminomethyl-5-(4-chloro-phenoxy)-hexanoic acid; (3S,5S)-3-Aminomethyl-5-(3-chloro-phenoxy)-hexanoic acid; (3S,5S)-3-Aminomethyl-5-(2-chloro-phenoxy)-hexanoic acid; (3S,5S)-3-Aminomethyl-5-(4-fluoro-phenoxy)-hexanoic acid; (3S,5S)-3-Aminomethyl-5-(3-fluoro-phenoxy)-hexanoic acid; (3S,5S)-3-Aminomethyl-5-(2-fluoro-phenoxy)-hexanoic acid; (3S,5S)-3-Aminomethyl-5-(4-methoxy-phenoxy)-hexanoic acid; (3S,5S)-3-Aminomethyl-5-(3-methoxy-phenoxy)-hexanoic acid; (3S,5S)-3-Aminomethyl-5-(2-methoxy-phenoxy)-hexanoic acid; (3S,5S)-3-Aminomethyl-5-(4-nitro-phenoxy)-hexanoic acid; (3S,5S)-3-Aminomethyl-5-(3-nitro-phenoxy)-hexanoic acid; (3S,5S)-3-Aminomethyl-5-(2-nitro-phenoxy)-hexanoic acid; (3S,5S)-3-Aminomethyl-6-hydroxy-5-methyl-hexanoic acid; (3S,5S)-3-Aminomethyl-6-methoxy-5-methyl-hexanoic acid; (3S,5S)-3-Aminomethyl-6-ethoxy-5-methyl-hexanoic acid; (3S,5S)-3-Aminomethyl-5-methyl-6-propoxy-hexanoic acid; (3S,5S)-3-Aminomethyl-6-isopropoxy-5-methyl-hexanoic acid; (3S,5S)-3-Aminomethyl-6-tert-butoxy-5-methyl-hexanoic acid; (3S,5S)-3-Aminomethyl-6-fluoromethoxy-5-methyl-hexanoic acid; (3S,5S)-3-Aminomethyl-6-(2-fluoro-ethoxy)-5-methyl-hexanoic acid; (3S,5S)-3-Aminomethyl-5-methyl-6-(3,3,3-trifluoro-propoxy)-hexanoic acid; (3S,5S)-3-Aminomethyl-5-methyl-6-phenoxy-hexanoic acid; (3S,5S)-3-Aminomethyl-6-(4-chloro-phenoxy)-5-methyl-hexanoic acid; (3S,5S)-3-Aminomethyl-6-(3-chloro-phenoxy)-5-methyl-hexanoic acid; (3S,5S)-3-Aminomethyl-6-(2-chloro-phenoxy)-5-methyl-hexanoic acid; (3S,5S)-3-Aminomethyl-6-(4-fluoro-phenoxy)-5-methyl-hexanoic acid; (3S,5S)-3-Aminomethyl-6-(3-fluoro-phenoxy)-5-methyl-hexanoic acid; (3S,5S)-3-Aminomethyl-6-(2-fluoro-phenoxy)-5-methyl-hexanoic acid; (3S,5S)-3-Aminomethyl-6-(4-methoxy-phenoxy)-5-methyl-hexanoic acid; (3S,5S)-3-Aminomethyl-6-(3-methoxy-phenoxy)-5-methyl-hexanoic acid; (3S,5S)-3-Aminomethyl-6-(2-methoxy-phenoxy)-5-methyl-hexanoic acid; (3S,5S)-3-Aminomethyl-5-methyl 6-(4-trifluoromethyl-phenoxy)-hexanoic acid; (3S,5S)-3-Aminomethyl-5-methyl 6-(3-trifluoromethyl-phenoxy)-hexanoic acid; (3S,5S)-3-Aminomethyl-5-methyl 6-(2-trifluoromethyl-phenoxy)-hexanoic acid; (3S,5S)-3-Aminomethyl-5-methyl 6-(4-nitro-phenoxy)-hexanoic acid; (3S,5S)-3-Aminomethyl-5-methyl 6-(3-nitro-phenoxy)-hexanoic acid; (3S,5S)-3-Aminomethyl-5-methyl 6-(2-nitro-phenoxy)-hexanoic acid; (3S,5S)-3-Aminomethyl-6-benzyloxy-5-methyl-hexanoic acid; (3S,5S)-3-Aminomethyl-7-hydroxy-5-methyl-heptanoic acid; (3S,5S)-3-Aminomethyl-7-methoxy-5-methyl-heptanoic acid; (3S,5S)-3-Aminomethyl-7-ethoxy-5-methyl-heptanoic acid; (3S,5S)-3-Aminomethyl-5-methyl-7-propoxy-heptanoic acid; (3S,5S)-3-Aminomethyl-7-isopropoxy-5-methyl-heptanoic acid; (3S,5S)-3-Aminomethyl-7-tert-butoxy-5-methyl-heptanoic acid; (3S,5S)-3-Aminomethyl-7-fluoromethoxy-5-methyl-heptanoic acid; (3S,5S)-3-Aminomethyl-7-(2-fluoro-ethoxy)-5-methyl-heptanoic acid; (3S,5S)-3-Aminomethyl-5-methyl-7-(3,3,3-trifluoro-propoxy)-heptanoic acid; (3S,5S)-3-Aminomethyl-7-benzyloxy-5-methyl-heptanoic acid; (3S,5S)-3-Aminomethyl-5-methyl-7-phenoxy-heptanoic acid; (3S,5S)-3-Aminomethyl-7-(4-chloro-phenoxy)-5-methyl-heptanoic acid; (3S,5S)-3-Aminomethyl-7-(3-chloro-phenoxy)-5-methyl-heptanoic acid; (3S,5S)-3-Aminomethyl-7-(2-chloro-phenoxy)-5-methyl-heptanoic acid; (3S,5S)-3-Aminomethyl-7-(4-fluoro-phenoxy)-5-methyl-heptanoic acid; (3S,5S)-3-Aminomethyl-7-(3-fluoro-phenoxy)-5-methyl-heptanoic acid; (3S,5S)-3-Aminomethyl-7-(2-fluoro-phenoxy)-5-methyl-heptanoic acid; (3S,5S)-3-Aminomethyl-7-(4-methoxy-phenoxy)-5-methyl-heptanoic acid; (3S,5S)-3-Aminomethyl-7-(3-methoxy-phenoxy)-5-methyl-heptanoic acid; (3S,5S)-3-Aminomethyl-7-(2-methoxy-phenoxy)-5-methyl-heptanoic acid; (3S,5S)-3-Aminomethyl-5-methyl-7-(4-trifluoromethyl-phenoxy)-heptanoic acid; (3S,5S)-3-Aminomethyl-5-methyl-7-(3-trifluoromethyl-phenoxy)-heptanoic acid; (3S,5S)-3-Aminomethyl-5-methyl-7-(2-trifluoromethyl-phenoxy)-heptanoic acid; (3S,5S)-3-Aminomethyl-5-methyl-7-(4-nitro-phenoxy)-heptanoic acid; (3S,5S)-3-Aminomethyl-5-methyl-7-(3-nitro-phenoxy)-heptanoic acid; (3S,5S)-3-Aminomethyl-5-methyl-7-(2-nitro-phenoxy)-heptanoic acid; (3S,5S)-3-Aminomethyl-5-methyl-6-phenyl-hexanoic acid; (3S,5S)-3-Aminomethyl-6-(4-chloro-phenyl)-5-methyl-hexanoic acid; (3S,5S)-3-Aminomethyl-6-(3-chloro-phenyl)-5-methyl-hexanoic acid; (3S,5S)-3-Aminomethyl-6-(2-chloro-phenyl)-5-methyl-hexanoic acid; (3S,5S)-3-Aminomethyl-6-(4-methoxy-phenyl)-5-methyl-hexanoic acid; (3S,5S)-3-Aminomethyl-6-(3-methoxy-phenyl)-5-methyl-hexanoic acid; (3S,5S)-3-Aminomethyl-6-(2-methoxy-phenyl)-5-methyl-hexanoic acid; (3S,5S)-3-Aminomethyl-6-(4-fluoro-phenyl)-5-methyl-hexanoic acid; (3S,5S)-3-Aminomethyl-6-(3-fluoro-phenyl)-5-methyl-hexanoic acid; (3S,5S)-3-Aminomethyl-6-(2-fluoro-phenyl)-5-methyl-hexanoic acid; (3S,5R)-3-Aminomethyl-5-methyl-7-phenyl-heptanoic acid; (3S,5R)-3-Aminomethyl-7-(4-chloro-phenyl)-5-methyl-heptanoic acid; (3S,5R)-3-Aminomethyl-7-(3-chloro-phenyl)-5-methyl-heptanoic acid; (3S,5R)-3-Aminomethyl-7-(2-chloro-phenyl)-5-methyl-heptanoic acid; (3S,5R)-3-Aminomethyl-7-(4-methoxy-phenyl)-5-methyl-heptanoic acid; (3S,5R)-3-Aminomethyl-7-(3-methoxy-phenyl)-5-methyl-heptanoic acid; (3S,5R)-3-Aminomethyl-7-(2-methoxy-phenyl)-5-methyl-heptanoic acid; (3S,5R)-3-Aminomethyl-7-(4-fluoro-phenyl)-5-methyl-heptanoic acid; (3S,5R)-3-Aminomethyl-7-(3-fluoro-phenyl)-5-methyl-heptanoic acid; (3S,5R)-3-Aminomethyl-7-(2-fluoro-phenyl)-5-methyl-heptanoic acid; (3S,5R)-3-Aminomethyl-5-methyl-oct-7-enoic acid; (3S,5R)-3-Aminomethyl-5-methyl-non-8-enoic acid; (E)-(3S,5S)-3-Aminomethyl-5-methyl-oct-6-enoic acid; (Z)-(3S,5S)-3-Aminomethyl-5-methyl-oct-6-enoic acid; (Z)-(3S,5S)-3-Aminomethyl-5-methyl-non-6-enoic acid; (E)-(3S,5S)-3-Aminomethyl-5-methyl-non-6-enoic acid; (E)-(3S,5R)-3-Aminomethyl-5-methyl-non-7-enoic acid; (Z)-(3S,5R)-3-Aminomethyl-5-methyl-non-7-enoic acid; (Z)-(3S,5R)-3-Aminomethyl-5-methyl-dec-7-enoic acid; (E)-(3S,5R)-3-Aminomethyl-5-methyl-undec-7-enoic acid; (3S,5S)-3-Aminomethyl-5,6,6-trimethyl-heptanoic acid; (3S,5S)-3-Aminomethyl-5,6-dimethyl-heptanoic acid; (3S,5S)-3-Aminomethyl-5-cyclopropyl-hexanoic acid; (3S,5S)-3-Aminomethyl-5-cyclobutyl-hexanoic acid; (3S,5S)-3-Aminomethyl-5-cyclopentyl-hexanoic acid; (3S,5S)-3-Aminomethyl-5-cyclohexyl-hexanoic acid; (3S,5R)-3-Aminomethyl-5-methyl-heptanoic acid; (3S,5R)-3-Aminomethyl-5-methyl-octanoic acid; (3S,5R)-3-Aminomethyl-5-methyl-nonanoic acid; (3S,5R)-3-Aminomethyl-5-methyl-decanoic acid; (3S,5R)-3-Aminomethyl-5-methyl-undecanoic acid; (3S,5R)-3-Aminomethyl-5-methyl-dodecanoic acid; (3S,5R)-3-Aminomethyl-5,9-dimethyl-decanoic acid; (3S,5R)-3-Aminomethyl-5,7-dimethyl-octanoic acid; (3S,5R)-3-Aminomethyl-5,8-dimethyl-nonanoic acid; (3S,5R)-3-Aminomethyl-6-cyclopropyl-5-methyl-hexanoic acid; (3S,5R)-3-Aminomethyl-6-cyclobutyl-5-methyl-hexanoic acid; (3S,5R)-3-Aminomethyl-6-cyclopentyl-5-methyl-hexanoic acid; (3S,5R)-3-Aminomethyl-6-cyclohexyl-5-methyl-hexanoic acid; (3S,5R)-3-Aminomethyl-7-cyclopropyl-5-methyl-heptanoic acid; (3S,5R)-3-Aminomethyl-7-cyclobutyl-5-methyl-heptanoic acid; (3S,5R)-3-Aminomethyl-7-cyclopentyl-5-methyl-heptanoic acid; (3S,5R)-3-Aminomethyl-7-cyclohexyl-5-methyl-heptanoic acid; (3S,5R)-3-Aminomethyl-8-cyclopropyl-5-methyl-octanoic acid; (3S,5R)-3-Aminomethyl-8-cyclobutyl-5-methyl-octanoic acid; (3S,5R)-3-Aminomethyl-8-cyclopentyl-5-methyl-octanoic acid; (3S,5R)-3-Aminomethyl-8-cyclohexyl-5-methyl-octanoic acid; (3S,5S)-3-Aminomethyl-6-fluoro-5-methyl-hexanoic acid; (3S,5S)-3-Aminomethyl-7-fluoro-5-methyl-heptanoic acid; (3S,5R)-3-Aminomethyl-8-fluoro-5-methyl-octanoic acid; (3S,5R)-3-Aminomethyl-9-fluoro-5-methyl-nonanoic acid; (3S,5S)-3-Aminomethyl-7,7,7-trifluoro-5-methyl-heptanoic acid; (3S,5R)-3-Aminomethyl-8,8,8-trifluoro-5-methyl-octanoic acid; (3S,5R)-3-Aminomethyl-5-methyl-8-phenyl-octanoic acid; (3S,5S)-3-Aminomethyl-5-methyl-6-phenyl-hexanoic acid; and (3S,5R)-3-Aminomethyl-5-methyl-7-phenyl-heptanoic acid,
or a pharmaceutically acceptable salt thereof

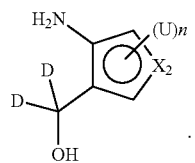

3. A method of treating a retinal pathology associated with aberrant all-trans-retinal clearance in the retina outer segment of a subject in need thereof, comprising administering to a subject in need thereof a therapeutically effective amount of a primary amine compound of formula:

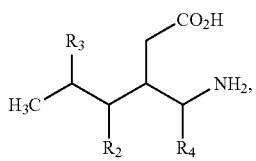

or a pharmaceutically acceptable salt thereof, wherein:
$R_2$ is hydrogen, $(C_1-C_6)$ straight or branched alkyl, or phenyl;
$R_3$ is $(C_1-C_8)$ straight or branched alkyl, $(C_2-C_8)$ straight or branched alkenyl, $(C_3-C_7)$ cycloalkyl, $(C_1-C_6)$ alkoxy, alkylcycloalkyl, alkylalkoxy, alkyl OH, alkylphenyl, alkylphenoxy, phenyl, or substituted phenyl;
$R_4$ is hydrogen; and
$R_2$ is straight or branched $(C_1-C_6)$ alkyl, or phenyl when $R_3$ is methyl, wherein the retinal pathology is macular degeneration, Stargardt's disease, geographic atrophy, Leber's congenital amaurosis, or retinitis pigmentosa.

4. The method of claim 3, wherein the primary amine compound is selected from the group consisting of:
3-Aminomethyl-5-methylhexanoic acid; 3-Aminomethyl-5-methylheptanoic acid; 3-Aminomethyl-5-methyl-octanoic acid; 3-Aminomethyl-5-methyl-nonanoic acid; 3-Aminomethyl-5-methyl-decanoic acid; 3-Aminomethyl-5-methyl-undecanoic acid; 3-Aminomethyl-5-methyl-dodecanoic acid; 3-Aminomethyl-5-methyl-tridecanoic acid; 3-Aminomethyl-5-cyclopropyl-hexanoic acid; 3-Aminomethyl-5-cyclobutyl-hexanoic acid; 3-Aminomethyl-5-cyclopentyl-hexanoic acid; 3-Aminomethyl-5-cyclohexyl-hexanoic acid; 3-Aminomethyl-5-trifluoromethyl-hexanoic acid; 3-Aminomethyl-5-phenyl-hexanoic acid; 3-Aminomethyl-5-(2-chlorophenyl)-hexanoic acid; 3-Aminomethyl-5-(3-chlorophenyl)-hexanoic acid; 3-Aminomethyl-5-(4-chlorophenyl)-hexanoic acid; 3-Aminomethyl-5-(2-methoxyphenyl)-hexanoic acid; 3-Aminomethyl-5-(3-methoxyphenyl)-hexanoic acid; 3-Aminomethyl-5-(4-methoxyphenyl)-hexanoic acid; 3-Aminomethyl-5-(phenylmethyl)-hexanoic acid; (S)-3-(Aminomethyl)-5-methyl-hexanoic acid; (R)-3-(Aminomethyl)-5-methyl-hexanoic acid; (3R,4S)-3-Aminomethyl-4,5-dimethyl-hexanoic acid; 3-Aminomethyl-4,5-dimethyl-hexanoic acid; (3R,4S)-3-Aminomethyl-4,5-dimethyl-hexanoic acid MP; (3S,4S)-3-Aminomethyl-4,5-dimethyl-hexanoic acid; (3R,4R)-3-Aminomethyl-4,5-dimethyl-hexanoic acid MP; 3-Aminomethyl-4-isopropyl-hexanoic acid; 3-Aminomethyl-4-isopropyl-heptanoic acid; 3-Aminomethyl-4-isopropyl-octanoic acid; 3-Aminomethyl-4-isopropyl-nonanoic acid; 3-Aminomethyl-4-isopropyl-decanoic acid; 3-Aminomethyl-4-phenyl-5-methyl-hexanoic acid; (3S,5S)-3-Aminomethyl-5-methoxy-hexanoic acid; (3S,5S)-3-Aminomethyl-5-ethoxy-hexanoic acid; (3S,5S)-3-Aminomethyl-5-propoxy-hexanoic acid; (3S,5S)-3-Aminomethyl-5-isopropoxy-hexanoic acid; (3S,5S)-3-Aminomethyl-5-tert-butoxy-hexanoic acid; (3S,5S)-3-Aminomethyl-5-fluoromethoxy-hexanoic acid; (3S,5S)-3-Aminomethyl-5-(2-fluoro-ethoxy)-hexanoic acid; (3S,5S)-3-Aminomethyl-5-(3,3,3-trifluoro-propoxy)-hexanoic acid; (3S,5S)-3-Aminomethyl-5-phenoxy-hexanoic acid; (3S,5S)-3-Aminomethyl-5-(4-chloro-phenoxy)-hexanoic acid; (3S,5S)-3-Aminomethyl-5-(3-chloro-phenoxy)-hexanoic acid; (3S,5S)-3-Aminomethyl-5-(2-chloro-phenoxy)-hexanoic acid; (3S,5S)-3-Aminomethyl-5-(4-fluoro-phenoxy)-hexanoic acid; (3S,5S)-3-Aminomethyl-5-(3-fluoro-phenoxy)-hexanoic acid; (3S,5S)-3-Aminomethyl-5-(2-fluorophenoxy)-hexanoic acid; (3S,5S)-3-Aminomethyl-5-(4-methoxy-phenoxy)-hexanoic acid; (3S,5S)-3-Aminomethyl-5-(3-methoxy-phenoxy)-hexanoic acid; (3S,5S)-3-Aminomethyl-5-(2-methoxyphenoxy)-hexanoic acid; (3S,5S)-3-Aminomethyl-5-(4-nitro-phenoxy)-hexanoic acid; (3S,5S)-3-Aminomethyl-5-(3-nitro-phenoxy)-hexanoic acid; (3S,5S)-3-Aminomethyl-5-(2-nitro-phenoxy)-hexanoic acid; (3S,5S)-3-Aminomethyl-6-hydroxy-5-methyl-hexanoic acid; (3S,5S)-3-Aminomethyl-6-methoxy-5-methyl-hexanoic acid; (3S,5S)-3-Aminomethyl-6-ethoxy-5-methylhexanoic acid; (3S,5S)-3-Aminomethyl-5-methyl-6-propoxy-hexanoic acid; (3S,5S)-3-Aminomethyl-6-isopropoxy-5-methyl-hexanoic acid; (3S,5S)-3-Aminomethyl-6-tert-butoxy-5-methyl-hexanoic acid; (3S,5S)-3-Aminomethyl-6-fluoromethoxy-5-methyl-hexanoic acid; (3S,5S)-3-Aminomethyl-6-(2-fluoro-ethoxy)-5-methyl-hexanoic acid; (3S,5S)-3-Aminomethyl-5-methyl-6-(3,3,3-trifluoro-propoxy)-hexanoic acid; (3S,5S)-3-Aminomethyl-5-methyl-6-phenoxy-hexanoic acid; (3S,5S)-3-Aminomethyl-6-(4-chloro-phenoxy)-5-methyl-hexanoic acid; (3S,5S)-3-Aminomethyl-6-(3-chloro-phenoxy)-5-methyl-hexanoic acid; (3S,5S)-3-Aminomethyl-6-(2-chlorophenoxy)-5-methyl-hexanoic acid; (3S,5S)-3-Aminomethyl-6-(4-fluoro-phenoxy)-5-methylhexanoic acid; (3S,5S)-3-Aminomethyl-6-(3-fluoro-phenoxy)-5-methyl-hexanoic acid; (3S,5S)-3-Aminomethyl-6-(2-fluoro-phenoxy)-5-methyl-hexanoic acid; (3S,5S)-3-Aminomethyl-6-(4-methoxy-phenoxy)-5-methyl-hexanoic acid; (3S,5S)-3-Aminomethyl-6-(3-methoxy-phenoxy)-5-methyl-hexanoic acid; (3S,5S)-3-Aminomethyl-6-(2-methoxy-phenoxy)-5-methyl-hexanoic acid; (3S,5S)-3-Aminomethyl-5-methyl 6-(4-trifluoromethyl-phenoxy)-hexanoic acid; (3S,5S)-3-Aminomethyl-5-methyl 6-(3-trifluoromethyl-phenoxy)-hexanoic acid; (3S,5S)-3-Aminomethyl-5-methyl 6-(2-trifluoromethyl-phenoxy)-hexanoic acid;

(3S,5S)-3-Aminomethyl-5-methyl 6-(4-nitrophenoxy)-hexanoic acid; (3S,5S)-3-Aminomethyl-5-methyl 6-(3-nitro-phenoxy)-hexanoic acid; (3S,5S)-3-Aminomethyl-5-methyl 6-(2-nitro-phenoxy)-hexanoic acid; (3S,5S)-3-Aminomethyl-6-benzyloxy-5-methyl-hexanoic acid; (3S,5S)-3-Aminomethyl-7-hydroxy-5-methyl-heptanoic acid; (3S,5S)-3-Aminomethyl-7-methoxy-5-methyl-heptanoic acid; (3S,5S)-3-Aminomethyl-7-ethoxy-5-methyl-heptanoic acid; (3S,5S)-3-Aminomethyl-5-methyl-7-propoxy-heptanoic acid; (3S,5S)-3-Aminomethyl-7-isopropoxy-5-methyl-heptanoic acid; (3S,5S)-3-Aminomethyl-7-tert-butoxy-5-methyl-heptanoic acid; (3S,5S)-3-Aminomethyl-7-fluoromethoxy-5-methyl-heptanoic acid; (3S,5S)-3-Aminomethyl-7-(2-fluoro-ethoxy)-5-methyl-heptanoic acid; (3S,5S)-3-Aminomethyl-5-methyl-7-(3,3,3-trifluoro-propoxy)-heptanoic acid; (3S,5S)-3-Aminomethyl-7-benzyloxy-5-methyl-heptanoic acid; (3S,5S)-3-Aminomethyl-5-methyl-7-phenoxy-heptanoic acid; (3S,5S)-3-Aminomethyl-7-(4-chloro-phenoxy)-5-methyl-heptanoic acid; (3S,5S)-3-Aminomethyl-7-(3-chlorophenoxy)-5-methyl-heptanoic acid; (3S,5S)-3-Aminomethyl-7-(2-chloro-phenoxy)-5-methylheptanoic acid; (3S,5S)-3-Aminomethyl-7-(4-fluoro-phenoxy)-5-methyl-heptanoic acid; (3S,5S)-3-Aminomethyl-7-(3-fluoro-phenoxy)-5-methyl-heptanoic acid; (3S,5S)-3-Aminomethyl-7-(2-fluorophenoxy)-5-methyl-heptanoic acid; (3S,5S)-3-Aminomethyl-7-(4-methoxy-phenoxy)-5-methylheptanoic acid; (3S,5S)-3-Aminomethyl-7-(3-methoxy-phenoxy)-5-methyl-heptanoic acid; (3S,5S)-3-Aminomethyl-7-(2-methoxy-phenoxy)-5-methyl-heptanoic acid; (3S,5S)-3-Aminomethyl-5-methyl-7-(4-trifluoromethyl-phenoxy)-heptanoic acid; (3S,5S)-3-Aminomethyl-5-methyl-7-(3-trifluoromethyl-phenoxy)-heptanoic acid; (3S,5S)-3-Aminomethyl-5-methyl-7-(2-trifluoromethylphenoxy)-heptanoic acid; (3S,5S)-3-Aminomethyl-5-methyl-7-(4-nitro-phenoxy)-heptanoic acid; (3S,5S)-3-Aminomethyl-5-methyl-7-(3-nitro-phenoxy)-heptanoic acid; (3S,5S)-3-Aminomethyl-5-methyl-7-(2-nitro-phenoxy)-heptanoic acid; (3S,5S)-3-Aminomethyl-5-methyl-6-phenyl-hexanoic acid; (3S,5S)-3-Aminomethyl-6-(4-chloro-phenyl)-5-methyl-hexanoic acid; (3S,5S)-3-Aminomethyl-6-(3-chloro-phenyl)-5-methyl-hexanoic acid; (3S,5S)-3-Aminomethyl-6-(2-chlorophenyl)-5-methyl-hexanoic acid; (3S,5S)-3-Aminomethyl-6-(4-methoxy-phenyl)-5-methyl-hexanoic acid; (3S,5S)-3-Aminomethyl-6-(3-methoxy-phenyl)-5-methyl-hexanoic acid; (3S,5S)-3-Aminomethyl-6-(2-methoxy-phenyl)-5-methyl-hexanoic acid; (3S,5S)-3-Aminomethyl-6-(4-fluorophenyl)-5-methyl-hexanoic acid; (3S,5S)-3-Aminomethyl-6-(3-fluoro-phenyl)-5-methyl-hexanoic acid; (3S,5S)-3-Aminomethyl-6-(2-fluoro-phenyl)-5-methyl-hexanoic acid; (3S,5R)-3-Aminomethyl-5-methyl-7-phenyl-heptanoic acid; (3S,5R)-3-Aminomethyl-7-(4-chloro-phenyl)-5-methyl-heptanoic acid; (3S,5R)-3-Aminomethyl-7-(3-chloro-phenyl)-5-methyl-heptanoic acid; (3S,5R)-3-Aminomethyl-7-(2-chloro-phenyl)-5-methyl-heptanoic acid; (3S,5R)-3-Aminomethyl-7-(4-methoxy-phenyl)-5-methyl-heptanoic acid; (3S,5R)-3-Aminomethyl-7-(3-methoxy-phenyl)-5-methyl-heptanoic acid; (3S,5R)-3-Aminomethyl-7-(2-methoxy-phenyl)-5-methyl-heptanoic acid; (3S,5R)-3-Aminomethyl-7-(4-fluoro-phenyl)-5-methyl-heptanoic acid; (3S,5R)-3-Aminomethyl-7-(3-fluoro-phenyl)-5-methyl-heptanoic acid; (3S,5R)-3-Aminomethyl-7-(2-fluoro-phenyl)-5-methylheptanoic acid; (3S,5R)-3-Aminomethyl-5-methyl-oct-7-enoic acid; (3S,5R)-3-Aminomethyl-5-methyl-non-8-enoic acid; (E)-(3S,5S)-3-Aminomethyl-5-methyl-oct-6-enoic acid; (Z)-(3S,5S)-3-Aminomethyl-5-methyl-oct-6-enoic acid; (Z)-(3S,5S)-3-Aminomethyl-5-methyl-non-6-enoic acid; (E)-(3S,5S)-3-Aminomethyl-5-methyl-non-6-enoic acid; (E)-(3S,5R)-3-Aminomethyl-5-methyl-non-7-enoic acid; (Z)-(3S,5R)-3-Aminomethyl-5-methyl-non-7-enoic acid; (Z)-(3S,5R)-3-Aminomethyl-5-methyl-dec-7-enoic acid; (E)-(3S,5R)-3-Aminomethyl-5-methyl-undec-7-enoic acid; (3S,5S)-3-Aminomethyl-5,6,6-trimethyl-heptanoic acid; (3S,5S)-3-Aminomethyl-5,6-dimethyl-heptanoic acid; (3S,5S)-3-Aminomethyl-5-cyclopropyl-hexanoic acid; (3S,5S)-3-Aminomethyl-5-cyclobutyl-hexanoic acid; (3S,5S)-3-Aminomethyl-5-cyclopentyl-hexanoic acid; (3S,5S)-3-Aminomethyl-5-cyclohexyl-hexanoic acid; (3S,5R)-3-Aminomethyl-5-methyl-heptanoic acid; (3S,5R)-3-Aminomethyl-5-methyl-octanoic acid; (3S,5R)-3-Aminomethyl-5-methyl-nonanoic acid; (3S,5R)-3-Aminomethyl-5-methyl-decanoic acid; (3S,5R)-3-Aminomethyl-5-methyl-undecanoic acid; (3S,5R)-3-Aminomethyl-5-methyl-dodecanoic acid; (3S,5R)-3-Aminomethyl-5,9-dimethyl-decanoic acid; (3S,5R)-3-Aminomethyl-5,7-dimethyl-octanoic acid; (3S,5R)-3-Aminomethyl-5,8-dimethyl-nonanoic acid; (3S,5R)-3-Aminomethyl-6-cyclopropyl-5-methylhexanoic acid; (3S,5R)-3-Aminomethyl-6-cyclobutyl-5-methyl-hexanoic acid; (3S,5R)-3-Aminomethyl-6-cyclopentyl-5-methyl-hexanoic acid; (3S,5R)-3-Aminomethyl-6-cyclohexyl-5-methyl-hexanoic acid; (3S,5R)-3-Aminomethyl-7-cyclopropyl-5-methyl-heptanoic acid; (3S,5R)-3-Aminomethyl-7-cyclobutyl-5-methyl-heptanoic acid; (3S,5R)-3-Aminomethyl-7-cyclopentyl-5-methyl-heptanoic acid; (3S,5R)-3-Aminomethyl-7-cyclohexyl-5-methyl-heptanoic acid; (3S,5R)-3-Aminomethyl-8-cyclopropyl-5-methyl-octanoic acid; (3S,5R)-3-Aminomethyl-8-cyclobutyl-5-methyl-octanoic acid; (3S,5R)-3-Aminomethyl-8-cyclopentyl-5-methyl-octanoic acid; (3S,5R)-3-Aminomethyl-8-cyclohexyl-5-methyl-octanoic acid; (3S,5S)-3-Aminomethyl-6-fluoro-5-methylhexanoic acid; (3S,5S)-3-Aminomethyl-7-fluoro-5-methyl-heptanoic acid; (3S,5R)-3-Aminomethyl-8-fluoro-5-methyl-octanoic acid; (3S,5R)-3-Aminomethyl-9-fluoro-5-methyl-nonanoic acid; (3S,5S)-3-Aminomethyl-7,7,7-trifluoro-5-methyl-heptanoic acid; (3S,5R)-3-Aminomethyl-8,8,8-trifluoro-5-methyl-octanoic acid; (3S,5R)-3-Aminomethyl-5-methyl-8-phenyl-octanoic acid; (3S,5S)-3-Aminomethyl-5-methyl-6-phenyl-hexanoic acid; and (3S,5R)-3-Aminomethyl-5-methyl-7-phenyl-heptanoic acid, or a pharmaceutically acceptable salt thereof.

5. The method of claim 1, wherein the primary amine compound is selected from the group consisting of (S)-3-(Aminomethyl)-5-methylhexanoic acid, (R)-3-(Aminomethyl)-5-methylhexanoic acid, and racemic mixtures thereof.

6. The method of claim 1, wherein the primary amine compound includes less than about 1% by weight (S)-3-(Aminomethyl)-5-methylhexanoic acid and greater than about 99% by weight (R)-3-(Aminomethyl)-5-methylhexanoic acid.

7. The method of claim 1, wherein the primary amine compound includes less than about 1% by weight (R)-3-

(Aminomethyl)-5-methylhexanoic acid and greater than about 99% by weight (S)-3-(Aminomethyl)-5-methylhexanoic acid.

8. The method of claim 1, wherein the retinal pathology is retinitis pigmentosa.

9. The method of claim 8, wherein the retinitis pigmentosa is cone-rod dystrophy.

10. The method of claim 1, wherein the retinal pathology is Stargardt's disease.

11. The method of claim 3, wherein the primary amine compound is selected from the group consisting of (S)-3-(Aminomethyl)-5-methylhexanoic acid, (R)-3-(Aminomethyl)-5-methylhexanoic acid, and racemic mixtures thereof.

12. The method of claim 3, wherein the primary amine compound includes less than about 1% by weight (S)-3-(Aminomethyl)-5-methylhexanoic acid and greater than about 99% by weight (R)-3-(Aminomethyl)-5-methylhexanoic acid.

13. The method of claim 3, wherein the primary amine compound includes less than about 1% by weight (R)-3-(Aminomethyl)-5-methylhexanoic acid and greater than about 99% by weight (S)-3-(Aminomethyl)-5-methylhexanoic acid.

14. The method of claim 3, wherein the retinal pathology is Stargardt's disease.

15. A method of treating Stargardt's disease in a subject in need thereof, comprising administering to the subject a therapeutically effective amount of a primary amine compound selected from (S)-3-(Aminomethyl)-5-methylhexanoic acid, (R)-3-(Aminomethyl)-5-methylhexanoic acid, and racemic mixtures thereof.

16. The method of claim 15, wherein the primary amine compound includes less than about 1% by weight (S)-3-(Aminomethyl)-5-methylhexanoic acid and greater than about 99% by weight (R)-3-(Aminomethyl)-5-methylhexanoic acid.

17. The method of claim 15, wherein the primary amine compound includes less than about 1% by weight (R)-3-(Aminomethyl)-5-methylhexanoic acid and greater than about 99% by weight (S)-3-(Aminomethyl)-5-methyl hexanoic acid.

18. The method of claim 1, wherein the primary compound is delivered to the subject by at least one of topical administration, systemic administration, intravitreal injection, and intraocular delivery.

19. The method of claim 3, wherein the primary compound is delivered to the subject by at least one of topical administration, systemic administration, intravitreal injection, and intraocular delivery.

20. The method of claim 15, wherein the primary compound is delivered to the subject by at least one of topical administration, systemic administration, intravitreal injection, and intraocular delivery.

* * * * *